US006936747B2

(12) United States Patent
Ow

(10) Patent No.: US 6,936,747 B2
(45) Date of Patent: Aug. 30, 2005

(54) METHODS FOR THE REPLACEMENT, TRANSLOCATION AND STACKING OF DNA IN EUKARYOTIC GENOMES

(75) Inventor: David W. Ow, Hercules, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 236 days.

(21) Appl. No.: 09/911,088

(22) Filed: Jul. 23, 2001

(65) Prior Publication Data

US 2002/0123145 A1 Sep. 5, 2002

Related U.S. Application Data

(60) Provisional application No. 60/220,062, filed on Jul. 21, 2000.

(51) Int. Cl.[7] .................. C12N 15/82; C12N 15/87; C12N 15/74; C12N 5/14; A01H 5/00

(52) U.S. Cl. .................. 800/294; 800/288; 800/306; 800/278; 536/23.1; 435/320.1; 435/419

(58) Field of Search ................ 800/278, 288, 800/298, 306; 536/23.1; 435/320.1, 419

(56) References Cited

U.S. PATENT DOCUMENTS

| | | | |
|---|---|---|---|
| 5,190,871 A | 3/1993 | Cox et al. ............... | 435/172.3 |
| 5,527,695 A | 6/1996 | Hodges et al. ........... | 435/172.3 |
| 5,744,336 A | 4/1998 | Hodges et al. ........... | 435/172.3 |
| 5,910,415 A | 6/1999 | Hodges et al. ........... | 435/6 |
| 6,110,736 A | 8/2000 | Hodges et al. ........... | 435/320.1 |
| 6,114,600 A | 9/2000 | Ow et al. ............... | 800/278 |
| 6,175,058 B1 | 1/2001 | Baszczynski et al. ....... | 800/278 |
| 6,187,994 B1 | 2/2001 | Baszczynski et al. ....... | 800/278 |
| 6,262,341 B1 | 7/2001 | Baszczynski et al. ....... | 800/278 |
| 6,632,672 B2 | 10/2003 | Calos | |
| 6,746,870 B1 | 6/2004 | Ow et al. | |

FOREIGN PATENT DOCUMENTS

| | | |
|---|---|---|
| WO | 99/25821 | 5/1999 |
| WO | PCT/US99/18987 | 8/1999 |
| WO | PCT/US00/09154 | 4/2000 |
| WO | PCT/US00/19983 | 7/2000 |

OTHER PUBLICATIONS (Buchanan, et al. Biochemistry & Molecular Biology of Plants (2000) American Society of Plant Physiologists, Rockville Md 20855, p. 322, last paragraph).*
Ow, David W., "Recombinase–directed plant transformation for the post–genomic era", Plant Molecular Biology, 48:183–200 (2002).
Albert et al., Site–specific integration of DNA into wildtype and mutant lox sites placed in the plant genome, 1995 Plant J., 7:649–59.
Alonso et al., The *Bacillus subtilis* Histone–like Protein Hbsu Is Required for DNA Resolution and DNA Inversion Mediated by the β Recombinase of Plasmid pSM19035, 1995 J. Biol. Chem., 270:2938–45.
Araki, H. et al., Site–specific Recombinase, R, Encoded by Yeast Plasmid pSR1, 1992 J. Mol. Biol., 225(1):25–37.
Araki, K. et al., Targeted integration of DNA using mutant lox sites in embryonic stem cells, 1997 Nucleic Acids Res., 25:868–72.
Argos et al., The integrase family of site–specific recombinases: regional similarities and global diversity, 1986 The EMBO J., 5:433–40.
Bannam et al., Molecular genetics of the chloramphenicol–resistance transposon Tn4451 from *Clostridium perfringens*: the TnpX site–specific recombinase excises a circular transposon molecule, 1995 Mol. Microbiology, 16:535–51.
Battacharyya et al., Reduced variation in transgene expression from a binary vector with selectable markers at the right and left T–DNA borders, 1994 Plant J., 6:957–68.
Baubonis and Sauer, Genomic targeting with purified Cre recombinase, 1993 Nucl. Acids Res., 21:2025–29.
Bayley et al., Exchange of gene activity in transgenic plants catalyzed by the Cre–lox site–specific recombination system, 1992 Plant Mol. Biol., 18:353–61.
Bethke and Sauer, Segmental genomic replacement by Cre–mediated recombination: genotoxic stress activation of the p53 promoter in single–copy transformants, 1997 Nucleic Acids Res., 25: 2828–34.
Carrasco et al., *Anabaena xisF* gene encodes a developmentally regulated site–specific recombinase, 1994 Genes & Development, 8:74–83.
Choi et al., A new approach for the identification and cloning of genes: the pBACwich system using Cre/lox site–specific recombination, 2000 Nucl. Acids Res., 28:e19(i–vii).
Corneille et al., Efficient elimination of selectable marker genes from the plastid genome by the CRE–lox site–specific recombination system, 2001 The Plant J., 27:171–78.
Crellin and Rood, The Resolvase/Invertase Domain of the Site–Specific Recombinase TnpX Is Functional and Recognizes a Target Sequence That Resembles the Junction of the Circular Form of the *Clostridium perfringens* Transposon Tn4451, 1997 J. of Bacteriology, 179:5148–56.
Crisona, N.J. et al., Processive Recombination by Wild–type Gin and an Enhancer–independent Mutant, 1994 J. Mol. Biol., 243(3):437–57.

(Continued)

Primary Examiner—Elizabeth F. McElwain
Assistant Examiner—Georgia Helmer
(74) Attorney, Agent, or Firm—Sutherland Asbill & Brennan LLP; Margaret A. Connor

(57) ABSTRACT

The present invention includes compositions and methods for site-specific polynucleotide replacement in eukaryotic cells. These methods include single polynucleotide replacement as well as gene stacking methods. Preferred eukaryotic cells for use in the present invention are plant cells and mammalian cells.

16 Claims, 44 Drawing Sheets

OTHER PUBLICATIONS

Dale and Ow, Gene transfer with subsequent removal of the selection gene from the host genome, 1991 Proc. Natl. Acad. Sci., 88:10558–62.

Dale and Ow, Intra– and intermolecular site–specific recombination in plant cells mediated by bacteriophage P1 recombinase, 1990 Gene 91:79–85.

Davies et al., Somatic and germinal inheritance of an FLP–mediated deletion in transgenic tobacco, 1999 J. of Experimental Botany, 50:1447–56.

Day et al., Transgene integration into the same chromosome location can produce alleles that express at a predictable level, or alleles that are differentially silenced, 2000 Genes & Development, 14:2869–80.

De Buck et al., Transgene silencing of invertedly repeated transgenes is released upon deletion of one of the transgenes involved, 2001 Plant Mol. Biol, 46:433–45.

Diaz et al., The Prokaryotic β–Recombinase Catalyzes Site–specific Recombination in Mammalian Cells, 1999 J. Biol. Chem., 274:6634–6640.

Diaz et al., New Insights into Host Factor Requirements for Prokaryotic β–Recombinase–mediated Reactions in Mammalian Cells, 2001 J. Biol. Chem., 276:16257–64.

Feng et al., Site–specific Chromosomal Integration in Mammalian Cells: Highly Efficient CRE Recombinase–mediated Cassette Exchange, 1999 J. Mol. Biol., 292:779–85.

Finkel and Johnson, The Fis protein: it's not just for DNA inversion anymore, 1992 Mol. Microbiology, 6:3257–65.

Friedman, Integration Host Factor: A Protein for All Reasons, 1988 Cell, 55:545–54.

Gleave et al., Selectable marker–free transgenic plants without sexual crossing: transient expression of cre recombinase and use of a conditional lethal dominant gene, 1999 Plant Mol. Biol., 40:223–35.

Groth et al., A phage integrase directs efficient site–specific integration in human cells, 2000 PNAS, 97:5995–6000.

Hajdukiewicz et al., Multiple pathways for Cre/lox–mediated recombination in plastids, 2001 The Plant J., 27:161–170.

Hatfull and Grindley, Resolvases and DNA–Invertases: a Family of Enzymes Active in Site–Specific Recombination, 1988 Genetic Recombination, 11:357–96.

Hohn et al., Elimination of selection markers from transgenic plants, 2001 Current Opinion in Biotechnology, 12:139–43.

Howe et al., Cis–Effects of Heterochromatin and Euchromatic Gene Activity in *Drosophila melanogaster*, 1995 Genetics, 140:1033–45.

Iyer et al., Transgene silencing in moncots, 2000 Plant Mol. Biol., 43:323–46.

Kaeppler et al., Epigenetic aspects of somaclonal variation in plants, 2000 Plant Mol. Biol., 43:179–88.

Kilby et al., Controlled induction of GUS marked clonal sectors in *Arabidopsis*, 2000 J. of Experimental Botany, 51:853–63.

Kolb and Siddell, Genomic targeting of a bicistronic DNA fragment by Cre–mediated site–specific recombination, 1997, Gene, 203:209–16.

Kolot et al., Site–specific recombination in mammalian cells expressing the Int Recombinase of bacteriophage HK022, 1999 Mol. Biol. Reports, 26:207–13.

Kuhstoss and Rao, Analysis of the Integration Function of the Streptomycete Bacteriophage ΦC31, 1991 J. Mol. Biol., 222:897–908.

Kutsukake K. et al., A gene for DNA invertase and an invertible DNA in *Escherichia coli* K–12, 1985 Gene, 34(2–3):343–50.

Landy, Dynamic, Structural, and Regulatory Aspects of λ Site–Specific Recombination, 1989 Annu. Rev. Biochem., 58:913–49.

Loessner et al., Complete nucleotide sequence, molecular analysis and genome structure of bacteriophage A118 of *Listeria monocytogenes*: implications for phage evolution, 2000 Mol. Microbiology, 35:324:40.

Loonstra et al., Growth inhibition and DNA damage induced by Cre recombinase in mammalian cells, 2001 PNAS, 98:9209–14.

Lorbach et al. Site–specific Recombination in Human Cells Catalyzed by Phage λ Integrase Mutants, 2000 J. Mol. Biol., 296:1175–81.

Lyznik, L.A. et al., FLP–mediated recombination of FRT sites in the maize genome,1996 Nucleic Acids Res., 24(19):3784–9.

Lyznik, L.A. et al., Activity of yeast FLP recombinase in maize and rice protoplasts, 1993 Nucleic Acids Res., 21:969–75.

Maeser and Kahmann, The Gin recombinase of phage Mu can catalyse site–specific recombination in plant protoplasts, 1991 Mol. Gen. Genet., 230:170–76.

Matsuura et al., The sre Gene (ORF469) Encodes a Site–Specific Recombinase Responsible for Integration of the R4 Phage Genome, 1996 J. of Bacteriology, 178:3374–76.

Matzke et al., Transgene silencing by the host genome defense: implications for the evolution of epigenetic control mechanisms in plants and vertebrates, 2000 Plant Mol. Biol., 43:401–15.

Medberry et al., Intra–chromosal rearrangements generated by Cre–lox site–specific recombination, 1995 Nucleic Acids Res., 23:485–90.

Meyer, Transcriptional transgene silencing and chromatin components, 2000 Plant Mol. Biol., 43:221–34.

Muskens et al., Role of inverted DNA repeats in transcriptional and post–transcriptional gene silencing, 2000 Plant Mol. Biol., 43:243–60.

O'Gorman et al., Recombinase–Mediated Gene Activation and Site–Specific Integration in Mammalian Cells, 1991 Science, 251:1351–55.

Onouchi et al., Visualization of site–specific recombination catalyzed by a recombinase from *Zygosaccharomyces rouxii* in *Arabidopsis thaliana*, 1995 Mol. Gen. Genet. 247:653–660.

Ow, The right chemistry for marker gene removal?, 2001 Nature Biotechnology, 19:115–6.

Ow, Recombinase–directed chromosome engineering in plants, 1996 Current Opinion in Biotechnology, 7:181–86.

Ow and Ausubel, Conditionally Replicating Plasmid Vectors That Can Integrate into the *Klebsiella pneumoniae* Chromosome via Bacteriophage P4 Site–Specific Recombination, 1983 J. of Bacteriology, 155:704–13.

Ow and Medberry, Genome Manipulation Through Site–Specific Recombination, 1995 Crit. Rev. Plant Sci., 14:239–261.

Peschke and Phillips, Genetic Implications of Somaclonal Variation in Plants, 1992 Advances in Genetics, 30:41–75.

Qin et al., Cre recombinase–mediated site specific recombination between plant chromosomes, 1994 Proc. Natl. Acad. Sci., 91:1706–10.

Qin et al., Site–specific cleavage of chromosomes in vitro through Cre–lox recombination, 1995 Nucleic Acids Res., 23:1923–7.

Sadowski, Site–Specific Recombinases: Changing Partners and Doing the Twist, 1986 J. of Bacteriology, 165:341–7.

Sadowski, Site–specific recombination : hops, flips, and flops, 1993 FASEB J., 7:760–67.

Sato et al., The cisA Cistron of *Bacillus subtilis* Sporulation Gene spoIVC Encodes a Protein Homologous to a Site–Specific Recombinase, 1990 J. of Bacteriology, 172:1092–8.

Sauer, Site–specific recombination: developments and applications, 1994 Current Opinion in Biotechnology, 5:521–7.

Schmidt et al., Illegitimate Cre–dependent chromosome rearrangements in transgenic mouse spermatids, 2000 PNAS, 97:13702–7.

Schwikardi and Dorge, Site–specific recombination in mammalian cells catalyzed by λδ resolvase mutants: implications for the topolgoy of episomal DNA, 2000 FEBS Let., 471:147–150.

Seibler and Bode, Double–Reciprocal Crossover Mediated by FLP–Recombinase: A Concept and an Assay, 1997 Biochem., 36:1740–7.

Seibler et al., DNA Cassette Exchange in ES Cells Mediated by FLP Recombinase: An Efficient Strategy for Repeated Modification of Tagged Loci by Marker–Free Constructs, 1998 Biochemistry, 37:6229–34.

Srivastava et al., Single–copy transgenic wheat generated through the resolution of complex integration patterns, 1999 Proc. Natl. Acad. Sci. USA, 96:11117–11121.

Srivastava and Ow, Single–copy primary transformants of maize obtained through the co–introduction of a recombinase–expressing construct, 2001 Plant Mol. Biol., 46:561–566.

Stark et al., Catalysis by site–specific recombinases, 1992 TIG, 8:432–9.

Stavenhagen and Zakian, Internal tracts of telomeric DNA act as silencers in *Saccharomyces cerevisiae*,1994 Genes and Dev., 8:1411–22.

Stragier et al., Chromosomal Rearrangement Generating a Composite Gene for a Developmental Transcription Factor, 1989 Science, 243:507–512.

Thomason et al., Gene insertion and replacement in *Schizosaccharomyces pombe* mediated by the *Streptomyces* bacteriophage ΦC31 site–specific recombination system, 2001 Mol. Genet. Genomics, 265:1031–8.

Thorpe & Smith, In vitro site–specific integration of bacteriophage DNA catalyzed by a recombinase of the resolvase/invertase family, 1998 Proc. Nat'l. Acad. Sci. USA, 95:5505–10.

Thyagarajan et al., Site-Specific Genomic Integration in Mammalian Cells Mediated by Phage ΦC31 Integrase, 2001 Mol. and Cell. Biol. 21:3926–34.

Thyagarajan et al., Mammalian genomes contain active recombinase recognition sites, 2000 Gene, 244:47–54.

Tominaga A et al., Site–Specific Recombinase Genes in Three *Shigella* Subgroups and Nucleotide Sequences of a pinB Gene and an Invertible B Segment from *Shigella boydii*, 1991 J. Bacteriol., 173(13):4079–87.

Vergunst et al., Cre/lox–mediated recombination in *Arabidopsis*: evidence for transmission of a translocation and a deletion event, 2000 Chromosoma, 109:287–97.

Vergunst and Hooykaas, Cre/lox–mediated site–specific integration of *Agrobacterium* T–DNA in *Arabidopsis thaliana* by transient expression of cre, 1998 Plant Mol. Biol., 38:393–406.

Vergunst et al., VirB/D4–Dependent Protein Translocation from *Agrobacterium* into Plant Cells, 2000 Science, 290:979–82.

Vergunst et al., Site–specific integration of *Agrobacterium* T–DNA in *Arabidopsis thaliana* mediated by Cre recombinase, 1998 Nucleic Acids Res., 26:2729–34.

Voziyanov et al., A general model for site–specific recombination by the integrase family recombinases, 1999 Nucleic Acids Res., 27:930–41.

Wallrath and Elgin, Position effect variegation in *Drosophila* is associated with an altered chromatin structure, 1995 Genes and Dev., 9:1263–77.

Weisberg and Landy, Site–specific Recombination in Phage Lambda, 1983 Lambda II, Cold Spring Harbor Laboratory 211–50.

Zuo et al., Chemical–regulated, site–specific DNA excision in transgenic plants, 2001 Nature Biotechnology, 19:157–61.

Belteki, et al., "Site–specific cassette exchange and germline transmission with mouse ES cells expressing φC31 integrase," 2003 Nature Biotechnology 21: 321–324.

Gilbertson et al., Conference on In Vitro Technology St. Louis, In: In vitro Cellular & Development Biology Animal, Mar. 2001 37(3 Part 2):26A.

Srivastava & Ow, "Biolistic mediated site–specific integration in rice," 2002 Molecular Breeding, 8: 345–350.

* cited by examiner

Strategy for cDNA integration in mammalian cells

Pc = human cytomegalovirus promoter
Ps = SV40 early promoter
zeo = zeocin resistance coding region
tk = thymidine kinase coding region PP' = attP
BB' = attB
PB' = attR
BP' = attL

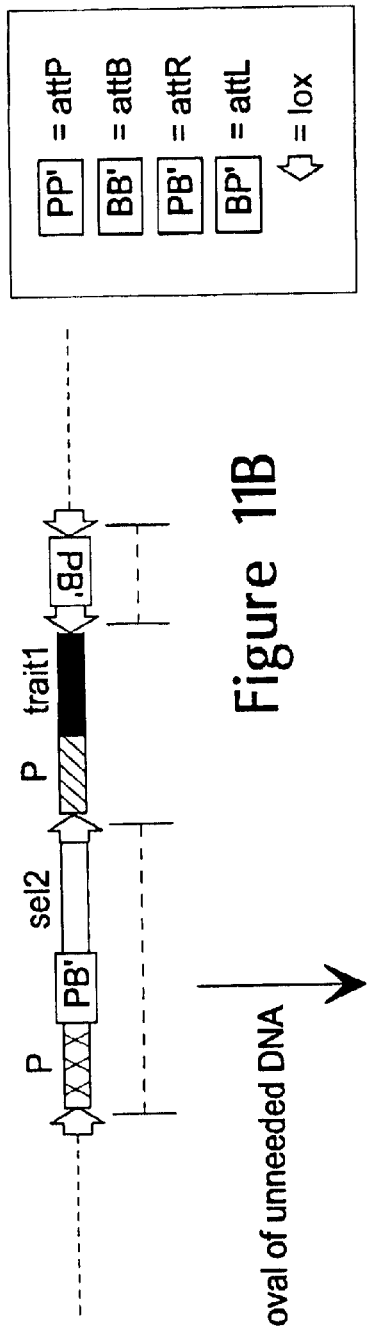
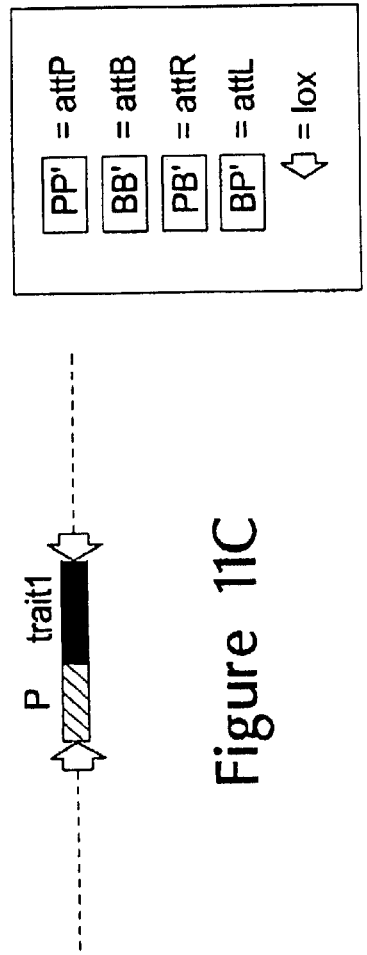
Figure 11B
Figure 11C

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 1
ggccctgaaa ttgttgcttc tgcc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2
gtcaaaaagt ttcgtcaata tcac                                          24

<210> SEQ ID NO 3
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gggcccgcca cgatgacaca aggggttgtg accggggtgg acacgtacgc gggtgcttac    60
gaccgtcagt cgcgcgagcg cgagaattc                                     89

<210> SEQ ID NO 4
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcggtgcggg tgccagggcg tgcccttggg ctccccgggc gcgtactcca cct           53

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
agtagtgccc caactggggt aacctttgag ttctctcagt tgggggcgta ggg           53

METHODS FOR THE REPLACEMENT, TRANSLOCATION AND STACKING OF DNA IN EUKARYOTIC GENOMES

CROSS REFERENCE TO RELATED APPLICATIONS

This application claims the priority benefit of U.S. Provisional Application Ser. No. 60/220,062 filed Jul. 21, 2000.

FIELD OF THE INVENTION

This invention pertains to the field of methods for obtaining specific and stable integration of nucleic acids into chromosomes of eukaryotes. More specifically, the invention relates to methods for obtaining site-specific replacement of nucleic acids in a target construct. The invention makes use of site-specific recombination systems that use prokaryotic recombinase polypeptides, such as the $\phi$C31 integrase.

BACKGROUND

Since the pioneering transformation advances of the early 1980's, much of the research efforts have been directed, and rightly so, to a horizontal spread of the technology. As a result of this emphasis, it is now possible to transform a wide variety of plant species. The trade off, however, has been less attention devoted to advancing the efficiency of the transformation process itself. Compared to many microbial systems, plant transformation appears somewhat antiquated. Whereas millions of independent transformants are routinely obtained with many microbial systems, in plants, the numbers are generally in the single to double-digit range. Hence a shotgun transformation approach to gene discovery is an option that has not been seriously entertained.

Unlike microbial gene transfer that requires analysis of relatively few representative clones due to the highly consistent phenotypes, plant gene transfer involves independent transformants that show highly variable levels and patterns of expression. Accordingly, for a typical DNA construct, twenty to fifty independent primary transformants are needed. For the commercial development of a new trait, hundreds of independent transformants are screened for the few with suitable transgene structure and expression.

The underlying reasons for the high variability in transgene expression in plants are not completely understood, but at least four factors are involved in this phenomenon. (1) Tissue culture: Somaclonal variation has long been associated with tissue culture regenerated plants. Changes in chromosome structure and ploidy, DNA sequence, DNA modification, and transposon activity have all been reported in somaclonal variants (Peschke and Phillips, 1992 Advances in Genetics, 30:41–75; Kaeppler et al., 2000 Plant Mol. Biol., 43:179–88). (2) Integration site: Chromosomal structures such as telomeres or heterochromatin are known to affect the expression of nearby genes (Stavenhagen and Zakian, 1994 Genes and Dev., 8:1411–22; Howe et al., 1995 Genetics, 140:1033–45; Wallrath and Elgin, 1995 Genes and Dev. 9:1263–77). As a transgene integrates at random locations, chromosomal influences on transgene expression can be expected to differ among independent transformants (Meyer, 2000 Plant Mol. Biol., 43:221–34). (3) Transgene redundancy: Transformed plants often contain variable numbers of transgenes. Rarely is there a positive correlation between gene expression and copy number. On the contrary, many cases have linked extra full or partial transgene copies to postranscriptional and transcriptional gene silencing (Muskens et al., 2000 Plant Mol. Biol., 43:243–60; Matzke et al., 2000 Plant Mol. Biol., 43:401–15). (4) Genetic mutations: As expected for any genetic manipulations, there is always the possibility of acquiring point mutations, deletions or rearrangements (Battacharyya et al., 1994 Plant J., 6:957–68).

Current methods in plant gene transfer often produce a complex integration structure at the insertion locus. Typically, multiple full and/or partial copies of the introduced molecule are arranged as direct and/or indirect repeats. Also inserted are selectable markers and other regulatory regions that are unnecessary after selection of a desired organism or plant containing the constructs. These complex patterns are not necessarily an impediment for research, but they are not desirable for commercial use. Structural documentation is a prerequisite for regulatory approval and a simple integration pattern is easier to characterize. Repetitive DNA also tends to be structurally and functionally unstable. Repeat sequences can participate in intra- and inter-chromosomal recombination. Even if a complex integration locus yields a suitable phenotype, it may be difficult to maintain the original structure, along with its defined expression pattern, through the numerous crosses involved in breeding and seed production programs. Multiple gene copies, particularly if some are arranged as indirect repeats, are frequently associated with homology-dependent gene silencing (Iyer et al., 2000 Plant Mol. Biol., 43:179–88; Muskens et al., 2000 supra).

Methods based on site-specific recombination systems have been described to obtain randomly integrated single copy transgenes by excising excess linked copies from the genome (Srivastava and Ow, 1999 Proc. Natl. Acad. Sci. USA, 96:11117–11121; Srivastava and Ow, 2001 Plant Mol. Biol. 46:561–566) and to insert DNA at a known chromosome location in the genome (O'Gorman et al., 1991 Science, 251:1351–55; Baubonis and Sauer, 1993 Nucl., Acids Res., 21:2025–29; Albert et al., 1995 Plant J., 7:649–59). These methods make use of site-specific recombination systems that are freely reversible. These reversible systems include the following: the Cre-lox system from bacteriophage P1 (Baubonis and Sauer, 1993, supra; Albert et al., 1995 Plant J., 7:649–59), the FLP-FRT system of *Sacchromyces cerevisiae* (O'Gorman et al., 1991, supra), the R-RS system of *Zygosaccharomyces rouxii* (Onouchi et al., 1995 Mol. Gen. Genet. 247: 653–660), a modified Gin-gix system from bacteriophage Mu (Maeser and Kahmann, 1991 Mol. Gen. Genet., 230:170–76), the $\beta$-recombinase-six system from a *Bacillus subtilis* plasmid (Diaz et al., 1999 J. Biol. Chem. 274: 6634–6640), and the $\gamma\delta$-res system from the bacterial transposon Tn1000 (Schwikardi and Dorge, 2000 FEBS let. 471: 147–150). Cre, FLP, R, Gin, $\beta$-recombinase and $\gamma\delta$ are the recombinases, and lox, FRT, RS, gix, six and res the respective recombination sites (reviewed by Sadowski, 1993 FASEB J., 7:750–67; Ow and Medberry, 1995 Crit. Rev. Plant Sci. 14: 239–261).

The recombination systems above have in common the property that a single polypeptide recombinase catalyzes the recombination between two sites of identical or nearly identical sequences. Each recombination site consists of a short asymmetric spacer sequence where strand exchange takes place, flanked by an inverted repeat where recombinases bind. The asymmetry of the spacer sequence gives an orientation to the recombination site, and dictates the outcome of a recombination reaction. Recombination between directly or indirectly oriented sites in cis excises or inverts the intervening DNA, respectively. Recombination between sites in trans causes a reciprocal translocation of two linear DNA molecules, or co-integration if at least one of the two molecules is circular. Since the product-sites generated by recombination are themselves substrates for subsequent recombination, the reaction is freely reversible. In practice, however, excision is essentially irreversible because the probability of an intramolecular interaction, where the two recombination-sites are closely linked, is much higher than an intermolecular interaction between unlinked sites. The corollary is that the DNA molecule inserted into a genomic recombination site will readily excise out.

In contrast to the freely reversible recombination systems, there are recombination systems that can catalyze irreversible reactions. In one such system from bacteriophage phage λ, the λ integrase recombines non-similar sequences known as attB and attP to from attL and attR, respectively. This reaction requires DNA supercoiling of the target sites, and accessory proteins IHF and FIS. The reverse reaction, from attLxattR to form attB and attP, requires an additional excision-specific protein known as XIS. Mutant integrase proteins can perform intramolecular, but not intermolecular, reactions without these requirements. Using these mutant λ integrases, Lorbach et al. (2000 J. Mol. Biol., 296:1175–81) demonstrated DNA inversions in recombination targets introduced into the human genome.

A more useful irreversible recombination system described in the prior art is the *Streptomyces* phage φC31 recombination system. A 68 kDa integrase protein recombines an attB site with an attP site. These sites share only three base pairs of homology at the point of cross-over. This homology is flanked by inverted repeats, presumably binding sites for the integrase protein. The minimal known functional size for both the φC31 attB and attP is approximately 30 to 40 base pairs. The efficacy of the φC31 integrase enzyme in recombining its cognate attachment sites was demonstrated in vitro and in vivo in recA mutant *Escherichia coli* (Thorpe & Smith, 1998 Proc. Nat'l. Acad. Sci. USA, 95: 5505–10). Unlike the phage λ system, the φC31 integration reaction is simple in that it does not require a host factor. Unlike the phage λ mutant integrase system, it is capable of intermolecular as well as intramolecular reactions.

Prior art that uses reversible recombination systems require complicated strategies to keep the DNA from excising or exchanging back out from the genome. What are needed in the art are compositions and methods for achieving stable site-specific integration of transgenes such that 1) the DNA molecule is introduced as a single copy; 2) the inserted DNA does not readily excise back out, 3) excess DNA associated with the gene integration process, but is no longer needed afterwards, can be removed, and/or 4) additional DNA can be appended to the existing site adjacent to the previously inserted DNA.

SUMMARY OF THE INVENTION

The present invention fulfills the need for compositions and methods for obtaining stable site-specific integration of transgenes with a limited number of integration and/or excision steps. These integration and/or excision steps lead to 1) the DNA molecule is introduced as a single copy; 2) the inserted DNA does not readily excise back out, 3) excess DNA associated with the gene integration process, but is no longer needed afterwards, can be removed, and/or 4) additional DNA can be appended to the existing site adjacent to the previously inserted DNA.

In particular, the present invention provides a method of gene replacement in a eukaryotic cell that includes the use of irreversible recombination sites and irreversible recombinases such as those from phage φC31. Not only does the present invention provide for the stable integration of a single copy of the introduced DNA, the present invention describes for the first time the use of irreversible recombinases in a manner that results in replacement of a receptor construct with a donor construct in one or two steps. Accordingly, the replacement methods described herein are superior to the integration and excision methods of the prior art.

The present invention specifically provides a method for obtaining site-specific gene replacement in a eukaryotic cell including the steps of: 1) providing a eukaryotic cell that comprises a receptor construct that contains a receptor polynucleotide flanked by two of a irreversible recombination site (hereinafter referred to as "IRS"); 2) introducing into the cell a donor construct that contains a donor polynucleotide flanked by two of a irreversible complementary recombination site (hereinafter referred to as "CIRS"); and 3) contacting the receptor construct and the donor construct with an irreversible recombinase polypeptide. Preferably, the irreversible recombinase polypeptide is a φC31 recombinase, and the recombinase catalyzes recombination between the first (IRS) and second (CIRS) types of recombination sites, resulting in replacement of the receptor polynucleotide with the donor polynucleotide and the formation of a replacement construct (FIG. 1A). In the case of the φC31 recombination sites, if the IRS is attP, then CIRS is attB, or if IRS is attB, then CIRS is attP.

The methods of the present invention can be used to transfer polynucleotides from multiple types of donor constructs into multiple types of receptor constructs. For example, the present invention can be used to transfer polynucleotides from a circular vector such as a plasmid into a chromosome or from a DNA segment from one chromosome to another. The present invention can also be used to transfer a linear polynucleotide of any length, as long as the polynucleotide is located between the two CIRS. Preferably the DNA to be transferred is between 1000–2000 bp. This aspect of the present invention allows for direct transfer of a polynucleotide from a cDNA library into a receptor construct such as a chromosome and eliminates the additional intervening step of cloning the polynucleotide into a plasmid vector.

Also included in the present invention are methods of deleting undesired nucleotide sequences in the replacement construct that include contacting the replacement construct with a reversible recombinase. In these methods, the donor construct and the receptor construct each contain two or more reversible recombination sites (hereinafter referred to as "RRS") that are recognized by the reversible recombinase. In one embodiment, the reversible recombinase is Cre and the recombination sites are lox sites.

Combining both the replacement and deletion strategies, the present invention provides methods for gene stacking in a eukaryotic cell. The method of the present invention results in a precise stacking of a series of trait genes at a genomic location without incorporating other unneeded DNA that could cause additional concerns, such as antibiotic resistance markers. The method is described in further detail below.

These above- and below-described methods can be used to stably integrate a polynucleotide into any eukaryotic cell that can be transformed by a polynucleotide. In a preferred embodiment, the eukaryotic cell is a plant or an animal cell. Accordingly, the present invention additionally includes methods of producing a transgenic mammals and plants. A method described herein for producing a transgenic plant includes the steps of: 1) providing a receptor plant comprising a chromosomal receptor polynucleotide flanked by two of a irreversible recombination site (IRS); 2) providing a donor plant comprising a chromosomal donor polynucleotide flanked by two of a irreversible complementary recombination site (CIRS); and 3) crossing the donor plant and the receptor plant to produce a hybrid transgenic plant. According to the present invention, the transgenic plant produced by this method expresses an irreversible recombinase polypeptide that catalyzes recombination between the IRS and the CIRS and replacement of the receptor polynucleotide with the donor polynucleotide, thereby forming a chromosomal replacement construct in the transgenic plant. In a preferred embodiment, the receptor plant is a single copy receptor line. In further embodiments, progeny of the transgenic plant are selected that contain the replacement construct but do not express the irreversible recombinase polypeptide.

BRIEF DESCRIPTION OF THE DRAWINGS

All Figures depict schematic (not to scale) representations. Whereas promoters for gene transcription are explicitly indicated in the figures, for simplicity, terminators that promote transcription termination and lie downstream of every coding region are not shown as separate elements.

FIGS. 9A–J show a second strategy for "stacking" genes. In this case, inverted recombination sites are employed.

FIGS. 11A–C show a strategy where a single unit of a DNA concatemer can insert into the genome through gene replacement. In this instance, indirectly oriented dual recombination sites are used.

DETAILED DESCRIPTION

Figure 1A:
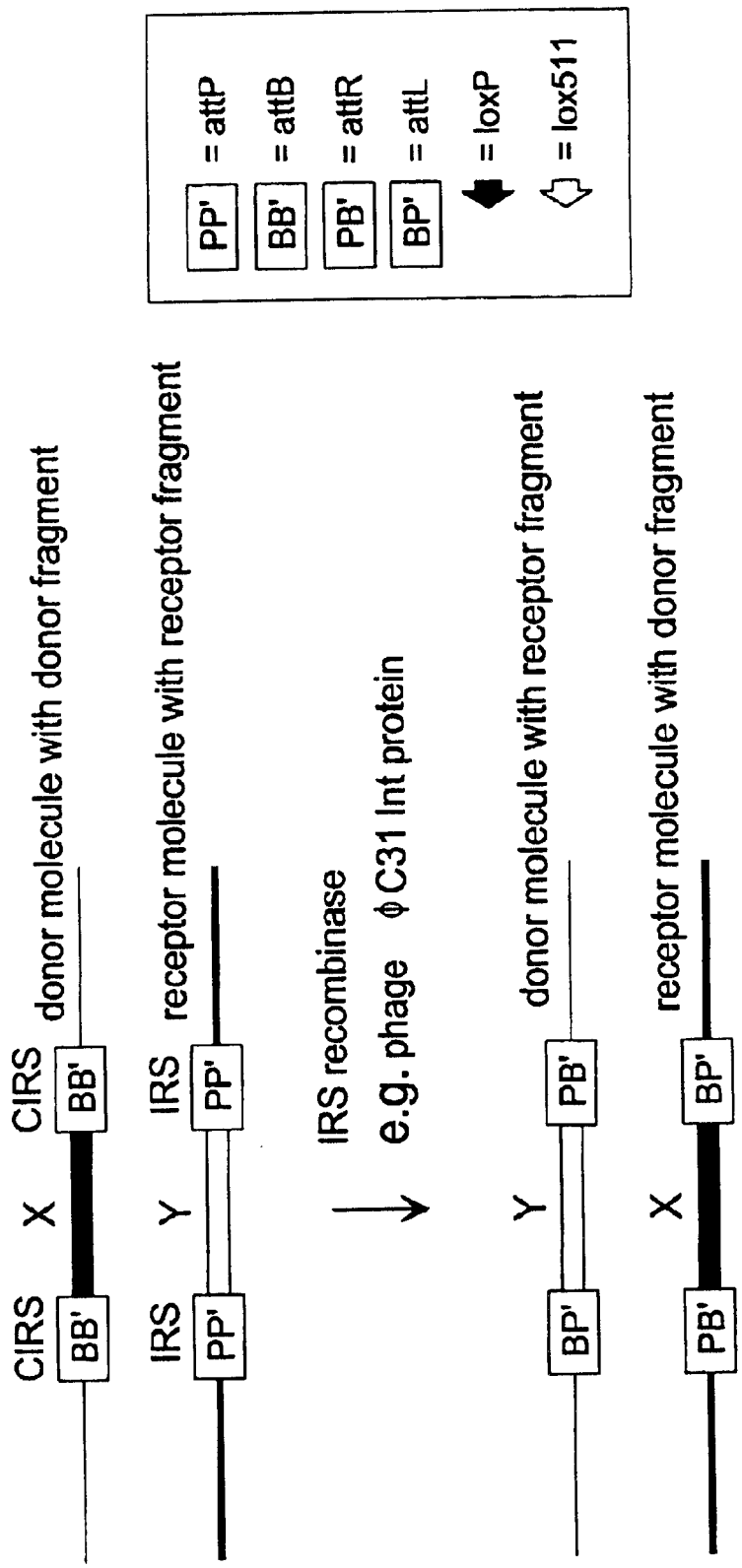
FIGS. 1A and 1B show the DNA exchange reaction by the use of reversible or irreversible recombination systems. In the irreversible recombination system (FIG. 1A), the recombination between IRS and CIRS forms hybrid sites that are no longer recognized by the irreversible recombinase. In the reversible recombination system (FIG. 1B), the recombination between RRS and RRS will produce two product RRS sites that can continue to recombine with each other. Hence DNA that exchanges into the site can also exchange out. This example shows two different RRS sites, designated as RRS-1 and RRS-2.

The present invention provides methods for obtaining stable, site-specific polynucleotide replacement or insertion in eukaryotic cells. For example, the invention provides methods for replacing a gene with a second gene in a site-specific manner. The methods of the invention provide several advantages over previously available methods. For example, the methods of the invention allow one to introduce a linear DNA molecule into the genome of a eukaryotic cell without the need for a selectable marker. Thus, a cDNA molecule, for example, can be introduced into a eukaryotic cell without the need for an intermediate step of cloning the cDNA into a plasmid vector. The invention also provides means for introducing a desired polynucleotide into the chromosome of a eukaryotic cell and subsequently removing unneeded DNA, such as selectable markers and the like, that were used to introduce the DNA into the cells. In addition, one can use the methods of the invention to "stack," or sequentially introduce two or more genes, at a single chromosomal locus.

In a preferred embodiment, the methods of the invention use recombinase systems to achieve stable site-specific replacement of polynucleotides in chromosomes of eukaryotic cells. The term "recombinase system" as used herein refers to a recombinase (reversible or irreversible) and the recombination sites that serve as its substrate in a recombination reaction. Nonetheless, the methods described herein can be used to transfer a polynucleotide from multiple types of donor constructs into multiple types of receptor constructs. For example, the present invention can be used to transfer polynucleotides from a circular vector such as a plasmid to a chromosome, from one circular vector to another, or from one chromosome to another. More importantly, the present invention can be used to transfer linear polynucleotides into chromosomes or circular vectors. Preferably, the linear polynucleotide is approximately about the same length as the receptor site DNA that is being replaced. It is to be understood that the term circular vector encompasses a circular chromosome.

In one embodiment of the present invention, the method for obtaining site-specific gene replacement in a eukaryotic cell includes providing a cell that contains an irreversible recombinase as well as a donor construct and a receptor construct wherein the donor construct comprises two or more IRS and the receptor construct comprises two or more CIRS. The irreversible recombinase catalyzes recombination between the IRS and the CIRS, replaces a receptor polynucleotide with a donor polynucleotide and thereby forms a replacement construct (see FIG. 1). In a preferred embodiment, the receptor construct comprises two IRS and the donor construct comprises two CIRS. In another embodiment, the receptor construct comprises three IRS and the donor construct comprises three CIRS.

As used herein, the term "irreversible recombinase" refers to a polypeptide that can catalyze recombination between two complementary irreversible recombination sites, but cannot catalyze recombination between the hybrid sites that are formed by this recombination without the assistance of an additional factor. Irreversible recombinase polypeptides, and nucleic acids that encode the recombinase polypeptides, are described in the art and can be obtained using routine methods. For example, a vector that includes a nucleic acid fragment that encodes the φC31 integrase is described in U.S. Pat. No. 5,190,871 and is available from the Northern Regional Research Laboratories, Peoria, Ill. 61604 under the accession number B-18477. Examples of other irreversible recombinases include, a coliphage P4 recombinase (Ow & Ausubel, 1983 *J. Bacteriol.* 155: 704–713), a coliphage lambda integrase (Lorbach et al., 2000 J. Mol. Biol., 296:1175–81), a *Listeria* A118 phage recombinase (Loessner et al., 2000 Mol. Micro. 35: 324–340), and an actinophage R4 Sre recombinase (Matsuura et al., 1996 *J. Bacteriol.* 178: 3374–3376).

The terms "irreversible recombination site" and "IRS" therefore refer to a recombination site that can serve as the first of two substrates for an irreversible recombinase and that is modified to a hybrid recombination site following recombination at that site. The terms "complementary irreversible recombination site" and "CIRS" refer to a recombination site that can serve as the second of two substrates for an irreversible recombinase and that is modified to a hybrid recombination site following homologous recombination at that site. Accordingly, in one embodiment of the present invention, a vector donor construct comprises one or more CIRS and a chromosomal receptor construct comprises one or more IRS. In another embodiment, both a chromosomal donor construct comprises two CIRS and a chromosomal receptor construct comprises two IRS.

One example of an irreversible recombinase and its corresponding IRS's is the φC31 integrase and the attB and attP sites. It is to be understood that the attB site and attP site can be referred to as either an IRS or a CIRS. If attB is the IRS, then attP must be the CIRS. Conversely, if attP is the IRS, then attB must be the CIRS. The φC31 integrase, catalyzes only the attB×attP reaction in the absence of an additional factor not found in eukaryotic cells. The recombinase cannot mediate recombination between the attL and attR hybrid recombination sites that are formed upon recombination between attB and attP. Because recombinases such as the φC31 integrase cannot alone catalyze the reverse reaction, the φC31 attB×attP recombination is stable. Thus, the use of these recombinases is unlike other recombination systems, such as the Cre-lox or FLP-FRT systems in which a hybrid site can serve as a substrate for the recombinase, thus resulting in a reversal of the recombination reaction. For example, the insertion of a circular molecule into a target site can lead to the reverse excision of the same introduced DNA. The irreversible recombinases cannot catalyze the reverse reaction, so the integration is stable.

More generally, the term "recombination site" refers to a nucleotide sequence that is recognized by a recombinase and that can serve as a substrate for a recombination event. Although not included within the term "recombination site", the present invention also encompasses the use of "pseudo-recombination sites." Pseudo-recombination sites are polynucleotide sequences that occur naturally in eukaryotic chromosomes and can serve as a substrate for a recombinase. Pseudo-recombination sites are described in, for example, PCT Application No. PCT/US99/18987 (WO 00/11155).

It is to be understood that recombination sites generally have an orientation, or in other words, they are not palindromes. The recombination sites typically include left and right arms separated by a core or spacer region. Thus, an attB recombination site consists of BOB', where B and B' are the left and right arms, respectively, and O is the spacer region. Similarly, attP is POP', where P and P' are the arms and O is again the spacer region. Upon recombination between the attB and attP sites, and concomitant integration of a nucleic acid at the target, the recombination sites that flank the integrated DNA are referred to as "attL" and "aatR." The attL and attR sites, using the terminology above, thus consist of BOP' and POB', respectively. In most representations herein, the "O" is omitted and attB and attP, for example, are designated as BB' and PP', respectively. The orientation of the recombination sites in relation to each other can determine which recombination event takes place. The recombination sites may be in two different orientations: directly oriented (same direction) or oppositely oriented. When the recombination sites are present on a single nucleic acid molecule and are directly oriented with respect to each other, then the recombination event catalyzed by the recombinase is typically an excision of the intervening nucleic acid. When the recombination sites are oppositely oriented, then any intervening sequence is typically inverted.

The recombinases can be introduced into the eukaryotic cells that contain the recombination sites by any suitable method. For example, one can introduce the recombinase in polypeptide form, e.g., by microinjection or other methods. In presently preferred embodiments, however, a gene that encodes the recombinase is introduced into the cells. Expression of the gene results in production of the recombinase, which then catalyzes recombination among the corresponding recombination sites. Additionally, the receptor and donor constructs can be introduced into the eukaryotic cell by conventional transformation methods. If desired, inverted recombination sites can be used to facilitate the construction of single copy transgenes by the resolution of complex integration patterns as described in, for example, U.S. Pat. No. 6,114,600. Alternatively, single copy transgenic recipients can be obtained through molecular screening methods.

Figure 1B:
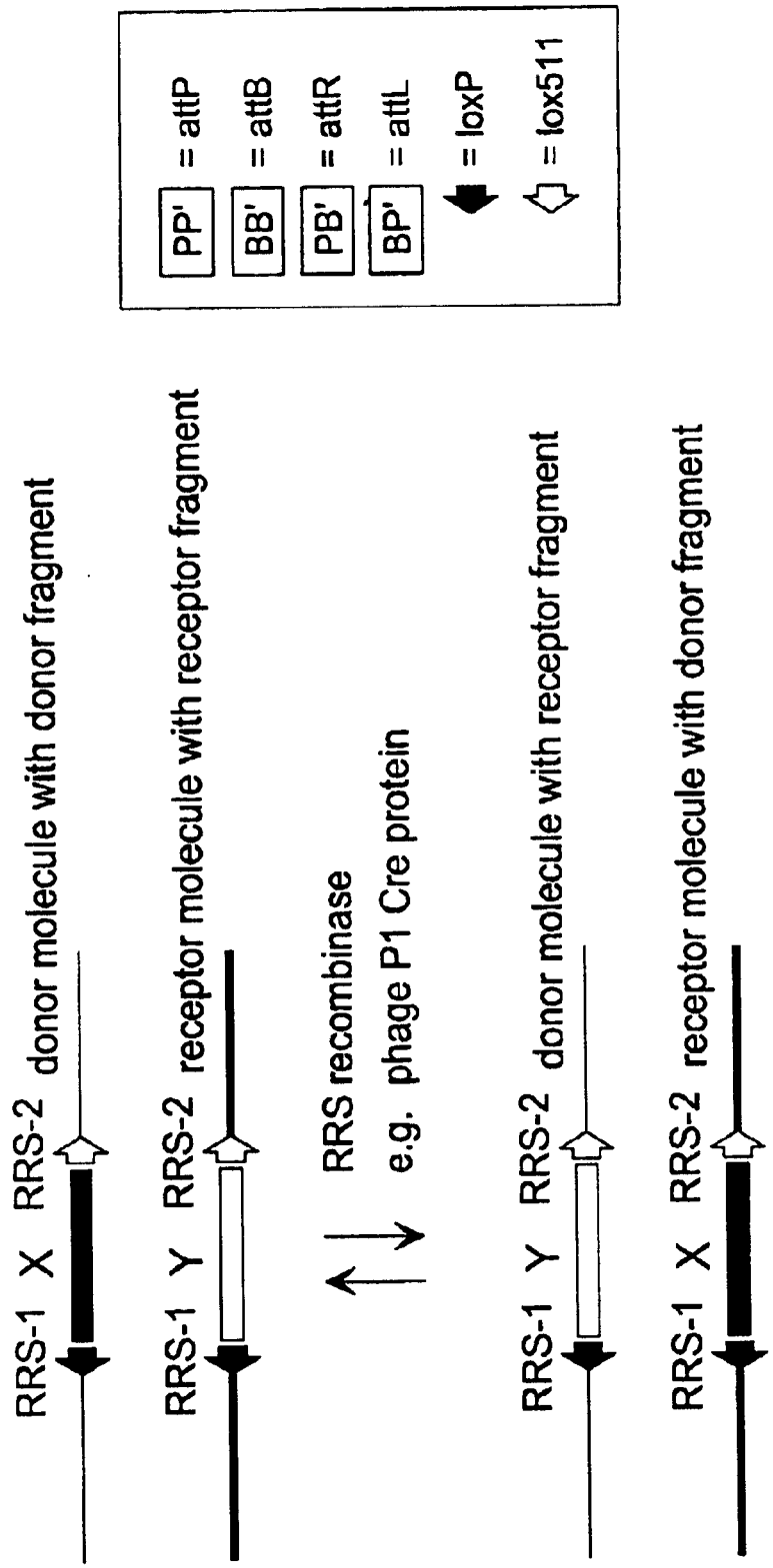

The methods of the present invention can be used to stably integrate polynucleotides into the genome of a host organism. As mentioned above, the present invention provides a method for obtaining site-specific gene replacement in a eukaryotic cell that includes the steps of: 1) providing a eukaryotic cell that comprises a receptor construct containing a receptor polynucleotide flanked by two of an IRS; 2) introducing into the cell a donor construct that contains a donor polynucleotide flanked by two of a CIRS; and 3) contacting the receptor construct and the donor construct with an irreversible recombinase polypeptide. FIG. 1A exemplifies this scheme of events. Note that the use of a reversible recombinase system (see FIG. 1B), such as with the Cre-lox recombination, where Cre recombines loxP with loxP, and lox511 with lox511, will also cause a DNA exchange reaction (lox511 is a variant of the wild type loxP sequence). However, the exchange reaction will be reversible and hence less efficient than the irreversible reaction catalyzed by an irreversible recombinase system. Preferably, the irreversible recombinase polypeptide is a $\phi$C31 recombinase, and the recombinase catalyzes recombination between the IRS and CIRS, resulting in replacement of the receptor polynucleotide with the donor polynucleotide.

In one embodiment of the present invention, the donor polynucleotide includes a promoter operably linked to a gene of interest. "Promoter" refers to a region of DNA involved in binding the RNA polymerase to initiate transcription. An "inducible promoter" refers to a promoter that directs expression of a gene where the level of expression is alterable by environmental or developmental factors such as, for example, temperature, pH, transcription factors and chemicals. A DNA segment is "operably linked" when placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers, for example, need not be contiguous with the coding sequences whose transcription they control. Linking is accomplished by ligation at convenient restriction sites or at adapters or linkers inserted in lieu thereof.

As used herein, the "gene of interest" encodes a polypeptide that imparts a desired trait to the host cell or host organism. The desired trait can be, for example, increased production of an oil or fatty acid, or more simply, increased production of the polypeptide encoded by the gene of interest by the host cell or host organism. It will be understood by those of skill in the art that the "gene of interest" is not limited by the present invention and encompasses any gene that can be expressed in a eukaryotic cell.

In addition to operably linking the gene of interest to a promoter in the donor construct, and more particularly, the donor polynucleotide, it is also desirable to include one or more promoters in the receptor constructs. In a preferred embodiment, the receptor construct includes one promoter that is adjacent to one of the two IRS. More preferably, the promoter is located in the 5 prime direction from one of the two IRS. Placement of a promoter adjacent to an IRS in the receptor construct allows for expression of the donor polypeptide following the recombination event. In further embodiments, the receptor constructs include additional promoters operably linked to selectable markers or the recombinase gene itself.

A promoter can be naturally associated with the gene of interest, or it can be a heterologous promoter that is obtained from a different gene, or from a different species. Where direct expression of a gene in all tissues of a transgenic plant or other organism is desired, one can use a "constitutive" promoter, which is generally active under most environmental conditions and states of development or cell differentiation. Suitable constitutive promoters for use in plants include, for example, the cauliflower mosaic virus (CaMV) 35S transcription initiation region and region VI promoters, the 1'- or 2'-promoter derived from T-DNA of *Agrobacterium tumefaciens,* and other promoters active in plant cells that are known to those of skill in the art. Other suitable promoters include the full-length transcript promoter from Figwort mosaic virus, actin promoters, histone promoters, tubulin promoters, the mannopine synthase promoter (MAS), various ubiquitin or polyubiquitin promoters derived from, inter alia, *Arabidopsis* (Sun and Callis, 1997 *Plant J.,* 11(5):1017–1027), the mas, Mac or DoubleMac promoters (described in U.S. Pat. No. 5,106,739 and by Comai et al., 1990 Plant Mol. Biol. 15:373–381) and other transcription initiation regions from various plant genes known to those of skill in the art. Such genes include for example, ACT11 from *Arabidopsis* (Huang et al., 1996 Plant Mol. Biol., 33:125–139), Cat3 from *Arabidopsis* (GenBank No. U43147, Zhong et al., 1996 Mol. Gen. Genet., 251:196–203), the gene encoding stearoyl-acyl carrier protein desaturase from *Brassica napus* (GenBank No. X74782, Solocombe et al., 1994 Plant Physiol., 104:1167–1176), GPc1 from maize (GenBank No. X15596, Martinez et al., 1989 J. Mol. Biol., 208:551–565), and Gpc2 from maize (GenBank No. U45855, Manjunath et al., 1997 Plant Mol. Biol., 33:97–112).

Other useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter and the nopaline synthase promoter. Suitable endogenous plant promoters include the ribulose-1,6-biphosphate (RUBP) carboxylase small subunit (ssu) promoter, the α-conglycinin promoter, the phaseolin promoter, the ADH promoter, and heat-shock promoters.

Generally, a polynucleotide that is to be expressed (e.g., a gene of interest) will be present in an expression cassette, meaning that the polynucleotide is operably linked to expression control sequences, e.g., promoters and terminators, that are functional in the host cell of interest. Expression cassettes for use in *E. coli* include the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1-10 (Johnson and Davies, 1984 Mol. Cell. Biol., 4:1440–1448) ADH2 (Russell et al., 1983 J. Biol. Chem., 258:2674–2682), PHO5 (Meyhack et al., 1982 EMBO J., 6:675–680), and MFα (Herskowitz and Oshima, 1982, in *The Molecular Biology of the Yeast Saccharomyces* (eds. Strathern, Jones, and Broach) Cold Spring Harbor Lab., Cold Spring Harbor, N.Y., pp. 181–209).

Alternatively, one can use a promoter that directs expression of a gene of interest in a specific tissue or is otherwise under more precise environmental or developmental control. Such promoters are referred to here as "inducible" or "repressible" promoters. Examples of environmental conditions that may effect transcription by inducible promoters include pathogen attack, anaerobic conditions, ethylene, elevated temperature or the presence of light. Promoters under developmental control include promoters that initiate transcription only in certain tissues, such as leaves, roots, fruit, seeds, or flowers. The operation of a promoter may also vary depending on its location in the genome. Thus, an inducible promoter may become fully or partially constitutive in certain locations. Inducible promoters are often used to control expression of the recombinase gene, thus allowing one to control the timing of the recombination reaction.

The tissue-specific E8 promoter from tomato is particularly useful for directing gene expression so that a desired gene product is located in fruits. See, e.g., Lincoln et al., 1988 Proc. Nat'l. Acad. Sci. USA, 84: 2793–2797; Deikman et al., 1988 EMBO J., 7: 3315–3320; Deikinan et al., 1992 Plant Physiol., 100: 2013–2017. Other suitable promoters include those from genes encoding embryonic storage proteins. Additional organ-specific, tissue-specific and/or inducible foreign promoters are also known (see, e.g., references cited in Kuhlemeier et al., 1987 Ann. Rev. Plant Physiol., 38:221), including those 1,5-ribulose bisphosphate carboxylase small subunit genes of *Arabidopsis thaliana* (the "ssu" promoter), which are light-inducible and active only in photosynthetic tissue, anther-specific promoters (EP 344029), and seed-specific promoters of, for example, *Arabidopsis thaliana* (Krebbers et al., 1988 Plant Physiol., 87:859). Exemplary green tissue-specific promoters include the maize phosphoenol pyruvate carboxylase (PEPC) promoter, small submit ribulose bis-carboxylase promoters (ssRUBISCO) and the chlorophyll a/b binding protein promoters. The promoter may also be a pith-specific promoter, such as the promoter isolated from a plant TrpA gene as described in International Publication No. WO/93/07278.

Inducible promoters for other organisms include, for example, the arabinose promoter, the lacZ promoter, the metallothionein promoter, and the heat shock promoter, as well as many others that are known to those of skill in the art. An example of a repressible promoter useful in yeasts such as *S. pombe* is the *Pmnt* promoter, which is repressible by vitamin B1.

Using the present invention, a gene of interest operably linked to one or more of the above-described promoters can be transferred to a receptor cell, and more particularly, can be integrated into a receptor construct. Additionally, a gene of interest can be operably linked to a promoter in the receptor construct upon integration of the gene of interest into the receptor construct. One advantage of the present invention is that the gene of interest can be inserted into the receptor construct in either the sense or antisense orientation, and thus transcribed as a sense or antisense mRNA. Both sense and antisense expression of the gene of interest can be achieved by flanking the gene of interest with two IRS that are inverted with respect to each other and flanking the receptor polynucleotide with two CIRS that are inverted with respect to each other. (See FIG. 5 for an example). This strategy is particularly useful wherein the donor construct is a linear DNA construct such as a cDNA from a cDNA library. The present invention therefore encompasses a eukaryotic cell comprising 1) a donor construct including a gene of interest flanked by two IRS that are inverted with respect to each other, 2) a receptor construct including a promoter adjacent to a receptor polypeptide flanked by two CIRS that are inverted with respect to each other, and 3) an irreversible recombinase polypeptide, wherein contacting the donor construct and the receptor construct results in recombination between the IRS and CIRS and replacement of the receptor polynucleotide with the donor polynucleotide. The present invention further encompasses a method of achieving antisense expression of a gene of interest comprising 1) introducing into a eukaryotic cell a) a donor construct including a gene of interest flanked by two IRS that are inverted with respect to each other, b) a receptor construct including a promoter adjacent to a receptor polypeptide flanked by two CIRS that are inverted with respect to each other, and c) an irreversible recombinase polypeptide and 2) contacting the donor construct and the receptor with the irreversible recombinase polypeptide such that recombination between the IRS and CIRS and replacement of the receptor polynucleotide with the donor polynucleotide occurs. Eukaryotic cells containing replacement constructs with the gene of interest in an antisense orientation are then selected by methods well known to those of skill in the art.

The present invention is also particularly useful for integrating a single unit copy of a concatemeric DNA molecule into a eukaryotic host cell. Certain methods of introducing DNA into cells, such as biolistic delivery, are often associated with the insertion of a large number of linked DNA molecules. It is thought that this is caused by the prior ligation of linear DNA molecules, which are produced through breakage of the introduced circular plasmid DNA. The invention provides methods by which a single unit copy within the concatemeric DNA, without the rest of the concatemer, can be integrated into the receptor target site. This strategy is sometimes more efficient that the integration of intact circular DNA as exemplified by FIG. 3A. The higher efficiency is due to substrate availability. Direct DNA delivery methods produce a high percentage of concatemerization of extrachromosomal molecules, which reduces the number of the single copy circular substrates for the cointegration reaction. For an exchange reaction, concatemers are still effective, as the only requirement in a substrate are two CIRS flanking the donor polynucleotide, as in FIG. 3B, or in FIGS. 10 and 11.

Figure 5A:
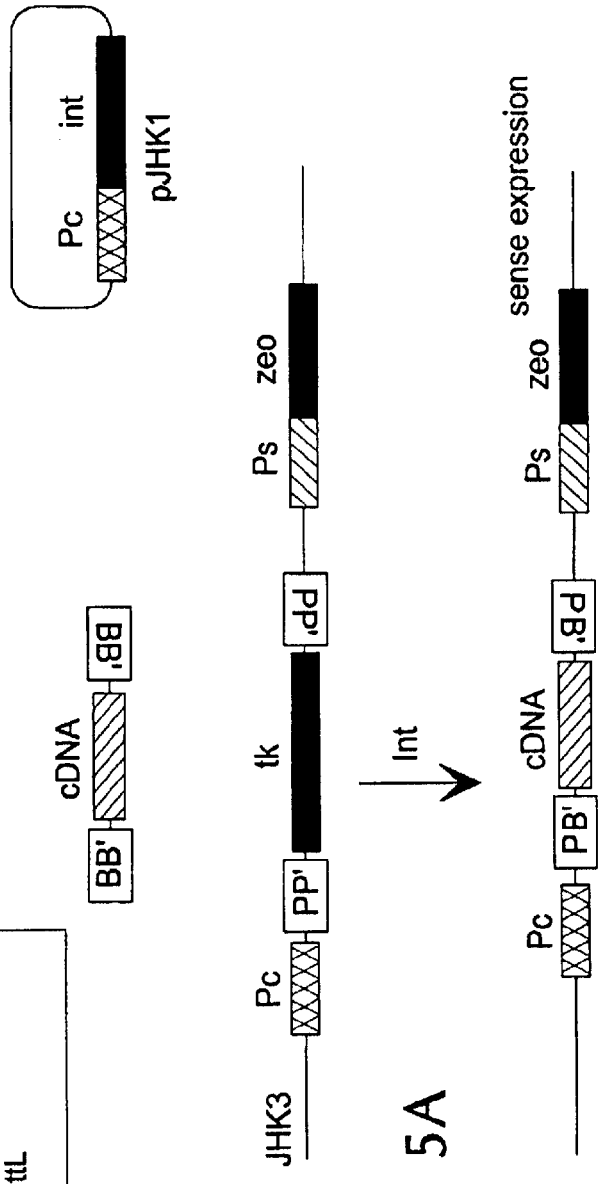
FIGS. 5A and 5B show a strategy for sense and antisense expression of a linear cDNA upon integration into a mammalian cell. In this case, each pair of IRS or CIRS is arranged as indirect repeat sequences.
Figure 5B:
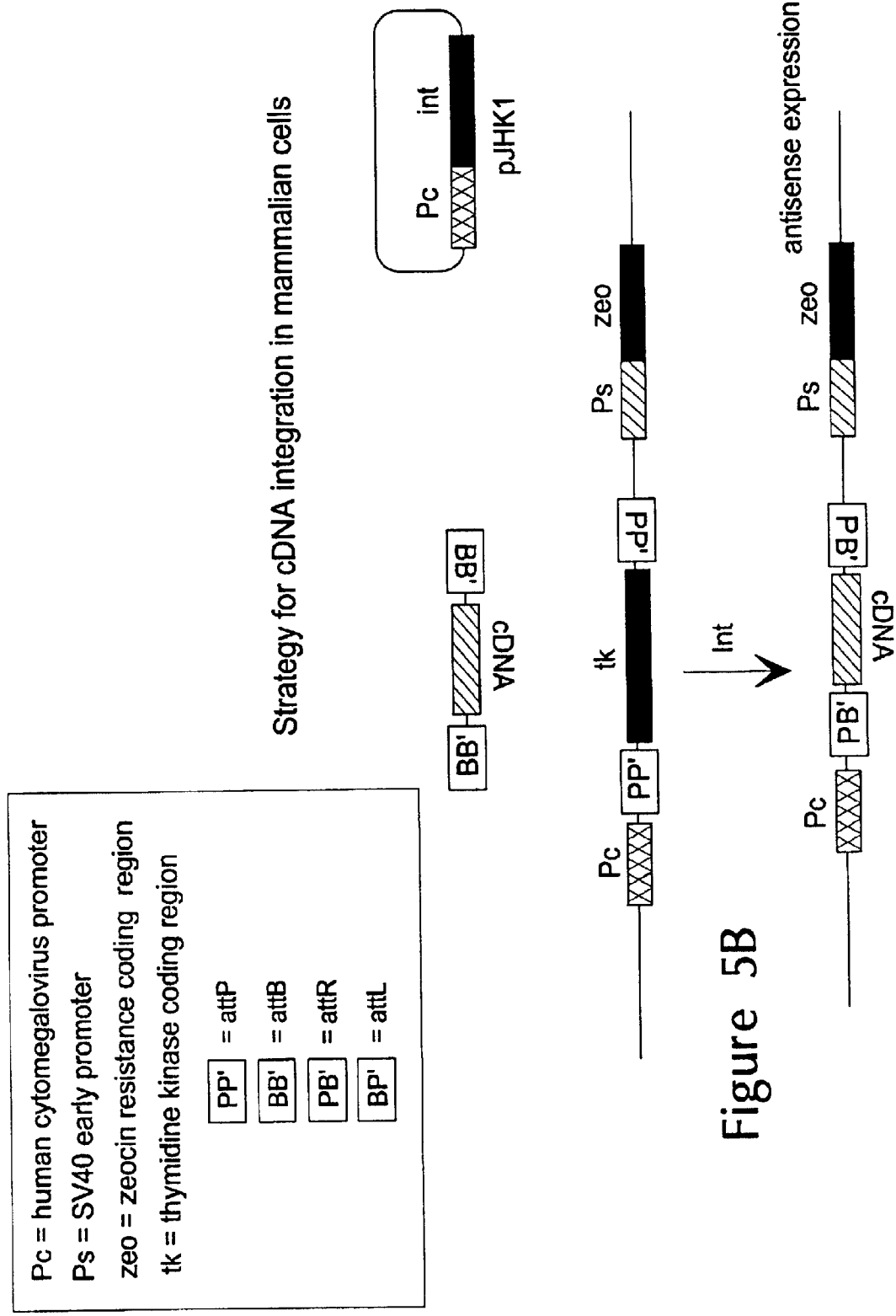
Figure 6A:
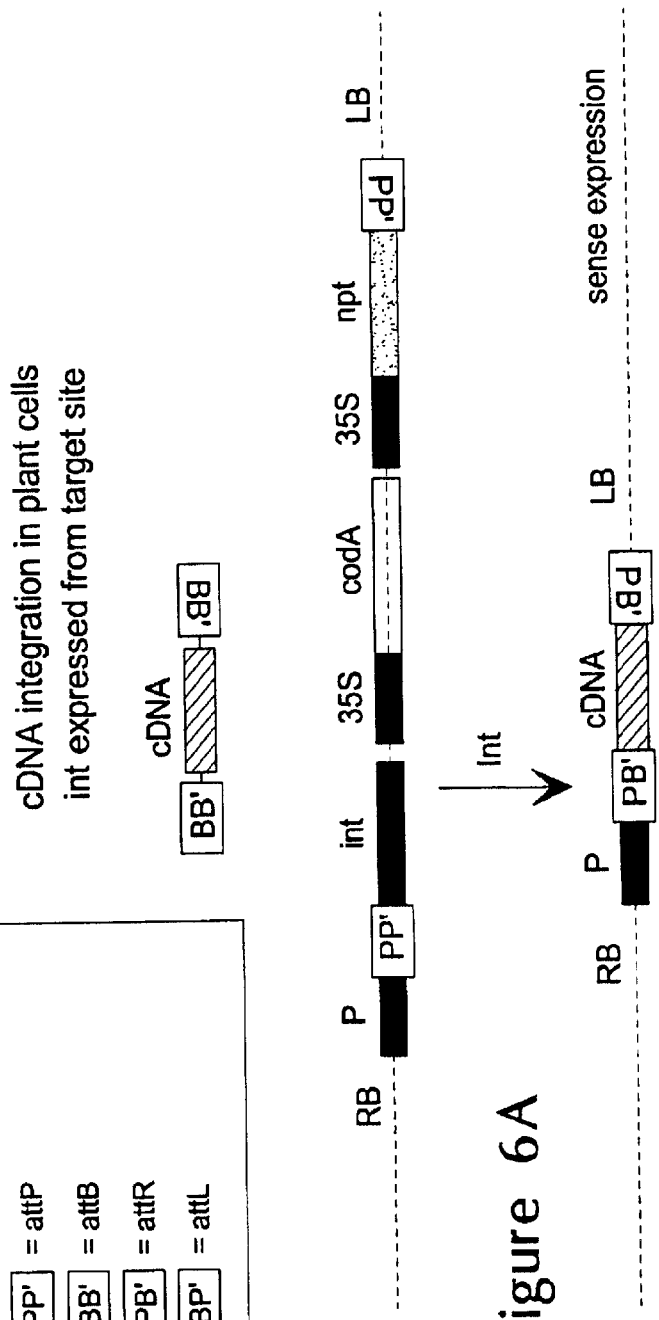
FIGS. 6A and B show a strategy for sense and antisense expression of a cDNA upon integration into a plant cell. No selectable marker is attached to the cDNA in the practice of these methods.
Figure 6B:
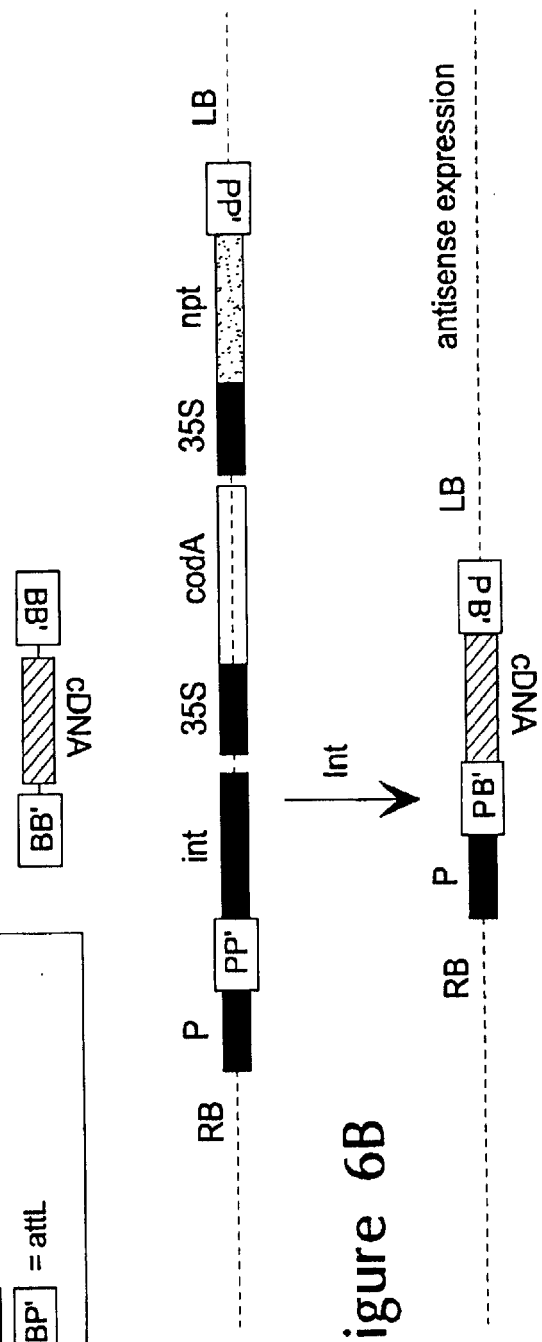

In order for site-specific gene replacement to take place in a host cell of the present invention, a recombinase polypeptide must be present in the cell. In some embodiments of the invention, the introduction of the recombinase is accomplished by introducing a nucleic acid that encodes the recombinase into the cell. A gene that encodes the recombinase can be either transiently or stably expressed in the cells. One can introduce the recombinase gene into the cell before, after, or simultaneously with, the introduction of the donor construct. The recombinase gene can be present within the donor construct itself or a separate vector. FIGS. 5A–B show one embodiment of the present invention wherein the recombinase gene is present on a separate vector. However, it is preferable that the recombinase gene is present within the receptor construct, and more preferably, within the receptor polynucleotide. FIG. 6A–B show a preferred site-specific replacement strategy wherein the recombinase gene is present within the receptor polynucleotide. In other embodiments, the recombinase gene is introduced into a transgenic eukaryotic organism, e.g., a transgenic plant, animal, fungus, or the like, which is then crossed with an organism that contains the donor and receptor constructs containing the IRS and CIRS. The present invention thus provides nucleic acids that include recombination sites, as well as nucleic acids in which a recombinase-encoding polynucleotide sequence is operably linked to a promoter which functions in the target eukaryotic cell.

Figure 4:
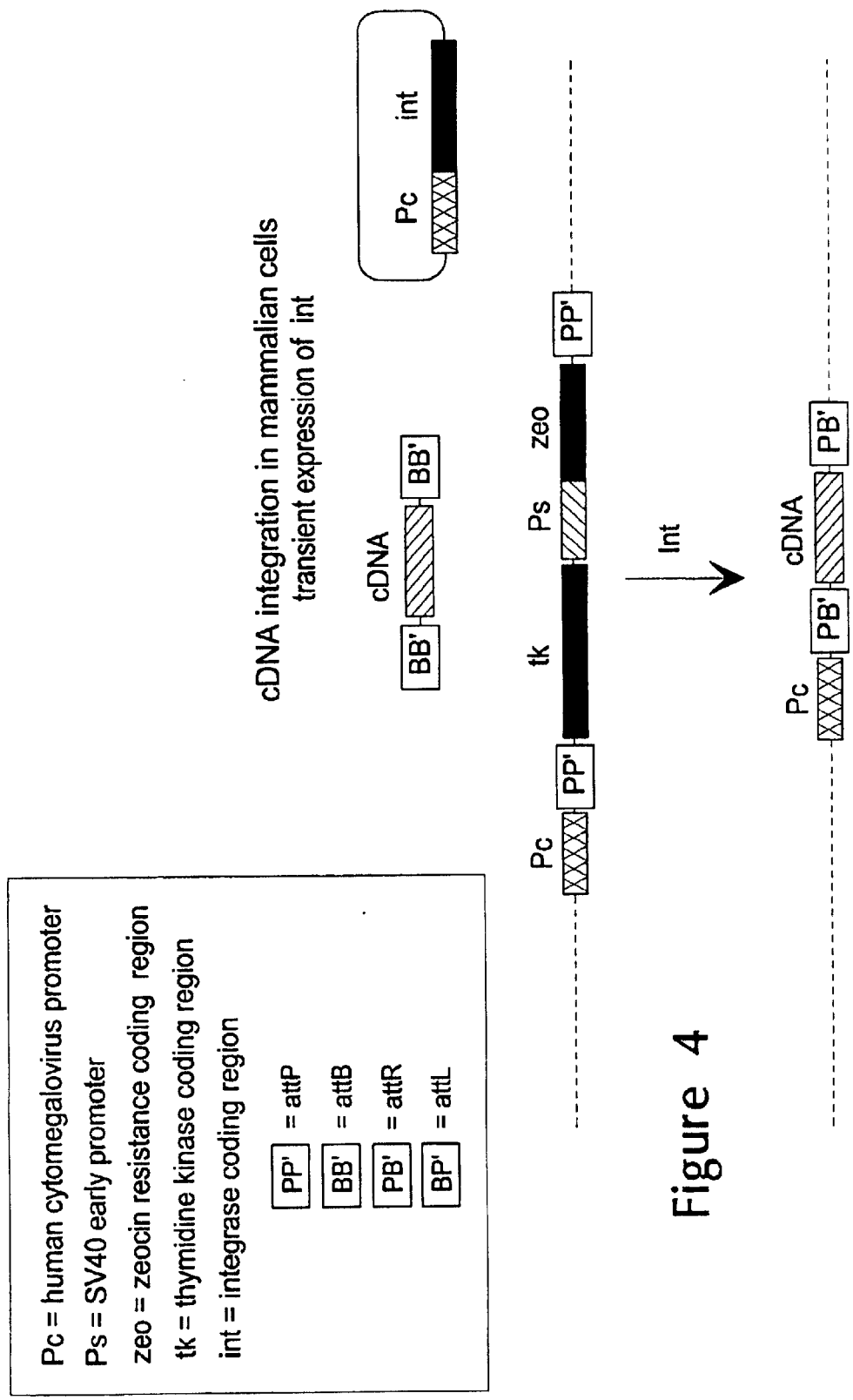
FIG. 4 shows a strategy for integration of a linear cDNA molecule into a chromosome of a mammalian cell. In this case, each pair of IRS or CIRS is arranged as direct repeat sequences.

To facilitate selection of cells in which the desired gene replacement has occurred, the target construct can include (preferably between the recombination sites) a negative selectable marker. After introduction of the integrating construct and contacting with the recombinase, the cells are then subjected to negative selection to eliminate those cells that retain the negative selectable marker. Suitable examples of negative selection markers are known to those of skill in the art, and include, for example, the Herpes simplex virus thymidine kinase gene that results in killing the mammalian cells upon contact with ganciclovir. By this method, one can select for a desired gene replacement event without the resulting transformed cell having extraneous DNA such as an antibiotic resistance gene or other selectable marker. FIG. 4 shows a preferred site-specific replacement strategy utilizing such a negative selectable marker.

Figure 7A:
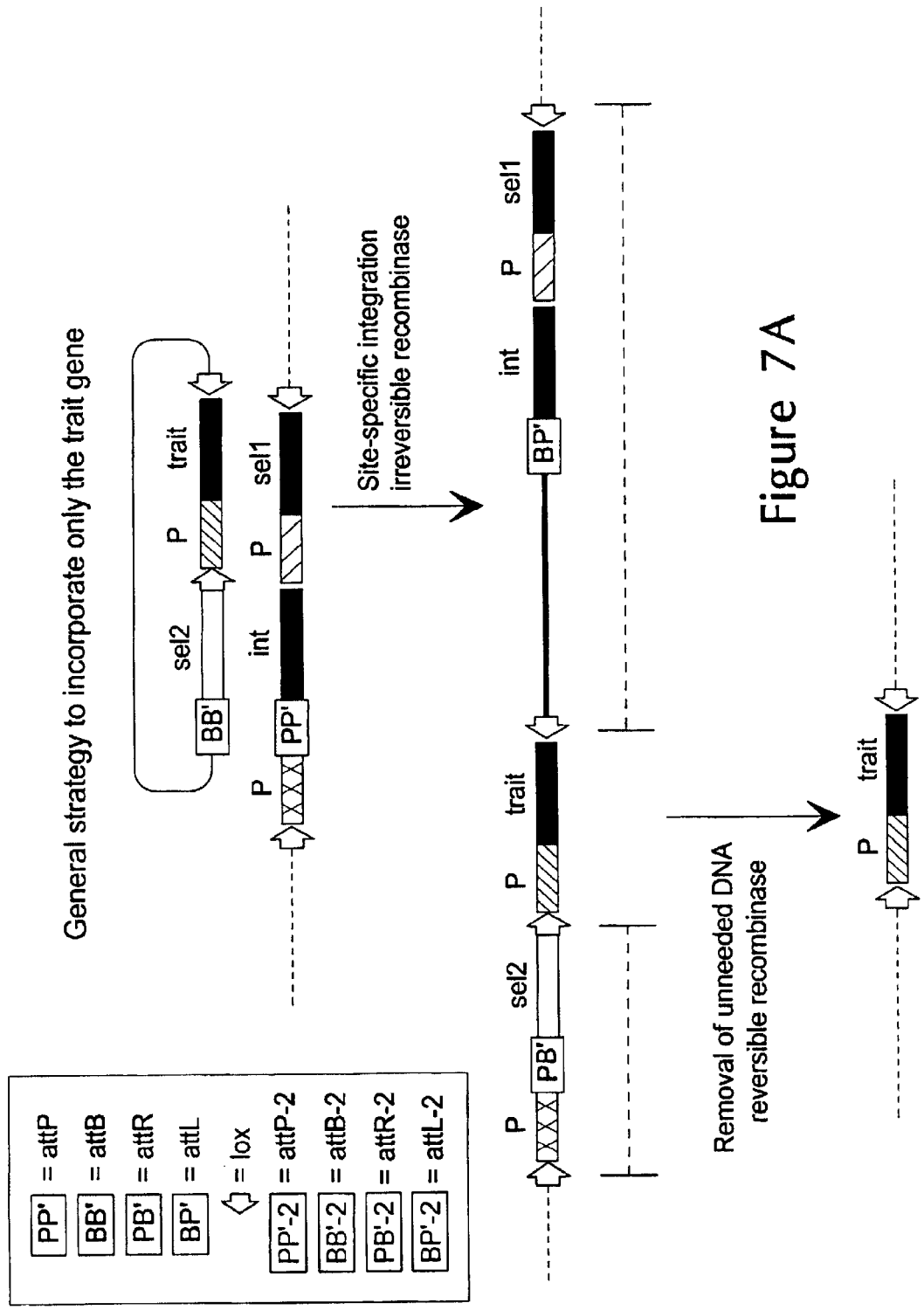
FIG. 7 shows a general strategy for incorporating only a desired polynucleotide. Extraneous DNA such as selectable markers is removed. Open arrowheads represent recombination sites for a reversible recombinase; "int" is a gene that encodes a recombinase, "sel1" and "sel2" are selectable markers, "P" is a promoter, and "trait" is a polynucleotide of interest that when expressed confers a desired trait upon a cell.
Figure 7B:
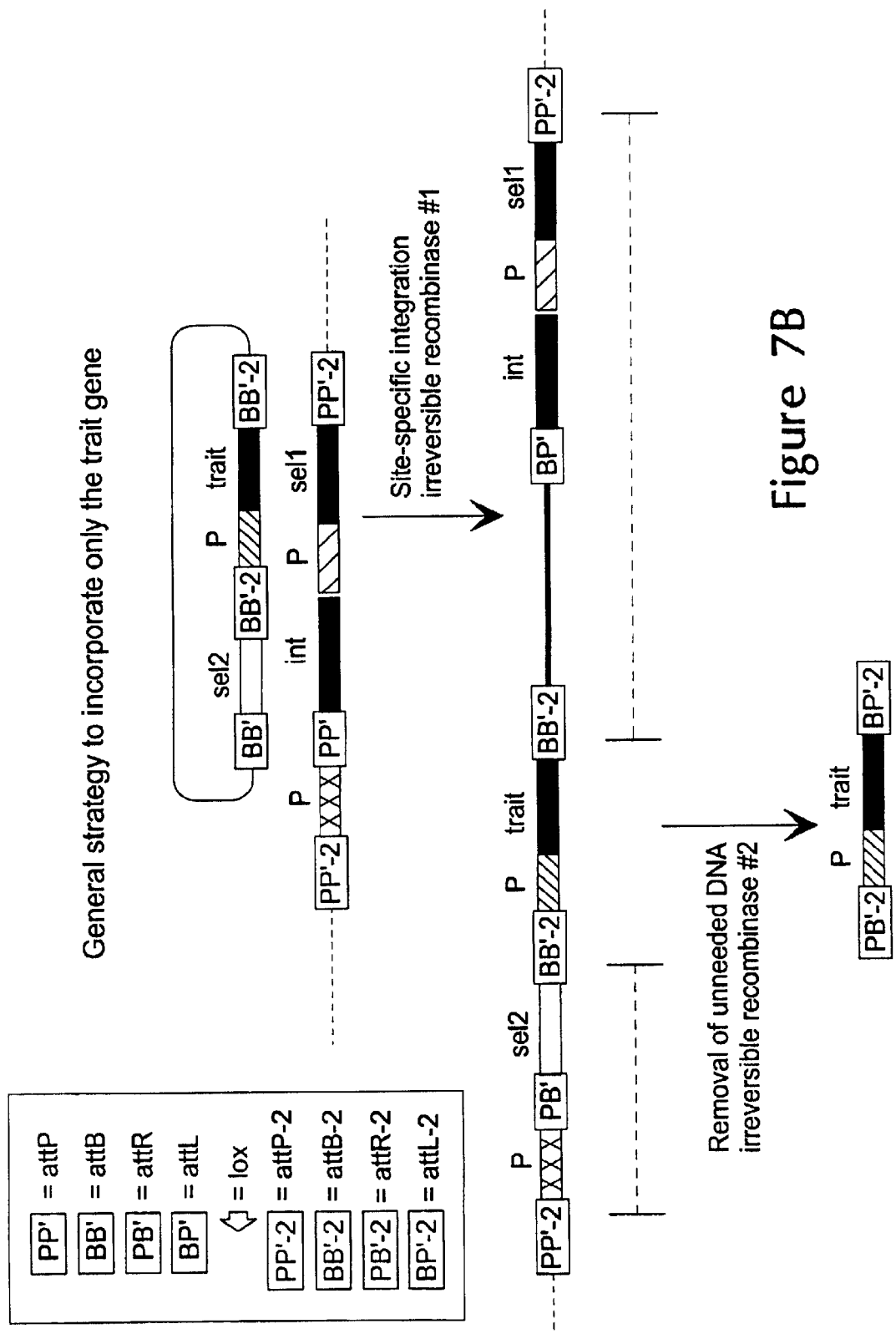

Also included in the present invention are methods of deleting undesired nucleotide sequences in the replacement construct that includes contacting the replacement construct with a second recombinase. In these methods, the donor construct and the receptor construct each contain two or more reversible recombination sites (hereinafter referred to as "RRS") that are recognized by (or compatible with) the reversible recombinase. However, the method can also operate if the second recombinase is a irreversible recombinase. FIG. 7 illustrates the deletion of DNA that is no longer needed with the use of a second recombinase system, either of a reversible type (FIG. 7A) or a irreversible type (FIG. 7B), where the corresponding IRS and CIRS are denoted as attP-2 and attB-2.

Similar to irreversible recombinases, reversible recombinases catalyze recombination between two complementary RRS. The recombinase and recombination sites are termed "reversible" because the product-sites generated by recombination are themselves substrates for subsequent recombination. Suitable reversible recombinase systems are well known to those of skill in the art and include, for example, the Cre-lox system. In the Cre-lox system, the recombination sites are referred to as "lox sites" and the recombinase is referred to as "Cre". When lox sites are in parallel orientation (i.e., in the same direction), then Cre catalyzes a deletion of the intervening polynucleotide sequence. When lox sites are in the opposite orientation, the Cre recombinase catalyzes an inversion of the intervening polynucleotide sequence. This system functions in various host cells, including *Saccharomyces cerevisiae* (Sauer, B., 1987 Mol Cell Biol., 7:2087–2096); mammalian cells (Sauer et al., 1988 Proc. Nat'l. Acad. Sci. USA, 85:5166–5170; Sauer et al., 1989 Nucleic Acids Res., 17:147–161); and plants such as tobacco (Dale, et al., 1990 Gene, 91:79–85) and *Arabidopsis* (Osborne et al., 1995 Plant J., 7(4):687–701). Use of the Cre-lox recombinase system in plants is also described in U.S. Pat. No. 5,527,695 and PCT application No. WO 93/01283. Several different lox sites are known, including lox511 (Hoess R. et al., 1986 Nucleic Acids Res., 14:2287–2300), lox66, lox71, lox76, lox75, lox43, lox44 (Albert et al., 1995 Plant J., 7(4): 649–659).

Several other recombination systems are also suitable for use in these applications. These include, for example, the FLP/FRT system of yeast (Lyznik, L. A. et al., 1996 Nucleic Acids Res., 24(19):3784-9), the Gin recombinase of phage Mu (Crisona, N. J. et al., 1994 J. Mol. Biol., 243(3):437–57), the Pin recombinase of *E. coli* (see, e.g., Kutsukake K, et. al.,1985 Gene, 34(2–3):343–50), the PinB, PinD and PinF from *Shigella* (Tominaga A et al., 1991 J. Bacteriol., 173 (13):4079–87), and the R/RS system of the pSR1 plasmid (Araki, H. et al., 1992 J. Mol. Biol., 225(1):25–37). Thus, recombinase systems are available from a large and increasing number of sources. In one embodiment of the present invention, the reversible recombinase is Cre and the RRS are lox sites.

With reversible recombination systems, the RRS in both the donor construct and the receptor construct are identical or nearly identical. It is also preferable that the RRS in the donor construct are oppositely oriented and that the RRS in the receptor construct are oppositely oriented. In these embodiments, site-specific replacement of the receptor construct by the donor construct results in a replacement construct containing RRS pairs that are directly oriented. Thus, one member of the one or more pairs of the directly oriented reversible recombination sites in the replacement construct is derived from the receptor construct and the other member of the one or more pairs is derived from the donor polynucleotide. Contacting the replacement construct with a reversible recombinase results in the excision of the polynucleotide sequences between the directly oriented RRS. Exemplary constructs containing RRS are shown in FIGS. 7–13.

In one embodiment of the present invention, polynucleotide sequences in the replacement construct that are unnecessary in the desired final construct are deleted using the above-described methods. (See FIGS. 7–13 for various examples). More particularly, as in FIG. 10, the donor construct includes a selectable marker, a promoter operably linked to a gene of interest flanked by two RRS, and this entire segment is flanked by two IRS. The two RRS in the donor construct are oppositely oriented. The receptor construct includes a receptor polynucleotide comprising an integrase coding region, a promoter, and a selectable marker, wherein the receptor polynucleotide is flanked by two CIRS, and a promoter, wherein the receptor polynucleotide and the promoter are flanked by two RRS. The two RRS in the receptor construct are oppositely oriented and each RRS in the receptor construct is recombinogenic to a RRS in the donor construct. (For an example, see FIG. 9). In another embodiment, the IRS are inverted with respect to each other and the CIRS are inverted with respect to each other. (See FIG. 11).

In addition to the above-described methods, the invention also provides methods for sequential "stacking" of multiple polynucleotides of interest at a specific chromosomal locus. The stacking is accomplished without having to incorporate unneeded DNA in the final product. A schematic diagram of two embodiments of this method is shown in FIGS. 8 and 9. In the stacking methods of the present invention, the receptor construct is the same as that described earlier (shown in FIG. 7A). The donor construct (FIG. 8A) used in these methods includes a gene of interest and a single CIRS (e.g., attB of the φC31 system); these components are flanked by a pair of inverted RRS (e.g., lox sites). Also present in the donor construct is a selectable marker coding region, but no promoter for the selectable marker. Preferably, this marker is different from that used on the receptor construct. Upstream of the selectable marker coding region is a second CIRS (e.g. attB of the φC31 system).

The receptor construct is integrated into the chromosome of the host cell using conventional methods, as described above. Again, if desired, flanking inverted recombination sites can be used to facilitate the construction of single copy transgenes by the resolution of complex integration patterns as described in, for example, U.S. Pat. No. 6,114,600. Alternatively, single copy transgenic recipients can be obtained through molecular screening methods.

Figure 8A:
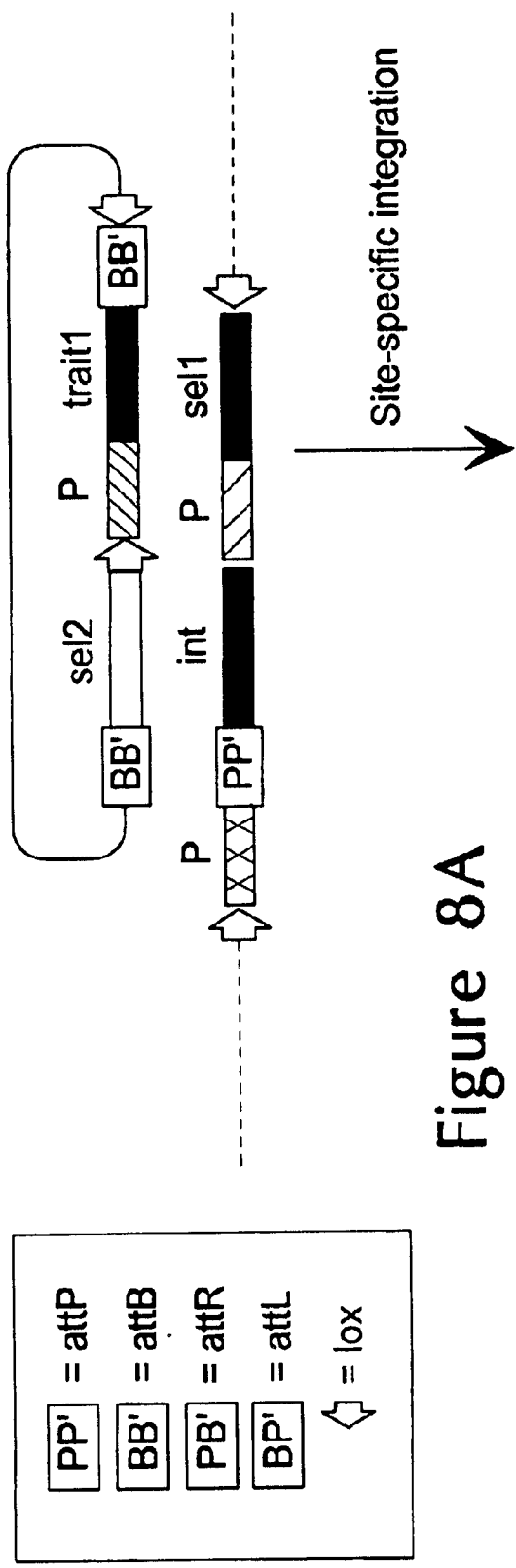
FIGS. 8A–J show a general strategy for "stacking" genes. "trait 1", "trait 2" etc., are individual genes of interest that, when expressed, confer a desired trait upon a cell.
Figure 8B:
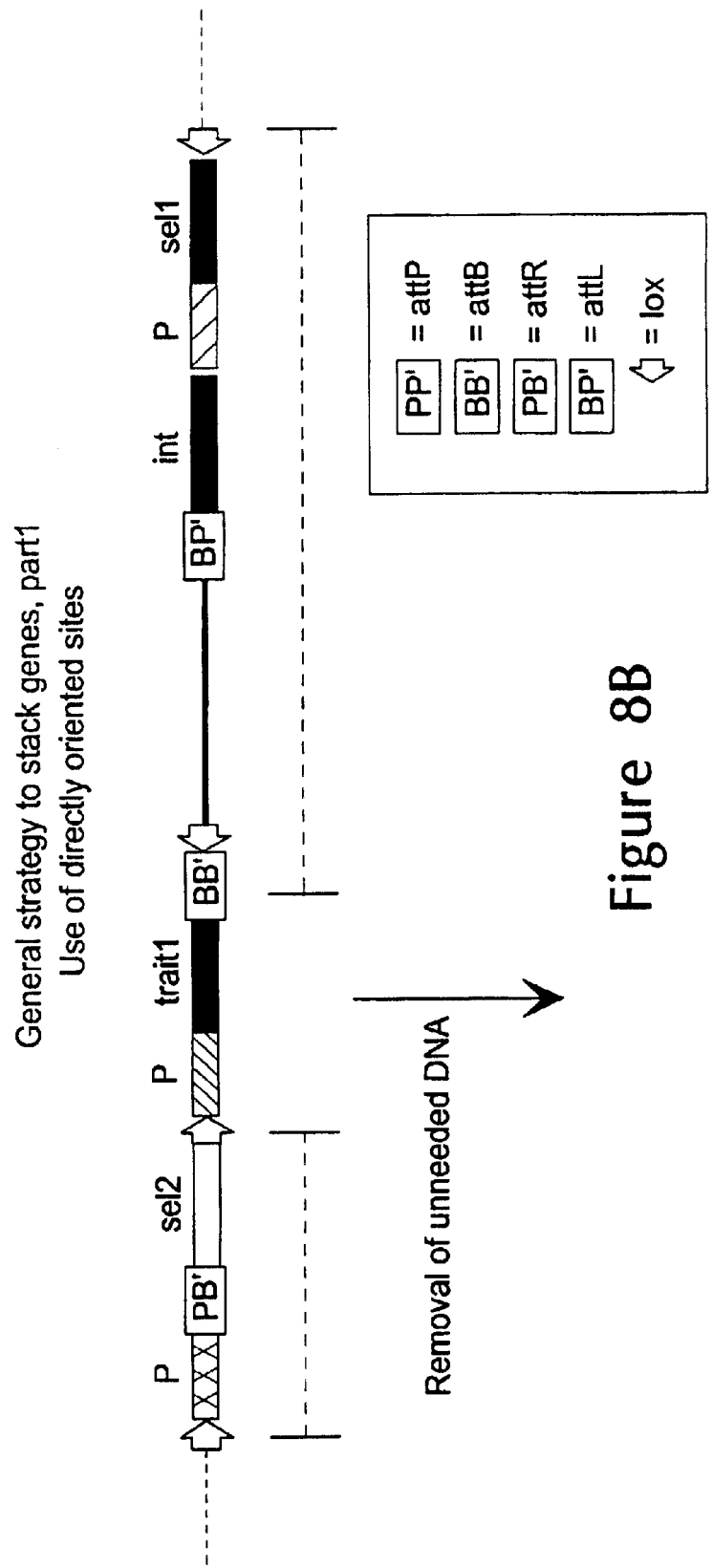
Figure 8C:
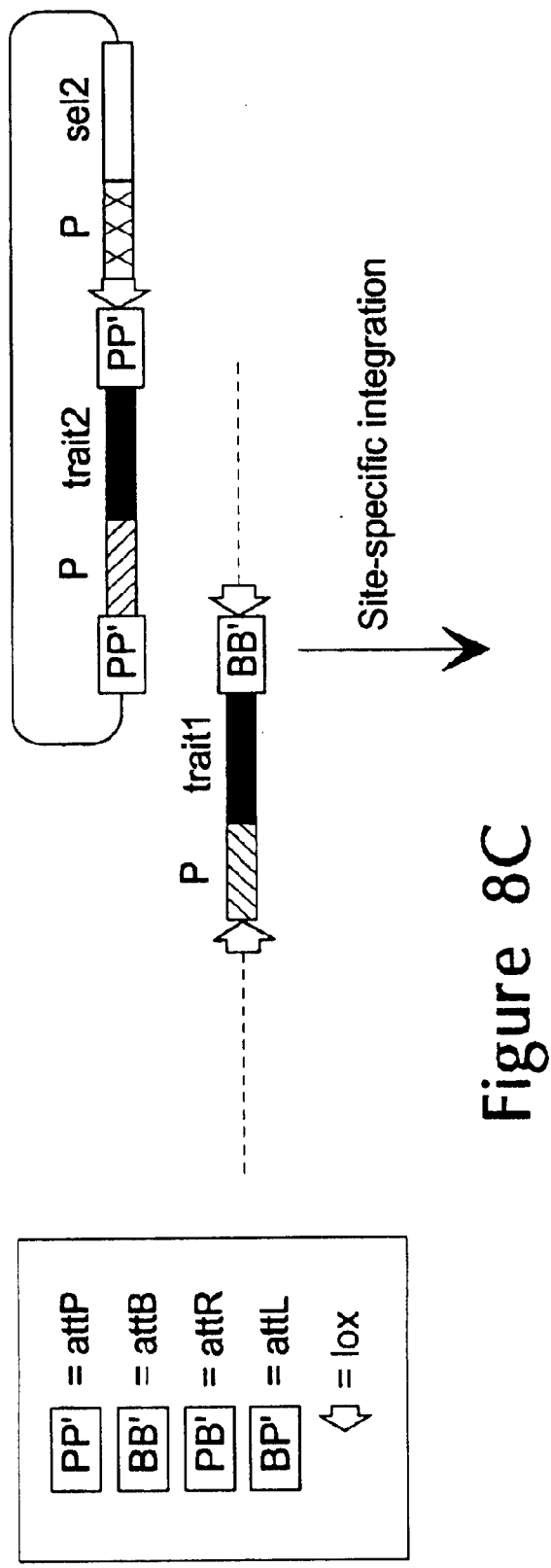

The donor construct is then introduced into the cells that have the receptor construct integrated into their chromosome. Upon contact with the irreversible recombinase (e.g., φC31), recombination between an attB site of the donor construct and the attP site on the receptor construct occurs. (FIGS. 8A–B). Since there are two attB sites present in the donor construct, either site can recombine with the genomic attP site. If the attB site downstream of the polynucleotide of interest recombines with attP, then the resulting integration event will not activate expression of the selectable marker sel2 (not shown). On the other hand, if the attB site upstream of the selectable marker coding region recombines with attP, then the promoter that is present adjacent to the attP site in the receptor construct will become operably linked to the selectable marker coding region (FIG. 8B). This allows one to select for this latter class of integration events. The resulting structure has the polynucleotide of interest and associated attB site between two DNA fragments that are not needed for function of the trait gene. These extraneous fragments can thus be removed by recombinase-mediated deletion of the DNA bracketed by directly oriented RRS (e.g. lox) sites (FIG. 8B–C).

Figure 8D:
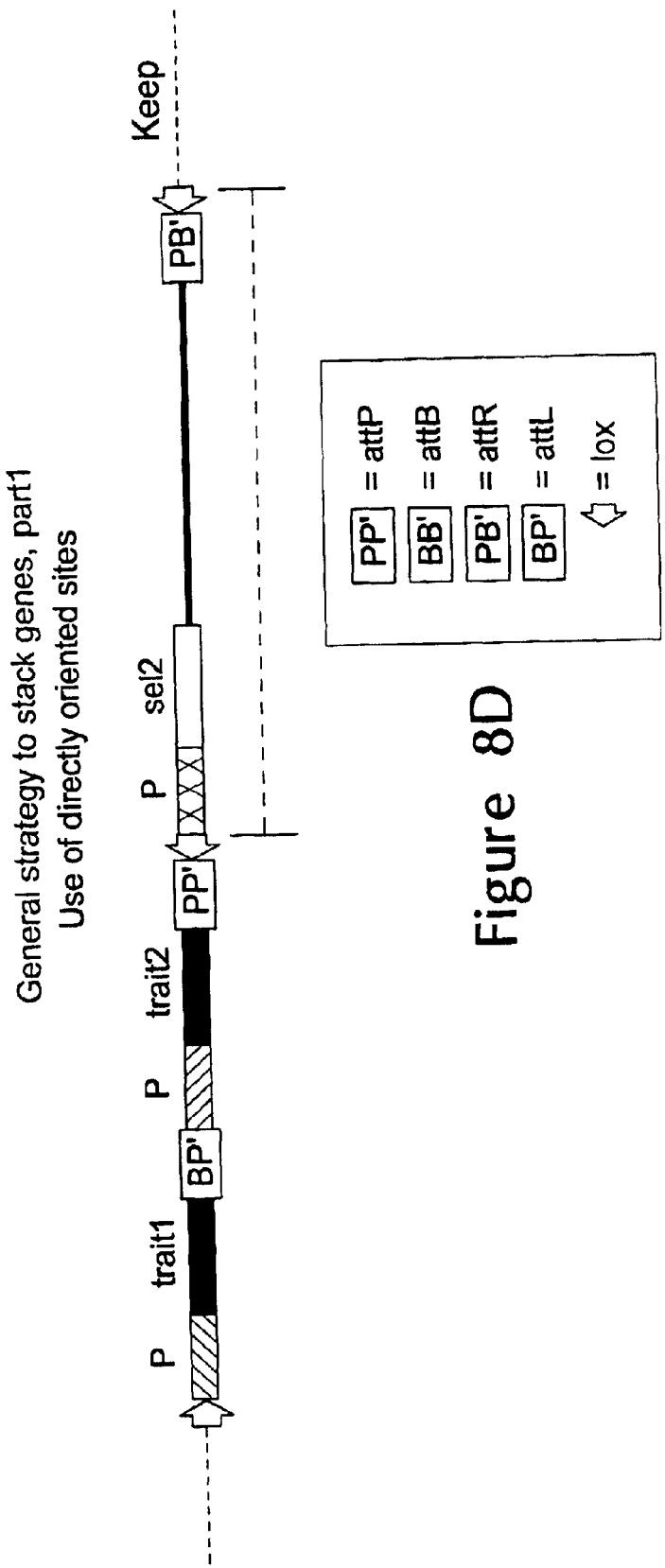
Figure 8E:
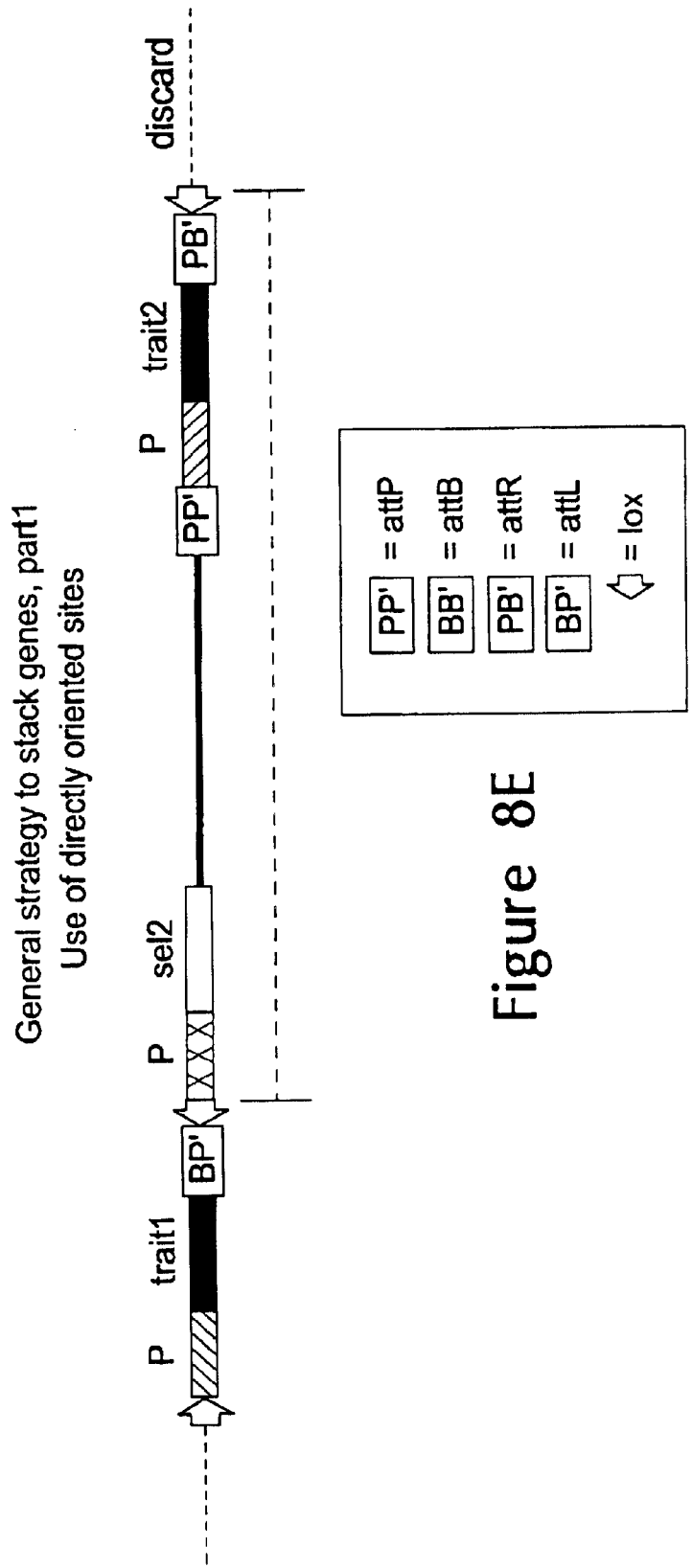

After removal of the extraneous fragments, the host cell retains only the desired polynucleotide and a CIRS (e.g., attB), flanked by an oppositely oriented pair of RRS (e.g., lox). The attB site can thus be used as a target for a second round of recombination with a second donor construct that contains a second gene of interest (FIG. 8C–E). Because both selectable markers have been excised from the chromosome, either one of the same two markers can be used for this second recombination. The integration and excision reactions are repeated as desired using the second, third, and subsequent integrating constructs. (FIGS. 8D–J). This results in the series of polynucleotides adjacent to each other. Gene stacking can also be accomplished using irreversible recombination sites that are in an inverted orientation. An example of this strategy is diagrammed in FIGS. 9A–J.

Typically, the receptor and donor constructs and other constructs to be introduced into the eukaryotic cells are prepared using recombinant expression techniques. Recombinant expression techniques involve the construction of recombinant nucleic acids and the expression of genes in transfected cells. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, used to transfect cells or incorporated into *Agrobacterium tumefaciens* to infect and transform plants. Where *Agrobacterium* is the means of transformation, shuttle vectors are constructed. Cloning in *Streptomyces* or *Bacillus* is also possible.

As described above, selectable markers are often incorporated into the polynucleotide constructs and/or into the vectors that are used to introduce the constructs into the eukaryotic cells. These markers permit the selection of colonies of cells containing the polynucleotide of interest. Often, the vector donor construct will have one selectable marker that is functional in, e.g., *E. coli*, or other cells in which the vector is replicated prior to being introduced into the target cell. A second selectable marker can also be included in the integrating construct; however, if removal of the selectable marker is desired the marker is placed outside the pair of recombination sites that flank the polynucleotide of interest.

Examples of selectable markers for *E. coli* include: genes specifying resistance to antibiotics, i.e., ampicillin, tetracycline, kanamycin, erythromycin, or genes conferring other types of selectable enzymatic activities such as β-galactosidase, or the lactose operon. Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg, 1981 Proc. Nat'l. Acad. Sci. USA, 78: 2072; Southern & Berg, 1982 J. Mol. Appl. Genet., 1:327).

Selection markers for plant cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al., 1982 Gene, 19:327); the hpt gene, which codes for the enzyme hygromycin phosphotransferase and confers resistance to the antibiotic hygromycin (Gritz and Davies, 1983 Gene, 25:179); and the bar gene (EP 242236) that codes for phosphinothricin acetyl transferase which confers resistance to the herbicidal compounds phosphinothricin and bialaphos.

If more than one gene of interest is to be introduced into a eukaryotic cell, it is generally desirable to use a different selectable marker on each exogenous nucleic acid. This allows one to simultaneously select for cells that contain both of the desired exogenous nucleic acids.

The above-described compositions and methods can be used to stably integrate a polynucleotide into any eukaryotic cell. Non-limiting examples of the eukaryotic cells of the present invention include cells from animals, plants, fungi, bacteria and other microorganisms. In one embodiment, the eukaryotic cell is a mammalian cell. Examples of site-specific replacement methods that can be used in a mammalian cell are found in FIGS. 4 and 5. In another embodiment, the eukaryotic cell is a plant cell. An example of a site-specific replacement method that can be used in a plant cell is found in FIGS. 6. In some embodiments, the cells are part of a multicellular organism, e.g., a transgenic plant or animal. The methods of the invention are particularly useful in situations where transgenic materials are difficult to obtain, such as with transgenic wheat, corn, and animals. In these situations, finding the rare single copy insertion requires the prior attainment of a large number of independently derived transgenic clones, which itself requires great expenditure of effort. Among the plant targets of particular interest are monocots, including, for example, rice, corn, wheat, rye, barley, bananas, palms, lilies, orchids, and sedges. Dicots are also suitable targets, including, for example, tobacco, apples, potatoes, beets, carrots, willows, elms, maples, roses, buttercups, petunias, phloxes, violets and sunflowers.

Accordingly, the present invention additionally includes methods of producing a transgenic plant, including the steps of: 1) providing a receptor plant comprising a chromosomal receptor polynucleotide flanked by two IRS; 2) providing a donor plant comprising a chromosomal donor polynucleotide flanked by two CIRS; and 3) crossing the donor plant to the receptor plant to produce a transgenic plant, wherein either the donor plant or the receptor plant contains an irreversible recombinase polypeptide. The donor and receptor plants can be of the same or different genus or species. One embodiment of this aspect of the present invention is shown in FIG. 12.

The transgenic plant produced by this method expresses an irreversible recombinase polypeptide that catalyzes recombination between the IRS and the CIRS and replacement of the receptor polynucleotide with the donor polynucleotide, thereby forming a chromosomal replacement construct in the transgenic plant. In a preferred embodiment, the receptor plant is a single copy receptor line. In further embodiments, the progeny of the transgenic plant that do not express the irreversible recombinase polypeptide are selected. In other preferred embodiments, the chromosomal replacement construct comprises a promoter operably linked to the donor polynucleotide, and more preferably, the promoter is derived from the receptor construct. The present invention also includes crossing the above-described transgenic plant with a plant comprising a nucleic acid encoding a reversible recombinase wherein the chromosomal replacement construct further comprises one or more pairs of directly oriented reversible recombination sites (RRS) that are compatible with the reversible recombinase. (See FIGS. 12B, and C).

The polynucleotide constructs that include recombination sites and/or recombinase-encoding genes can be introduced into the target cells and/or organisms by any of the several means known to those of skill in the art. For instance, the DNA constructs can be introduced into plant cells, either in culture or in the organs of a plant by a variety of conventional techniques. For example, the DNA constructs can be introduced directly to plant cells using biolistic methods, such as DNA particle bombardment, or the DNA construct can be introduced using techniques such as electroporation and microinjection of plant cell protoplasts. Particle-mediated transformation techniques (also known as "biolistics") are described in Klein et al., 1987 Nature, 327:70–73; Vasil, V. et al., 1993 Bio/Technol., 11:1553–1558; and Becker, D. et al., 1994 Plant J., 5:299–307. These methods involve penetration of cells by small particles with the nucleic acid either within the matrix of small beads or particles, or on the surface. The biolistic PDS-1000 Gene Gun (Biorad, Hercules, Calif.) uses helium pressure to accelerate DNA-coated gold or tungsten microcarriers toward target cells. The process is applicable to a wide range of tissues and cells from organisms, including plants, bacteria, fungi, algae, intact animal tissues, tissue culture cells, and animal embryos. One can employ electronic pulse delivery, which is essentially a mild electroporation format for live tissues in animals and patients. Zhao, 1995 Advanced Drug Delivery Reviews, 17:257–262.

Other transformation methods are also known to those of skill in the art. Microinjection techniques are known in the art and well described in the scientific and patent literature. The introduction of DNA constructs using polyethylene glycol (PEG) precipitation is described in Paszkowski et al., EMBO J. 3:2717 (1984). Electroporation techniques are described in Fromm et al., Proc. Natl. Acad. Sci. USA, 82:5824 (1985). PEG-mediated transformation and electroporation of plant protoplasts are also discussed in Lazzeri, P., Methods Mol. Biol. 49:95–106 (1995). Methods are known for introduction and expression of heterologous genes in both monocot and dicot plants. See, e.g., U.S. Pat. Nos. 5,633,446, 5,317,096, 5,689,052, 5,159,135, and 5,679,558; Weising et al., 1988 Ann. Rev. Genet., 22:421–477. Transformation of monocots in particular can be achieved using various techniques including electroporation (e.g., Shimamoto et al., Nature (1992), 338:274–276; biolistics (e.g., European Patent Application 270,356); and Agrobacterium (e.g., Bytebier et al., Proc. Nat'l Acad. Sci. USA (1987) 84:5345–5349).

For transformation of plants, DNA constructs may be combined with suitable T-DNA flanking regions and introduced into a conventional Agrobacterium tumefaciens host vector. The virulence functions of the A. tumefaciens host will direct the insertion of a transgene and adjacent marker gene(s) (if present) into the plant cell DNA when the cell is infected by the bacteria. Agrobacterium tumefaciens-meditated transformation techniques are well described in the scientific literature. See, for example, Horsch et al., Science, 233:496–498 (1984), Fraley et al., Proc. Natl. Acad. Sci. USA, 80:4803 (1983), and Hooykaas, Plant Mol. Biol., 13:327–336 (1989), Bechtold et al., Comptes Rendus De L Academie Des Sciences Serie Iii-Sciences De La Vie-Life Sciences, 316:1194-1199 (1993), Valvekens et al., Proc. Natl. Acad. Sci. USA, 85:5536–5540 (1988). For a review of gene transfer methods for plant and cell cultures, see, Fisk et al., Scientia Horticulturae 55:5–36 (1993) and Potrykus, CIBA Found. Symp. 154:198 (1990).

Other methods for delivery of polynucleotide sequences into cells include, for example, liposome-based gene delivery (Debs and Zhu (1993) WO 93/24640; Mannino and Gould-Fogerite (1988) Bio Techniques 6(7): 682–691; Rose U.S. Pat No. 5,279,833; Brigham (1991) WO 91/06309; and Felgner et al., (1987) Proc. Natl. Acad. Sci. USA 84: 7413–7414), as well as use of viral vectors such as papillomaviral, retroviral and adeno-associated viral vectors (e.g., Berns et al., (1995) Ann. NY Acad. Sci. 772: 95–104; Ali et al., (1994) Gene Ther. 1: 367–384; and Haddada et al., (1995) Curr. Top. Microbiol. Immunol. 199 ( Pt 3): 297–306 for review; Buchscher et al., (1992) J. Virol. 66(5) 2731–2739; Johann et al., (1992 J. Virol 66 (5):1635–1640 (1992); Sommerfelt et al., (1990) Virol 176:58–59; Wilson et al (1989) J. Virol. 63:2374–2378; Miller et al., J. Virol. 65:2220–2224 (1991); Wong-Staal et al., PCT/US94/05700, and Rosenburg and Fauci (1993) in Fundamental Immunology, Third Edition Paul (ed) Raven Press, Ltd., New York and the references therein; Yu et al., Gene Therapy (1994) supra.); West et al., (1987) Virology 160:38–47; Carter et al., (1989) U.S. Pat. No. 4,797,368; Carter et al., WO 93/24641 (1993); Kotin (1994) Human Gene Therapy 5:793–801; Muzyczka (1994) J. Clin. Invst. 94:1351 and Samulski (supra) for an overview of AAV vectors; Lebkowski, U.S. Pat. No. 5,173,414; Tratschin et al., (1985) *Mol. Cell. Biol.* 5(11):3251–3260; Tratschin et al., (1984) *Mol. Cell. Biol.,* 4:2072–2081; Hermonat and Muzyczka (1984) *Proc. Natl. Acad. Sci. USA,* 81:6466–6470; McLaughlin et al., (1988) and Samulski et al., (1989) *J. Virol.,* 63:03822–3828).

Methods by which one can analyze the integration pattern of the introduced donor polynucleotide are well known to those of skill in the art. For example, one can extract DNA from the transformed cells, digest the DNA with one or more restriction enzymes, and hybridize to a labeled fragment of the polynucleotide construct. The inserted sequence can also be identified using the polymerase chain reaction (PCR). (See, e.g., Sambrook et al., *Molecular Cloning—A Laboratory Manual,* Cold Spring Harbor Laboratory, Cold Spring Harbor, N.Y., 1989 for descriptions of these and other suitable methods).

Transformed plant cells, derived by any of the above transformation techniques, can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture,* pp. 124–176, Macmillian Publishing Company, New York (1983); and in Binding, *Regeneration of Plants, Plant Protoplasts,* pp. 21–73, CRC Press, Boca Raton, (1985). Regeneration can also be obtained from plant callus, explants, somatic embryos (Dandekar et al., *J. Tissue Cult. Meth.,* 12:145 (1989); McGranahan et al., *Plant Cell Rep.,* 8:512 (1990)), organs, or parts thereof. Such regeneration techniques are described generally in Klee et al., *Ann. Rev. of Plant Phys.,* 38:467–486 (1987).

The methods are also useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals,* VCH Publ., 1993; Murphy and Carter, Eds., *Transgenesis Techniques: Principles and Protocols* (*Methods in Molecular Biology,* Vol. 18), 1993; and Pinkert, Calif., Ed., *Transgenic Animal Technology: A Laboratory Handbook,* Academic Press, 1994. Transgenic fish having specific genetic modifications can also be made using the claimed methods. See, e.g., Iyengar et al., (1996) *Transgenic Res.* 5: 147–166 for general methods of making transgenic fish.

One method of obtaining a transgenic or chimeric animal having specific modifications in its genome is to contact fertilized oocytes with a vector that includes the polynucleotide of interest flanked by recombination sites. For some animals such as mice, fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16–150 cells. The 16–32 cell stage of an embryo is described as a morula. Pre-implantation embryos containing more than 32 cells are termed blastocysts. These embryos show the development of a blastocoel cavity, typically at the 64 cell stage. If desired, the presence of a desired exogenous polynucleotide in the embryo cells can be detected by methods known to those of skill in the art. Methods for culturing fertilized oocytes to the pre-implantation stage are described by Gordon et al., (1984) *Methods Enzymol.* 101: 414; Hogan et al., *Manipulation of the Mouse Embryo: A Laboratory Manual,* C.S.H.L. N.Y. (1986) (mouse embryo); Hammer et al., (1985) *Nature* 315: 680 (rabbit and porcine embryos); Gandolfi et al., (1987) *J. Reprod. Fert.* 81: 23–28; Rexroad et al., (1988) *J. Anim. Sci.* 66: 947–953 (ovine embryos) and Eyestone et al., (1989) *J. Reprod. Fert.* 85: 715–720; Camous et al., (1984) *J. Reprod. Fert.* 72: 779–785; and Heyman et al., (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the methods can be used to obtain embryonic stem cells (ES) that have a single copy of the desired donor polynucleotide. These cells are obtained from pre-implantation embryos cultured in vitro. See, e.g., Hooper, M L, *Embryonal Stem Cells: Introducing Planned Changes into the Animal Germline* (Modern Genetics, v. 1), Int'l. Pub. Distrib., Inc., 1993; Bradley et al., (1984) *Nature* 309, 255–258. Transformed ES cells are combined with blastocysts from a non-human animal. The ES cells colonize the embryo, and in some embryos, form the germ line of the resulting chimeric animal. See Jaenisch, *Science,* 240: 1468–1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al., (1997) *Nature* 385: 810–813.

As described generally described above, the invention provides several strategies by which to achieve desired site-specific recombination. These strategies include, for example, methods for obtaining replacement of a chromosomal polynucleotide with a second polynucleotide. In some embodiments, the polynucleotide of interest is introduced into the cellular genome in the absence of undesired DNA, such as a selectable marker. Other embodiments provide methods by which undesired DNA such as selectable markers are deleted from the cellular genome after their use to facilitate selection of cells that include the desired polynucleotide of interest. These specific strategies are described further in the Examples below.

Throughout this application, various publications are referenced. The disclosures of all of these publications and those references cited within those publications in their entireties are hereby incorporated by reference into this application in order to more fully describe the state of the art to which this invention pertains. It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein,

EXAMPLES

Example 1

Gene Replacement Using Linear or Circular Targeting Constructs

This Example demonstrates that the *Streptomyces* bacteriophage φC31 site-specific recombination system functions in a gene replacement strategy in eukaryotic cells. The strategy makes use of a site-specific integration system, such as the system derived from bacteriophage φC31. Insertion of the circular phage DNA chromosome into the bacterial genome requires a single polypeptide φC31 protein, the integrase, encoded by int, that recombines the bacterial and phage attachment sites attB and attP, respectively, to form new hybrid sequences known as attL and attR. The attB and attP sites share only 16 base pair matches within a 53 bp stretch centered at the point of crossover. Here, the designations BB', PP', BP' and PB', will be used interchangeably for attB, attP, attL and attR, respectively. Inverse orientations of attB, attP, attL and attR are designated as B'B, P'P, P'B and B'P, respectively.

Materials and Methods

Recombinant DNA

Standard methods were used throughout. *E. coli* strain XL2-Blue (recA1 endA1 gyrA96 thi-1 hsdR17 supE44 relA1 lac [F' proAB lacI q ZΔM15Tn10 (Tet$^r$) Amy Cam$^r$, Strategene) served as host for DNA constructs.

Media

Fission yeast strains were grown on minimal medium (EMM-low glucose, from Bio101) supplemented as needed with 225 mg/l adenine, histidine, leucine or uracil. Minimal plates with 5-FOA (5-floroorotic acid, from Zymo Research, Inc.) were prepared according to Grimm et al. ((1988) Mol. Gen. Genet. 215: 81–86) and were supplemented with adenine, histidine, and leucine. When used, thiamine was added to 5 μg/ml.

*S. pombe* with Two φC31 attP Targets

The 84 bp φC31 attP site (abbreviated as PP'), isolated as an ApaI-SacI fragment from pHS282 (Thorpe & Smith (1998) Proc. Nat'l. Acad. Sci. USA 95:5505–5510) was cloned into the same sites of the *S. pombe* integrating vector pJK148 (Keeney & Boeke (1994) Genetics 136:849–856) to make pLT44. This plasmid was targeted to the *S. pombe* leu1-32 allele by lithium acetate mediated transformation with NdeI cut DNA. The recipient host FY527 (h- ade6-M216 his3-D1 leu1-32 ura4-D18), converted to Leu+ by homologous recombination with pLT44, was examined by Southern analysis. One Leu+ transformant, designated FY527attP (FIG. 3A), was found to contain a single copy of pLT44. Another transformant, designated FY527attP×2 (FIG. 3B), harbors a tandem insertion of pLT44, and therefore contains two attP sites.

Integrative ura4+ Vector Containing Two φC31 attB Sites

The *S. pombe* ura4$^+$ gene, excised from pTZura4 (S. Forsburg) on a 1.8 kb EcoRI-BamHI fragment, was inserted into pJK148 cut with the same enzymes to create pLT40. The φC31 attB site (abbreviated as BB'), isolated from pHS21 as a 500 bp BamHI-XbaI fragment, was ligated into pLT40 cut with those enzymes, creating pLT42. Most of the leu1 gene was removed from pLT42 by deleting a XhoI fragment to create pLT45. This left 229 bp of leu1 in pLT45 and reduced its transformation efficiency to that of a plasmid without any leu1 homology. pLT50, which has a second attB site in the same orientation immediately on the other side of ura4, was constructed by first subcloning the attB BamHI-SacI fragment from pLT42 into pUC19, excising it with EcoRI and SalII, and subsequently inserting it into pLT45 cut with EcoRI and XhoI. The second attB site in the final construct was sequenced once on each strand and found to be identical to the first attB site.

Linear DNA Transformation

The attB-ura4$^+$-attB linear DNA was prepared as an AttII-AlwNI fragment purified from pLT50, or as a PCR product using pLT50 as template. PCR was conducted using standard conditions with a T3 primer and a second primer (5' ggc cct gaa att gtt gct tct gcc 3'; SEQ ID NO: 1) corresponding to the plasmid backbone of pJK148.

Repressible Synthesis of φC31 Integrase

The *S. pombe* Pmnt promoter, repressible by vitamin B1, was excised as a 1.2 kb PstI-SacI fragment from pMO147 and inserted into the his3+, ars1 vector pBG2 (Ohi et al., (1996) Gene 174: 315–318) cut with the same enzymes, creating pLT41. A 2.0 kb SacI fragment containing the φC31 int coding region was transferred from pHS33 (Thorpe & Smith (1998) supra.) to the SacI site of pLT41. A clone in which the int coding region was oriented such that expression is under the control of Pmnt was designated pLT43.

Molecular Analyses

Southern analysis was performed using the Genius system from Boehringer Mannheim. A 998 bp internal EcoRV fragment of leu1, a 1.8 kb fragment of ura4, and the 2.0 kb φC31 int gene were digoxigen-labeled by the random primer method and used as probes. Polymerase chain reaction was performed on a Perkin Elmer Cetus Gene Amp PCR 9600 using Stratagene Turbo PFU enzyme or VENT polymerase. The standard T3 and T7 primers were used where possible. The ura4 primer (5' gtc aaa aag ttt cgt caa tat cac 3' (SEQ ID NO: 2)) and the pJK148 primers were purchased from Operon Technologies. For all PCR reactions an annealing temperature of 51° C. and a 30-second extension time were used.

Results and Discussion

Gene Replacement via Linear DNA

Figure 2A:
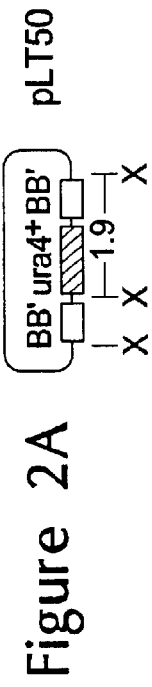
FIGS. 2A–G show a dual-site recombination strategy at the S. pombe leu1 locus. The linear attB-ura4$^+$-attB DNA, derived from pLT50 (FIGS. 2A–B) recombines on both ends of the molecule resulting in a precise gene replacement (FIG. 2C, class 1). Additionally, some side reactions were observed, where the linear molecule recircularized by homologous recombination to form a circular intermediate (FIG. 2D) prior to insertion into either the 5' attP (FIG. 2E, class 2) or the 3' attP site (FIG. 2F, class 3) of the target locus. When circular pLT50 was used as a transformation substrate, one clone was recovered where a single recombination between the 5'attB site of pLT50 and the 5'attP site of leu1 locus produces the structure shown (FIG. 2G, class 4). Predicted sizes of endonuclease XbaI (X) or NdeI (N) cleavage products are shown.
Figure 2B:
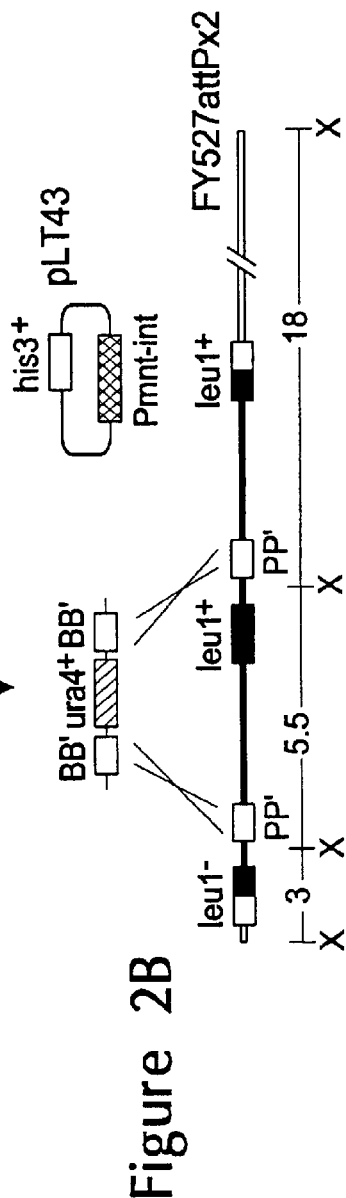

This experiment demonstrates that the φC31 site-specific recombination system is an efficient means to deliver linear cDNAs into a target cell. To prepare cDNA substrates, the linear molecules would be linked by ligation or PCR synthesis attachment sites on both ends, followed by recombination with a tandem pair of chromosomally situated target sites, and replacement of the target DNA with the inserting cDNA. To test whether such a gene replacement reaction is efficient, an FY527 derivative bearing a tandem insertion of pLT44 was isolated. This strain, designated FY527attP×2, has two attP sites in direct orientation at the leu1 locus, separated by a leu1 gene and vector sequences (FIG. 2B). FY527attP×2 was transformed with linear DNA containing ura4$^+$ flanked by attB sites. The linear substrate was obtained either as a gel-purified fragment from pLT50 (FIG. 2A) or as a PCR product from amplification of this plasmid. The plasmid pLT50, derived from pLT45, has a second directly oriented attB site on the other side of the ura4$^+$ gene. Both linear substrates gave approximately the same transformation efficiency when co-transformed with pLT43, which stimulated the number of Ura+ transformants (Table 1). In some experiments, the frequency was as high as that of the replicating plasmid control.

Figure 2C:
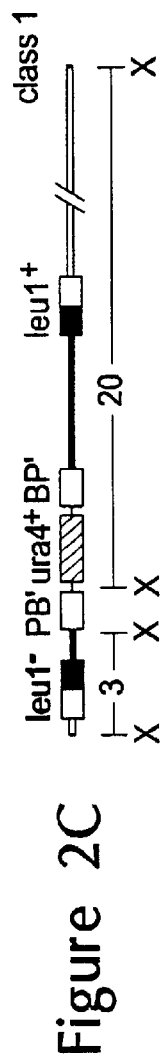
Figure 2D:
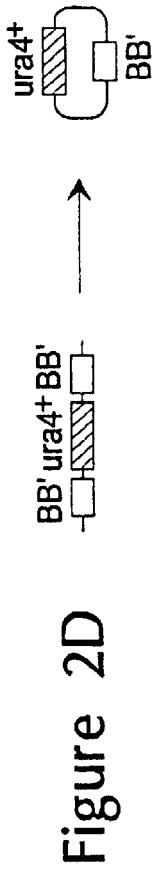
Figure 2E:
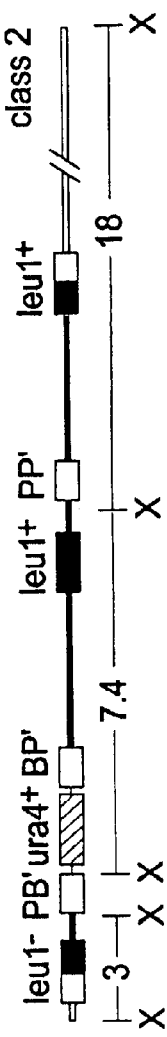
Figure 2F:
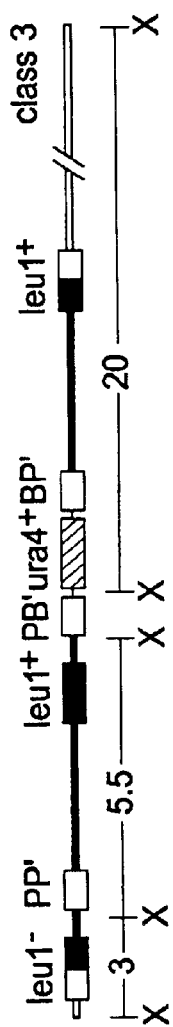
Figure 2G:
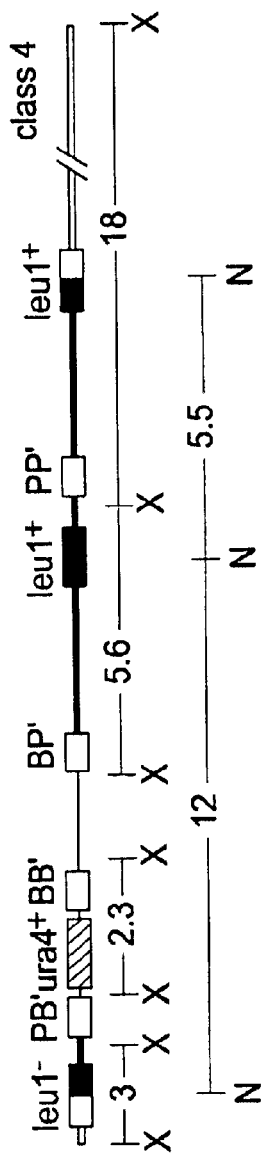

The intended gene replacement event, with recombination occurring between two 5' sites and two 3' sites, is diagrammed in FIG. 2B. Although the two crossovers may happen sequentially rather than concurrently, the end product is the same (FIG. 2C, class 1). When the XbaI restriction pattern of eight representative Ura⁺ His⁻ clones was examined, seven showed patterns that fell into three classes. Three of them had the class 1 pattern, in which the leu1 probe hybridized to bands of 3 kb and 20 kb, and the ura4 probe hybridized to a 20 kb band (FIG. 2C). The second and third classes represent events that appear to result from prior circularization of the linear fragment before site-specific insertion into an attP target. FIG. 2D depicts the circularization reaction that would result from recombination between the duplicated attB sites. Integration of the circle into the 5' attP site increases the size of the 5.5 kb plasmid band to 7.4 kb; this band would hybridize with both the ura4 and leu1 probes (FIG. 2E, class 2). This pattern was found in one transformant. Integration into the 3' attP site increased the 18 kb band to 20 kb, and allowed its detection by both probes (FIG. 2F, class 3). This pattern was found in three transformants. The remaining clone had two copies of ura4 and an additional copy of leu1, suggesting gene amplification at the leu1 locus. It was not analyzed further.

occurs at the attB site, double stranded breaks may then recruit the generalized homologous recombination system. However, such recombination was not detected in in vitro studies with purified components (Thorpe, H. M. & Smith, M. C. M. (1998) Proc. Natl. Acad. Sci. USA 95: 5505–5510). Alternatively, the endogenous *S. pombe* recombination genes could promote this plasmid rearrangement. Reducing the homology between the direct repeats on the plasmid to a minimum, 34 bp for attB and 39 bp for attP (Groth et al., (2000) Proc. Natl. Acad. Sci. USA 97: 5995–6000), may reduce the frequency of this unwanted side reaction.

In addition to these three classes of integration structures, there exists the possibility of integration patterns resulting from incomplete recombination of attB×attP sites. This could occur if the amount of integrase protein is limiting, as it could be if pLT43 were lost from the cell. If the His⁺ phenotype is not selected for, His- colonies are readily found. Four possible structures could arise from a single

TABLE 1

Integrase-dependent gene replacement in *S. pombe* FY527attPx2

| DNA (1 μg) | Selection | Transformants per $10^7$ cells (± sd)* | Relative Value$ | Class 1 | Class 2 | Class 3 | Other |
|---|---|---|---|---|---|---|---|
| pLT43 | His⁺ | 4106 (± 331) | 100 | | | | |
| Linear fragment | Ura⁺ | 19 (± 27) | 0.46 | | | | |
| Linear fragment and pLT43 | Ura⁺ | 1568 (± 495) | 38 | 38%† | 12%† | 38%† | 12%† |
| pLT50 | Ura⁺ | 63 (± 52) | 1.5 | | | | |
| pLT50 and pLT43 | Ura⁺ | 2560 (± 919) | 62 | 38%† | 12%† | 25%† | 25%† |
| pLT45 | Ura⁺ | 66 (± 46) | 1.6 | | | | |
| pLT45 and pLT43 | Ura⁺ | 683 (± 298) | 17 | | | | |

*From 3 independent experiments
$(transformation efficiency of the DNA of interest)/(transformation efficiency of pLT43) × 100
†n = 8

Gene Replacement via Circular DNA

The class 2 and 3 structures recovered from linear DNA transformation suggest a circular intermediate. Yet the linear fragment does not have complementary single-stranded ends that could readily anneal. The molecular structure is consistent with either intramolecular recombination between the attB sites, or some sort of ligation between the two ends. Perhaps the high rate of circularization was promoted by linear DNA ends. Linear ends may be more proficient at strand invasion or end joining, since double-strand breaks stimulate recombination in yeast (Szostak et al., (1983) Cell 33: 25–35). If this were true, class 2 and 3 integrants would be minimized by the use of circular DNA.

The transformation of FY527attPx2 was tested with pLT50 plasmid DNA (see Table 1). The integration structures of eight representative Ura⁺ His⁻ clones from this transformation were analyzed. Six of the eight clones fell into the same three classes: three are in class 1, one in class 2, and two in class 3. The prevalence of class 2 and 3 integrants demonstrates that recombination between the duplicated attB sites does not require a linear substrate. It remains to be determined whether this event was promoted by *S. pombe* or by the φC31 integrase. One possibility is that the integrase interacts with attB even without the presence of attP. The φC31 integrase is a member of the invertase-resolvase class of enzymes that catalyzes recombination by making double-strand breaks in each DNA substrate. If this recombination event between the four sites: 5'attB×5'attP, 3'attB×3'attB, 3'attB×5'attP and 5'attB×3'attP. If followed by a second attB×attP reaction, the 5'attB×5'attP and the 3'attB×3'attB integrants would be converted to the class 1 structure, and the 3'attB×5'attP and 5'attB×3'attP integrants would not be found, as the ura4⁺ marker would be deleted. One of the eight isolates gave a pattern consistent with the incorporation of intact pLT50 through a 5'attB×5'attP reaction. This class 4 structure is shown in FIG. 1G. The ura4 probe detected a single 2.3 kb band, and the leu1 probe detected bands of 3 kb, 5.6 kb and 18 kb. Cleavage with NdeI gave a 12 kb band that hybridized to both the leu1 and ura4 probes, consistent with physical linkage of the two markers. The remaining isolate had also incorporated the entire plasmid but had gained additional bands hybridizing to both leu1 and ura4. This represents a more complex event, perhaps indicating gene amplification at the locus.

Figure 3A:
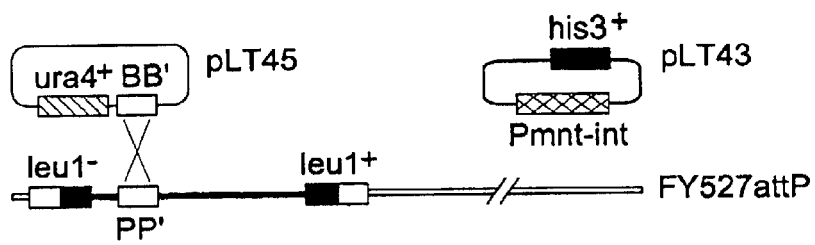
FIG. 3 shows transformation efficiency as a function of integrase-DNA concentration (panel C). FY529attP (panel A) or FY529attP×2 (panel B) was transformed with 1 μg of pLT45 or pLT50 DNA, respectively, along with various amounts of pLT43 DNA.
Figure 3B:
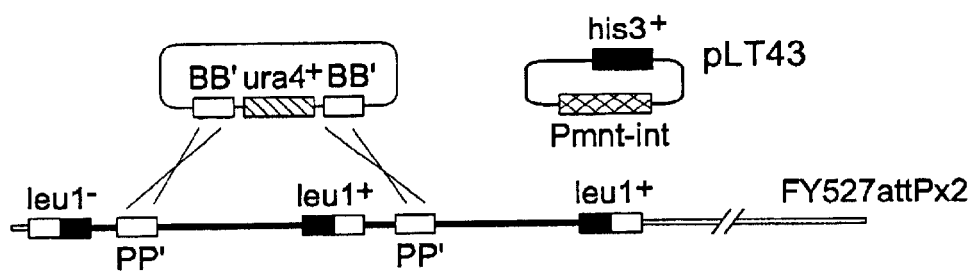

Integration into the FY527attPx2 strain was also examined using intact pLT45 (FIG. 3A), which can insert into the chromosome at either the 5'attP or the 3'attP site. The additional attP target in the chromosome did not significantly change the transformation efficiency. When normalized to the number of His⁺ transformants obtained with pLT43, the efficiency of φC31 integrase mediated transformation of FY527attPx2 is comparable with the transformation of FY527attP with pLT45. Thus duplicated sites in both the target and donor molecules appear necessary for the increased transformation frequency observed with the gene replacement strategy.
Determining the Optimal Concentration of Integrase DNA Transformations of FY527attP×2 with pLT50 (FIG. 3B) and FY527attP with pLT45 (FIG. 3A) were performed using a range (0, 0.1, 1, 5, 10 mg) of pLT43 DNA concentrations. FIG. 3 shows that both sets of transformations yielded a peak number of Ura+ colonies with 5 mg of pLT43 DNA. The pLT50/FY527attP×2 transformation produced a 4 to 14 fold higher number of transformants compared to the pLT45/FY527attP transformation. This observation is consistent with the results discussed above. However, the higher transformation frequency is offset by the lower frequency of precise events, 38% for pLT50 compared to 88% for pLT45.

Summary

Figure 3C:
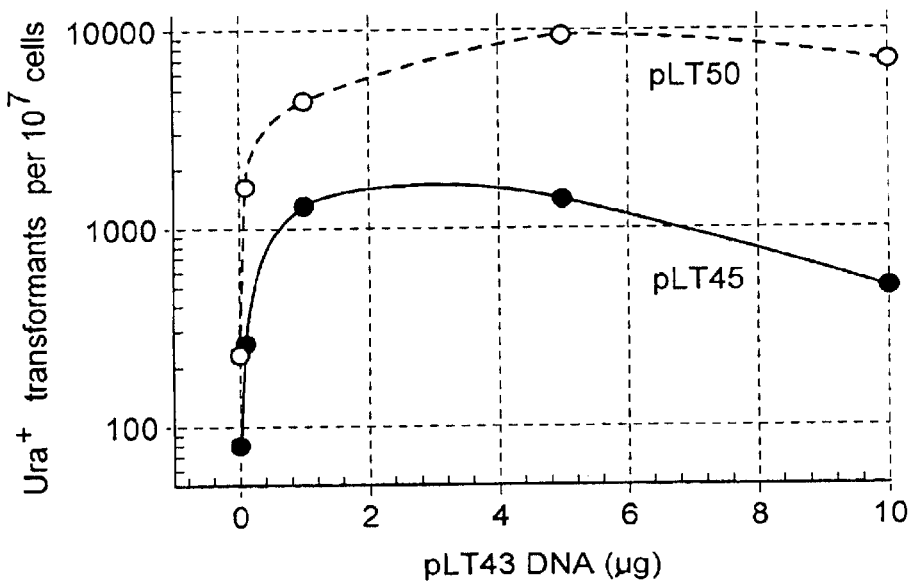

This Example demonstrates that dual-site recombination reactions are quite efficient. The frequency of precise gene replacement events is about 14% to 24% of the transformation efficiency of a replicating plasmid vector (Table 1). FIG. 3C shows that at optimal integrase gene concentration, the transformation efficiency increases still farther to a level approaching that of a replicating plasmid. The high transformation efficiency of replicating plasmids has made it possible to clone by functional selection in bacteria and yeasts. These results demonstrate that cloning by direct selection can also be achieved with the dual site φC31 recombination system. A library of linear cDNA molecules need not be passed through a cloning vector system. Instead, it can be ligated with flanking att sites and introduced directly into a genomic att-att target in animal or plant cells.

Although a competing side reaction consisting of integration of circular molecules derived from the linear DNA was observed, these undesired events can be minimized by using the smallest functional attachment sites. Additionally, if the target site DNA between two attP sites encoded a marker for which a negative selection exists, then only the full replacement of the marker would be detected.

Example 2
Inserting the Coding Region for Expression Behind a Genomic Promoter

This example illustrates a general strategy to deliver a DNA fragment to a designated animal chromosome target by a gene replacement strategy that does not require the co-introduction of a selectable marker. Because a replacement strategy results in the loss of a corresponding fragment of host DNA, the loss of a counter-selectable marker can be the selection criteria for gene replacement. This approach results in the precise integration of a trait gene without incorporating additional unneeded DNA.

This example also illustrates that this method is useful for testing the functional expression of a cDNA molecule through its direct placement behind a genomic promoter resident in the host cell. This bypasses the need for prior cloning of the cDNA into a vector for propagation in E. coli, such as into a plasmid or phage vector. An investigator can choose a gene sequence from the database, make the appropriate primers corresponding to that gene sequence, selectively reverse transcribe the chosen mRNA sequence and amplify its cDNA to sufficient quantity for transformation. A cDNA produced from mRNA can be ligated to synthetic attP or attB sites and used directly for the gene replacement strategy. In this illustration, the attB synthetic oligomers are designed to flank the cDNA in the same orientation.

Methods

The target construct consists of a Pc-attP-tk-Ps-zeo-attP fragment (FIG. 4). Abbreviations used: Pc, the human cytomegalovirus promoter; tk, the thymidine kinase coding region; Ps, the SV40 early promoter; zeo, zeomycin resistance coding region. The attP site in this case is a recombination site belonging to the class of irreversible recombination systems such as the φC31 system. The Ps-zeo fragment permits selection of the target construct in the host genome. The tk gene is a counter-selectable marker. Under appropriate culture conditions, cells that have lost the functional tk gene will thrive while those retaining the functional tk gene will not. The use of alternative selectable markers, counter-selectable markers, and promoters are possible.

The integrating construct consists of a gene fragment, in this case, a cDNA, flanked by a set of attB sites of the same orientation (FIG. 4). If the attP upstream of tk recombines with the attB upstream of the 5' end of the cDNA, and the attB downstream of zeo recombines with attB downstream of the 3' end of the cDNA, then the dual recombination events will remove the tk gene from the genome. This gene replacement will select for the Pc-attR-cDNA linkage, resulting in expression of the cDNA. The other possible pairs of recombination will break the chromosome.

Example 3
Gene Replacement in the Human Genome

This example illustrates a more specific strategy than in Example 2 to deliver a DNA fragment to a designated mammalian chromosome target. Preferably, the mammalian chromosome target is a human chromosome target. This example shows that a cDNA molecule can be inserted site-specifically behind a genomic target promoter for expression in the sense or antisense orientation. As the phenotypes conferred by expression of that cDNA may reveal clues to gene function, this cDNA integration strategy could be a tool for functional genomics analysis.

Methods
Recombinant DNA

Standard cloning methods were used throughout. E. coli strain JM109 [F' traD36 lacIq D(lacZ)M15 proA+B+/e14-(McrA−) D(lac-proAB) thi gyrA96(Nalr) endA1 hsdR7(rk- mk+) relA1 supE44], used for DNA cloning, was grown in Luria Broth.

Control hpt Expression Construct

An hpt fragment, the coding region of the hygromycin resistance gene, was retrieved by SalI cleavage from p35S-hpt (Albert et al., 1995 Plant J. 7:649–59) and subcloned into the SalI site of pBluescriptII KS(+/−). The NotI-KpnI fragment from this plasmid, which contains the hpt gene, was subsequently subcloned into the NotI-KpnI sites of the cDNA expression vector pcDNA3.1/zeo (Invitrogen, Carlsbad, Calif.). The resulting plasmid, pcDNA3.1-hpt, expresses hpt from Pc, the human cytomegalovirus promoter φC31 Integrase Expression Vector pJHK1 (FIG. 5A) has a Pc-int fragment, where int is the φC31 integrase coding region: The vector pcDNA3.1/zeo was cleaved with NsiI and BsmI to remove the fragment comprising most of the zeocin resistance coding region (1,800 bp to 2,767 bp). The remaining vector was recircularized by blunt-end ligation. An 1.9 kb NheI-BamHI fragment containing the φC31 integrase gene was inserted into the NheI-BamHI site of the zeocin-sensitive pcDNA3.1 derivative to generate pJHK1. The NheI proximal end of the φC31 integrase fragment has a synthetic Kozak sequence (5'-GGGCCCGCCACGATGACACAAGGGGTTGTGACC GGGGTGGACAC-GTACGCGGGTGCTTACGACCGTCAGTCGCGCGA GCGCGAGAATTC-3'; SEQ ID NO: 3).

Integration of the hpt Vector Flanked by Oppositely Oriented φC31 attB Sites pJHK2 (FIG. 5C) contains a BB'-hpt-B'B fragment in a pBluescriptII KS(+/−) (Stratagene, La Jolla, Calif.) backbone, where BB' and B'B are the φC31 attB sites in direct and indirect orientations, respectively. The hpt fragment was retrieved by SalI cleavage from p35S-hpt (Albert et al., 1995 supra) and subcloned into the SalI site of pBluescriptII KS(+/) to generate pBluescript-hpt. A 53 bp KpnI-BB'-XhoI oligo (5'-GCGGTGCGGGTGCCAGGGCGTGCCCTTGGGC-TCCCCGGGCGCGTACTCCACCT-3'; SEQ ID NO: 4) was inserted into the corresponding sites in pBluescript-hpt to generate pBluescript-BB'-hpt. The KpnI-BB'-XhoI linker was also subcloned into pMECA (Biotechniques, Vol. 24:6, 922–925, 1998) before retrieving it out as a SpeI-HindIII fragment for insertion into the corresponding sites in pBluescript-BB'-hpt to produce pJHK2.

Genomic Target with tk Flanked by Inverted attP Sites pJHK3 (FIG. 5A) contains a Pc-PP'-tk-P'P fragment in a pcDNA3.1/zeo backbone, where tk is the human herpes simplex virus thymidine kinase coding region, and PP' and P'P are the direct and inverse orientations of the φC31 attP sites, respectively. Two 53 bp φC31 attP sites (5'-AGTAGTGCCCCAACTGGGGTAACCTTTGAGTTCT CTCAGTTGGGGGCGTAGGG-3'SEQ ID NO: 5) were synthesized with appropriate flanking restriction enzyme sites. An EcoRI-HindIII-P'P-AflII oligo was inserted into the corresponding sites in pcDNA3.1/zeo to generate pcDNA3.1-P'P. A 1.85 kb XhoI-HindIII tk fragment from pIC19R/MC1-TK (Dr. Kirk Thomas, University of Utah) was appended to the corresponding sites to generate pcDNA3.1-tk-P'P. The tk gene contains a 147 bp enhancer in its 5' end. An NheI-PP'-XhoI oligo was inserted into the corresponding sites in pcDNA3.1-tk-P'P to form pJHK3.

Target Cell Lines

The pJHK3 construct was transfected into the human cell line 293T (American Type Culture Collection, Rockville, Md.) using lipofectamine™ (Life Technologies, Gaithersburg, Md.) according to the manufacturer's directions. Cells were grown in Dulbecco's Modified Eagle Medium (DMEM) containing 10% fetal calf serum. The pJHK3 construct has a single XhoI site upstream, and a single HindIII site downstream of the tk gene. DNA from 32 stably transfected cell lines was cleaved with either XhoI or HindIII for Southern hybridization with a tk probe. Two cell lines showed a single hybridization band in either XhoI or HindIII cleaved DNA, suggesting a single copy of the integrated molecule. Hybridization to BstEII cleaved DNA, which should cleave at the attP sites, revealed the expected 2 kb internal tk fragment.

Gancyclovir Resistance Analysis

Functional expression of the tk gene was tested with gancyclovir (Sigma Co.) treatment. The cells were seeded in 24-well tissue culture plate (1×10³ cells/well) and grown overnight. Gancyclovir (ranging from 0 to 50 mM) was added to each well, and cell growth was observed for several days. Wild type 293T cells were insensitive to gancyclovir up to the highest concentration tested (50 mM), whereas the two cell lines with the single Pc-PP'-tk-P'P fragment were sensitive to gancyclovir.

φC31 Integrase-mediated Recombination

Four μg of both pJHK1 and pJHK2 were co-transfected into 1×10⁶ 293T cells that harbor a single copy of pJHK3. Three days after transfection, the cells were serially diluted and transferred to fresh DMEM containing 50 mM of hygromycin (Boehringer Mannheim) or gancyclovir. The resistant cells were isolated around 14 days after transfection, and further analyzed. For the transfection with linear DNA, the BB'-hpt-B'B linear fragment was prepared as a KpnI fragment purified from pJHK2.

Molecular Analyses

Genomic DNA was isolated from 293T cells using QIAampR DNA Blood Mini Kit (Qiagen, Valencia, Calif.) according to the manufacturer's manual. Genomic Southern hybridization was performed with standard protocol where DNA probe was made using random primed DNA labeling kit (Cat# 1004760) from Boehringer Mannheim.

Results and Discussion

An mRNA, such as one implicated by comparative genomic or transcript-profiling analysis, can be selectively amplified by PCR using primers with attP ends. As depicted in FIG. 5A, the attP ends were in opposite orientation such that the cDNA can insert into the target in either orientation. The dual recombination reaction would fuse the cDNA behind the target promoter for sense (FIG. 5A) or antisense expression (FIG. 5B), with the expectation that it may lead to hyper or hypo-production of the gene product. Concomitantly, the loss of the counter-selection gene would provide detection for site-specific gene replacement. In the figures that follow, whereas promoters are explicitly indicated, for simplicity, terminators, sequences that promote transcription termination and lie downstream of every coding region, are not shown as separate elements.

Single Copy Target Cell Lines

To create a target site in the human genome for the targeted insertion of a linear DNA fragment, the construct pJHK3, which has a Pc-PP'-tk-P'P fragment within a pcDNA3.1 zeo vector backbone was transfected into the human cell line 293T. Expression of the tk gene conferred sensitivity to the nucleoside analog gancyclovir. As the vector backbone contains a zeocin resistance gene, zeocin resistant colonies resulting from random integration of pJHK3 were purified and analyzed by Southern hybridization.

Molecular Analysis of Target Cell Lines

Genomic DNA from 32 cell lines were treated with XhoI or HindIII and probed with tk DNA. XhoI or HindIII cuts once upstream or downstream of tk, respectively. Hybridization to the tk probe should reveal the transgene-host DNA border fragments on both sides of the pJHK3 insertion. A single hybridization band detected in XhoI and HindIII treated DNA would indicate a single inserted copy of pJHK3. Two cell lines, JHK3a and JHK3b, met this expectation. The fragment size of the XhoI or HindIII was not predicted as it depends on the position of nearest XhoI or HindIII host cleavage site. Cell line JHK3a revealed a single ~7 kb band in XhoI cut DNA and a single ~7 kb band in HindIII cut DNA. Cell line JHK3b showed a single ~13 kb band and a single ~10 kb band in XhoI and HindIII treated DNA, respectively.

Structurally, the Pc-PP'-tk-P'P fragment was intact in both cell lines. The attP sequence contained a BstEII site. Cleavage by BstEII released a single ~2 kb tk fragment detected by the tk probe and both lines showed this pattern. The Pc-PP'-tk-P'P fragment was also functional with respect to tk expression. In these two cell lines, the addition of gancyclovir to the growth media, even at the lowest concentration tested (1 mM), resulted in the arrest of metabolic activity, as determined by the lack of a color change in the growth media and by microscopic examination. In contrast, the parental nontransgenic line was resistant to gancyclovir up to the highest concentration tested (50 mM), as the growth media changed from a reddish to a yellowish coloration and the cells proliferated.

For simplicity, FIG. 5 depicts the zeocin resistance marker downstream of Pc-PP'-tk-P'P fragment, although the molecular data could also be compatible with it being upstream. Since the relative placement of the selectable marker gene is not important, its precise location was not determined.

Exchange of hpt Into the Target Locus

Figure 5C:
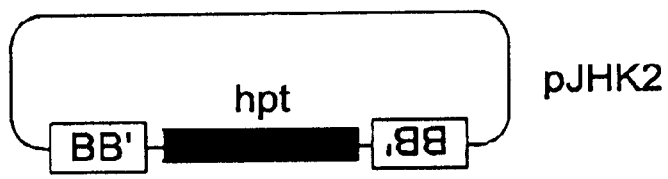
FIGS. 5C–D show the DNA substrates to demonstrate the sense expression of the introduced reporter gene hpt.
Figure 5D:
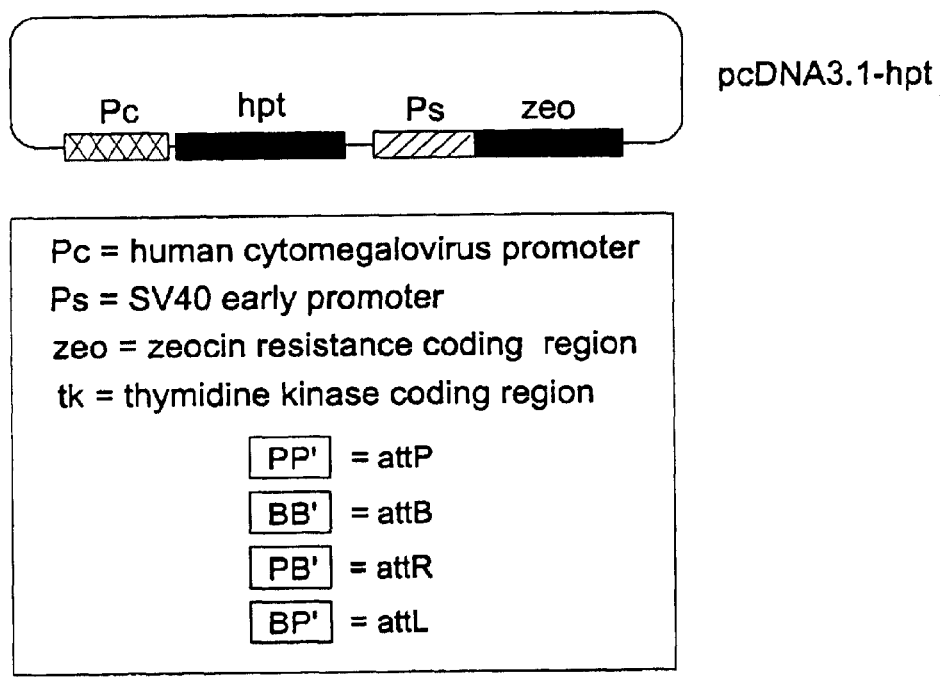
Figure 5E:
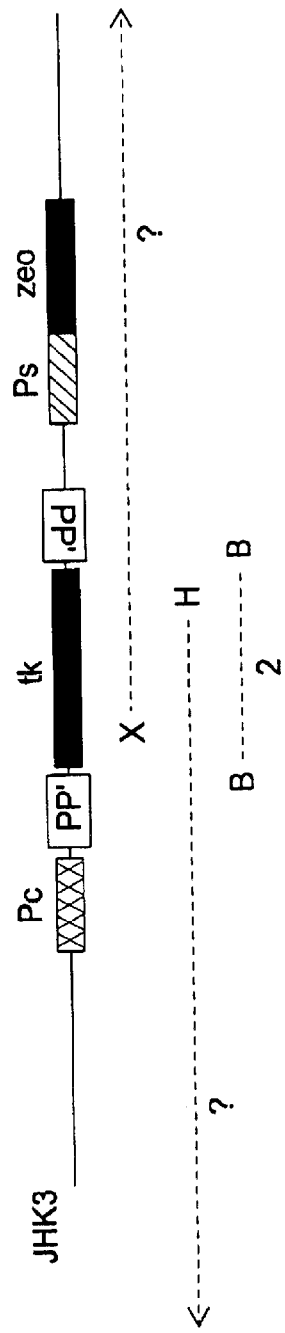
FIG. 5E shows the single copy receptor construct in the human genome.

To test the concept of directing a DNA exchange reaction at the genomic target, cell lines JHK3a and JHK3b were transfected with pJHK2 with or without the φC31 integrase-expressing construct pJHK1. The construct pJHK2 contains a BB'-hpt-B'B fragment, where BB' and B'B represent, respectively, the forward and reverse orientation of a 53 bp attB sequence (FIG. 5C). Recombination between the hpt 5'-attB and the tk 5'-attP links Pc with hpt, allowing for the expression of hpt and conferring resistance to hygromycin. However, recombination between the hpt 5'-attB and the tk 3'-attP links Pc with the antisense orientation of hpt, and the cell should retain hygromycin sensitivity. Therefore, the number of hygromycin resistant colonies recovered represents only half of the total DNA targeting events.

Table 2 lists the transfection results with the two cell lines. The control plasmid pcDNA3.1-hpt, which harbors a Pc-hpt fragment that expresses the hpt gene (FIG. 5D), yielded ~3,200 hygromycin resistant colonies per million cells. This indicates a random integration frequency of about 0.3%. When transfected with both pJHK1 and pJHK2, ~88 to 550 hygromycin resistant colonies were recovered. Assuming that only half of the targeted event were scored as hygromycin resistance, this translates to ~180 to 1,100 targeting events, or between ~2.8% to 17% of the random transformation frequency. In contrast, hygromycin resistant colonies were not found when either pJHK1 or pJHK2 was the sole transfection substrate.

Figure 5F:
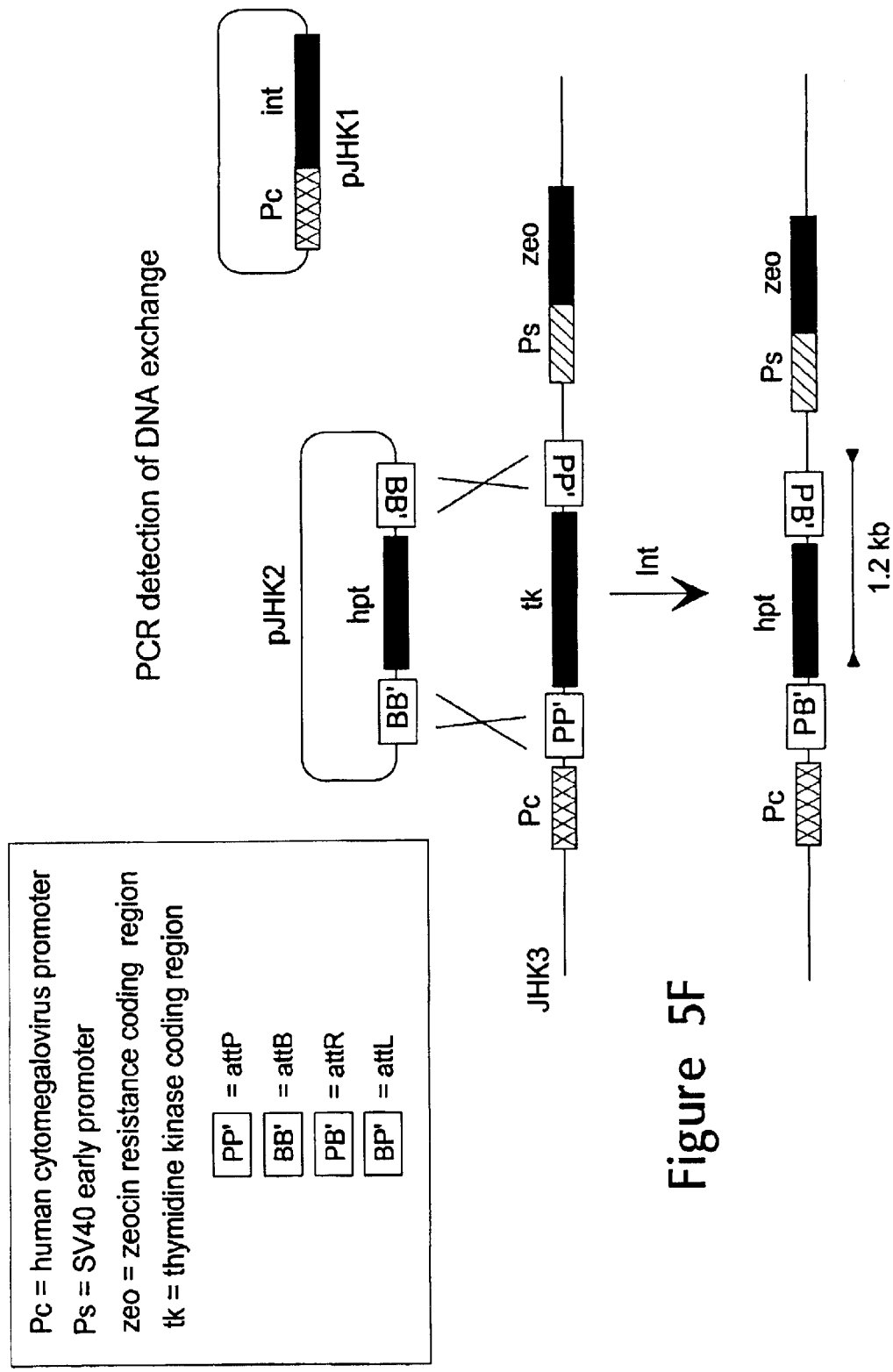
FIG. 5F shows a strategy for the PCR detection of DNA exchange.

The hygromycin resistance phenotype indicates that hpt has integrated behind a genomic promoter. As hygromycin resistant colonies were not recovered from the control transfection, by pJHK2 without pJHK1, the resistance phenotype must be due to recombination between the hpt 5'-attB and the tk 5'-attP sites to form a Pc-hpt junction. To test if recombination had also occurred between the hpt 3'-attB and the tk 3'-attP sites, representative clones were analyzed by PCR. Primers corresponding to hpt and to DNA adjacent to the tk 3' attP sequence were used for PCR reactions on representative hygromycin resistant clones (FIG. 5F). The expected 1.2 kb PCR product was detected in all of 8 representative clones, but not from the progenitors JHK3a or 293T. This indicates that the recombination between the hpt 5'-attB and the tk 5'-attP sequence (sense orientation) can be accompanied by recombination between the hpt 3'-attB and the tk 3'-attP. Likewise, it is expected that the recombination between the hpt 5'-attB and the tk 3'-attP sequence (antisense orientation) can be accompanied by a recombination between hpt 3'-attB and the tk-5'-attP. These dual recombination reactions will exchange out the tk DNA.

Gancyclovir Resistance from DNA Targeting

The recombination between the hpt 5'-attB and the tk 5'-attP not only links Pc with hpt, but also displaces tk from Pc. Therefore, a targeted event was expected to produce a gancyclovir resistant phenotype. When hygromycin clones were transferred onto media with 50 μM gancyclovir, after one week, 9 of the 12 clones exhibited clear resistance to this nucleoside analog. The other clones appear sensitive or perhaps have a low level of tolerance to gancyclovir. A sensitive or low resistance phenotype is possible for a variety of reasons. For example, depending on the metabolic state of the cell, it may take longer for a cell to be free of previously synthesized tk proteins. Alternatively, the tk gene that is exchanged out of the target locus may have integrated elsewhere in the genome.

In summary, the recovery of clones that exhibit resistance to hygromycin, sensitivity to gancyclovir, and the correct molecular junction is consistent with the DNA exchange event shown in FIG. 5A.

TABLE 2

Transfection results scored as hygromycin resistant colonies per million cells.

| Cell line | JHK3a Hyg$^R$ | frequency (%) | JHK3b Hyg$^R$ | frequency (%) |
|---|---|---|---|---|
| Transfection substrate | | | | |
| No DNA | 0 | <1.00E-06 | 0 | <1.00E-06 |
| pJHK1 | 0 | <1.00E-06 | 0 | <1.00E-06 |
| pJHK2 | 0 | <1.00E-06 | 0 | <1.00E-06 |
| pJHK1 + pJHK2 | 550 | 5.50E-04 | 88 | 8.80E-05 |
| pcDNA3.1-hpt | 3200 | 3.20E-03 | 3500 | 3.50E-03 |

Example 4

Gene Replacement in Plant Cells Using Linear DNA Molecules

This Example illustrates a strategy for gene replacement using linear DNA molecules in plant cells. Compared to Example 2, this example incorporates two additional features: First, the host cell produces the integrase or recombinase protein, so a co-transforming integrase or recombinase expression construct is not needed, and second, the trait gene is flanked by inverted attB sites. This allows the gene fragment to be placed behind a genomic promoter in either orientation. In one orientation, a sense transcript would be produced, in the other orientation, an antisense transcript would be produced. Sense expression could lead to hyper expression of the gene, whereas antisense expression could lead to suppression of the corresponding host gene or gene family.

FIG. 6 depicts a general strategy using two specific constructs. The target construct consists of a RB-P-attP-int-35S-codA-35S-npt (inverted attP)-LB fragment. Abbreviations used: P, promoter; 35S, CaMV 35S promoter; codA, cytosine deaminase gene coding region, npt, kanamycin resistance gene coding region. The attP site and the corresponding int gene belong to the class of irreversible recombination systems such as the φC31 system. RB and LB are the right and left T-DNA border sequences from Agrobacterium mediated gene transfer. The 35S-npt fragment permits selection of the target construct in the host genome. The codA gene is a counter-selectable marker, which encodes cytosine deaminase, an enzyme that can convert supplementary 5-fluorocytosine to toxic 5-flurouracil. If 5-fluorocytosine is added to the culture medium, only cells that have lost the functional codA gene will thrive. The use of alternative selectable markers, counter-selectable markers, and promoters are possible.

The integrating construct consists of a gene fragment, in this case, a cDNA, flanked by a set of attB sites of inverted orientations. Two possible configurations can be achieved that results in loss of the coda counter-selectable marker. In one configuration, the cDNA is transcribed in the sense orientation (FIG. 6A). In the other configuration, cDNA is transcribed in the antisense orientation (FIG. 6B).

Example 5

Use of Two Recombinase Systems to Introduce a Gene into a Chromosome and Excise Extraneous DNA This example illustrates a general strategy to combine two different recombination systems to deliver a gene to a designated chromosome target followed by removal of the unneeded DNA. The strategy is diagrammed in FIG. 7.

Methods

FIG. 7 depicts a general strategy using two specific constructs. The receptor construct consists of a P-attP-int-P-sel1 fragment flanked by a set of inverted recombination sites belonging to the class of recombination systems where the recombination sites are identical or nearly identical in sequence. These recombination systems include, for example, the Cre-lox system, the FLP-FRT system, the R-Rs system, and the β recombinase-six system. P stands for a promoter, sel1 for a selectable marker, int for an integrase or a recombinase coding region corresponding to the respective attP site. The attP site in this case can be a recombination site belonging either to the class of irreversible recombination systems such as the φC31 system as shown in FIG. 7A, or to the class of reversible recombination systems as shown in FIG. 7B such as the Cre-lox system, the FLP-FRT system, the R-Rs system, or the β recombinase-six system.

The donor integrating construct consist of attB-sel2-P-trait, where P-trait is flanked by a set of inverted recombination sites belonging to the class of recombination systems where the recombination sites are identical or nearly identical in sequence. "Trait" is the gene that confers the trait to be engineered into the genome. The attB site in this case can be a recombination site belonging either to the class of irreversible recombination systems such as the φC31 system, or to the class of reversible recombination systems such as the Cre-lox system, the FLP-FRT system, the R-Rs system, and the β recombinase-six system.

Step 1: The P-attP-int-P-sel1 target construct, flanked by the inverted recombination sites, is inserted by conventional transformation into the host genome. If desired, the inverted recombination sites can be used to facilitate the construction of single copy transgenes by the resolution of complex integration patterns as described in, for example, U.S. Pat. No. 6,114,600. Alternatively, single copy transgenic recipients can be obtained through molecular screening methods.

Step 2: The integrating construct is transformed into the target line, which is the transgenic cell line that contains the target construct. In this example, the target line produces the integrase or recombinase. If the target line does not express the integrase or recombinase, the gene, mRNA or protein corresponding to the integrase or recombinase can be co-introduced along with the integrating construct. The integrating construct will integrate by attP×attB recombination into the genomic target. This will place the trait gene between two sets of fragments that are not needed for function of the trait gene and that can be removed by site-specific deletion of the DNA bracketed by recombination sites.

Step 3. The recombinase, or recombinase gene, mRNA, or protein, corresponding to the recombination sites that bracket the two sets of unneeded DNA is then introduced into the host cell by either a stable or a transient method. For example, the stable introduction of a recombinase gene can be through a genetic cross, or through another round of stable transformation. The transient introduction of the recombinase can be introduced by transformation methods that deliver the protein or mRNA molecule, or by delivery of the recombinase gene that do not result in stable integration of the DNA molecule.

Step 4. Upon successful site-specific recombination of the unneeded DNA by the introduced recombinase, the host cell will contain only the desired trait gene flanked by a set of inverted recombination sites.

FIG. 7B depicts a variation of the strategy in which the removal of unneeded DNA is conducted with a second irreversible recombination system that does not recognize the irreversible recombination sites of the first irreversible recombination system. The receptor target construct consists of a P-attP-int-P-sel1 fragment flanked by a set of irreversible recombination sites, attP-2 (PP'-2), from a second irreversible recombination system. The donor integrating construct consists of attB-sel2-P-trait, where P-trait is flanked by a set of irreversible recombination sites, attB-2 (BB'-2), from a second irreversible recombination system.

Step 1: The P-attP-int-P-sel1 target construct, flanked by attP-2 sites, is inserted by conventional transformation into the host genome.

Step 2: The integrating construct is transformed into the target line, integrating by attP×attB recombination into the genomic target. This will place the trait gene between two sets of fragments that are not needed for function of the trait gene and that can be removed by site-specific attP-2×attB-2 recombination.

Step 3. The recombinase corresponding to the attP-2 and attB-2 sites is then introduced into the host cell by either a stable or a transient method.

Step 4. Upon successful site-specific recombination of the unneeded DNA by the introduced recombinase, the host cell will contain only the desired trait gene flanked by a set of hybrid recombination sites PB'-2 and BP'-2.

Example 6

Gene Stacking

This Example illustrates a general strategy to combine the use two different recombination systems to deliver a series of genes to a designated chromosome target followed by the removal of unneeded DNA. The sequential addition of trait genes to the same genomic site is referred to as "gene stacking." This method results in a precise stacking of a series of trait genes at a genomic location without incorporating other unneeded DNA that could cause additional concerns, such as antibiotic resistance markers. The method is applicable for all cells that can be transformed by DNA, including animal and plant cells.

Methods

FIG. 8 depicts an example of this strategy that uses a series of specific constructs. The receptor or target construct is the same as that described in FIG. 7A, except that the attP site in this case must be from the class of irreversible recombination systems such as the φC31 system.

The first donor or integrating construct contains attB-sel2-P-trait1-attB, where P-trait1-attB is flanked by a set of inverted recombination sites belonging to the class of reversible recombination systems where the recombination sites are identical or nearly identical in sequence. For illustrative purposes, the Cre-lox system is used herein as an example of this class of recombination systems; however, other reversible recombinases are also suitable. The gene trait] is the trait gene to be engineered into the genome, P stands for a promoter, and sel2 is a selectable marker coding-region. The attB site in this case must be from a recombination site belonging to the class of irreversible recombination systems such as the φC31 system.

Step 1: The P-attP-int-P-sel1 target construct, flanked by the inverted lox sites, is introduced by conventional transformation into the host genome (FIG. 8A).

Step 2: The integrating construct is transformed into the target line, i.e., the transgenic line containing the target construct (FIG. 8A). In this example, the target line produces the integrase or recombinase. If the target line does not express the integrase or recombinase, the gene, mRNA or protein corresponding to the integrase or recombinase can be co-introduced along with the integrating construct. The integrating construct will integrate by attP×attB recombination into the genomic target. Since there are two attB sites present in the integration construct, either site can recombine with the genomic attP site. If the attB site downstream of trait1 recombines with attP, then the resulting integration event will not activate expression of the selectable marker sel2. On the other hand, if the attB site upstream of sel2 recombines with attP, then a P-attR-sel2 linkage will be formed. Transcription of sel2 by an upstream promoter will confer a selectable phenotype. This class of integration events can be selected for. The resulting structure places the P-trait1-attB fragment between two sets of fragments that are not needed for function of the trait gene, and that can be removed by site-specific deletion of the DNA bracketed by directly oriented lox sites (FIG. 8B).

Step 3. The recombinase gene, mRNA, or protein, corresponding to the recombination sites that bracket the two sets of unneeded DNA is then introduced into the host cell by either a stable or a transient method. For example, the stable introduction of a recombinase gene can be through a genetic cross, or through another round of stable transformation. The transient introduction of the recombinase can be introduced by transformation methods that deliver the protein or mRNA molecule, or by delivery of the recombinase gene that do not result in stable integration of the DNA molecule.

Step 4. Upon successful site-specific recombination of the unneeded DNA, the host cell will contain only the desired trait gene and an attB site flanked by a set of inverted lox sites (FIG. 8C). The single attB site at the chromosomal target locus can now serve as a target for another round of site-specific recombination. Moreover, the lack of selectable marker genes in the host genome would mean that the previously used markers sel1 and sel2 could be used again for subsequent transformation.

Step 5. Introduction of trait2 (FIG. 8C). The second trait gene, trait2, can be introduced by an integration construct containing the following fragment: attP-P-trait2-attP-lox-P-sel2. Note that the sel1 or the sel2 marker can again serve as the selectable marker. Either attP sites can recombine with the genomic attB site to integrate the DNA at the target site and confer a selectable phenotype encoded by sel2. If the attP site downstream of trait2 recombines with attB, then the integration structure will be as shown in FIG. 8E. If the attP site upstream of P-trait2 recombines with attB, then the integration structure will be as shown in FIG. 8D. The two classes of integration structures can be determined by molecular analysis. Only the class shown in FIG. 8D will be useful for additional gene stacking. The class shown in FIG. 8D is kept, while the class shown in FIG. 8E is discarded.

Step 6. Repeat steps 3 and 4 to remove the unneeded DNA from the structure shown in FIG. 8D. This will result in the integration structure shown in FIG. 8F.

Figure 8F:
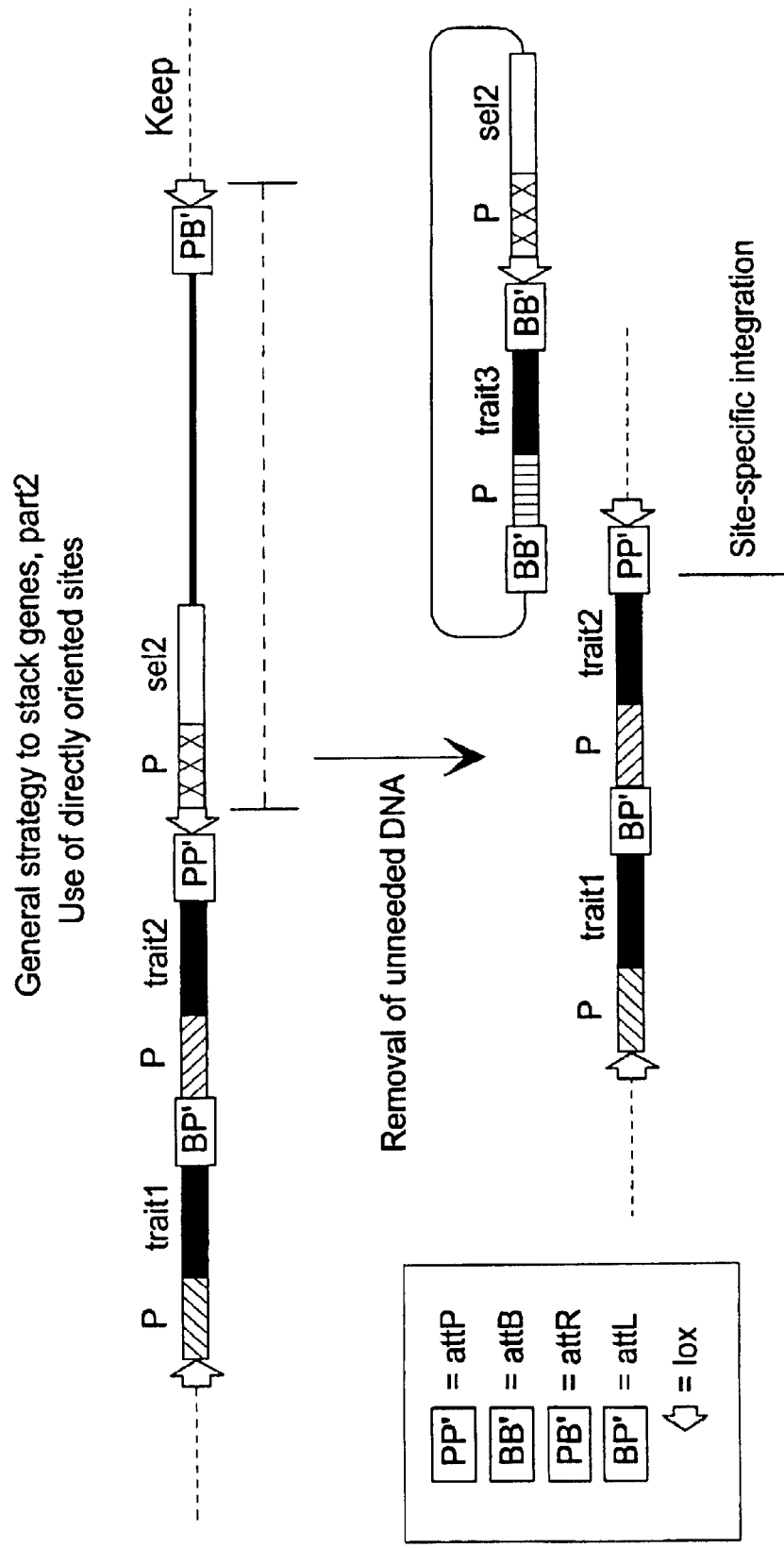
Figure 8G:
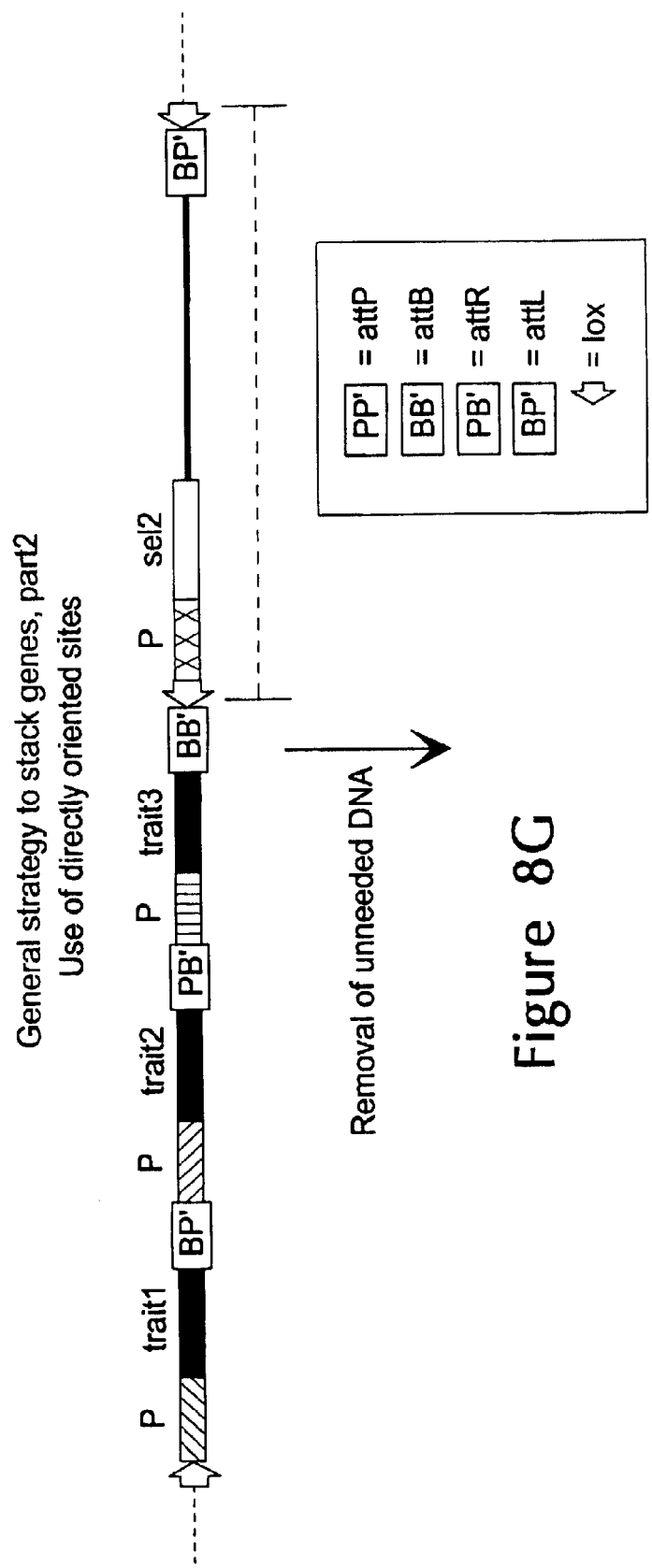

Step 7. Introduction of trait3 (FIG. 8F). The third trait gene, trait3, can be introduced by an integration construct containing the following fragment: attB-P-trait3-attB-lox-P-sel2. Note that the sel1 or the sel2 marker can again serve as the selectable marker. Either attB sites can recombine with the genomic attP site to integrate the DNA at the target site and confer a selectable phenotype encoded by sel2. Depending on which attB recombines with attP, the integration structure will differ. The two integration structures can be determined by molecular analysis. The structure that will permit further gene stacking is shown in FIG. 8G, which is derived from the recombination between the attB site upstream of P-trait3.

Step 8. Repeat steps 3 and 4 to remove the unneeded DNA from the structure shown in FIG. 8G. This will result in the integration structure shown in FIG. 8H.

Figure 8H:
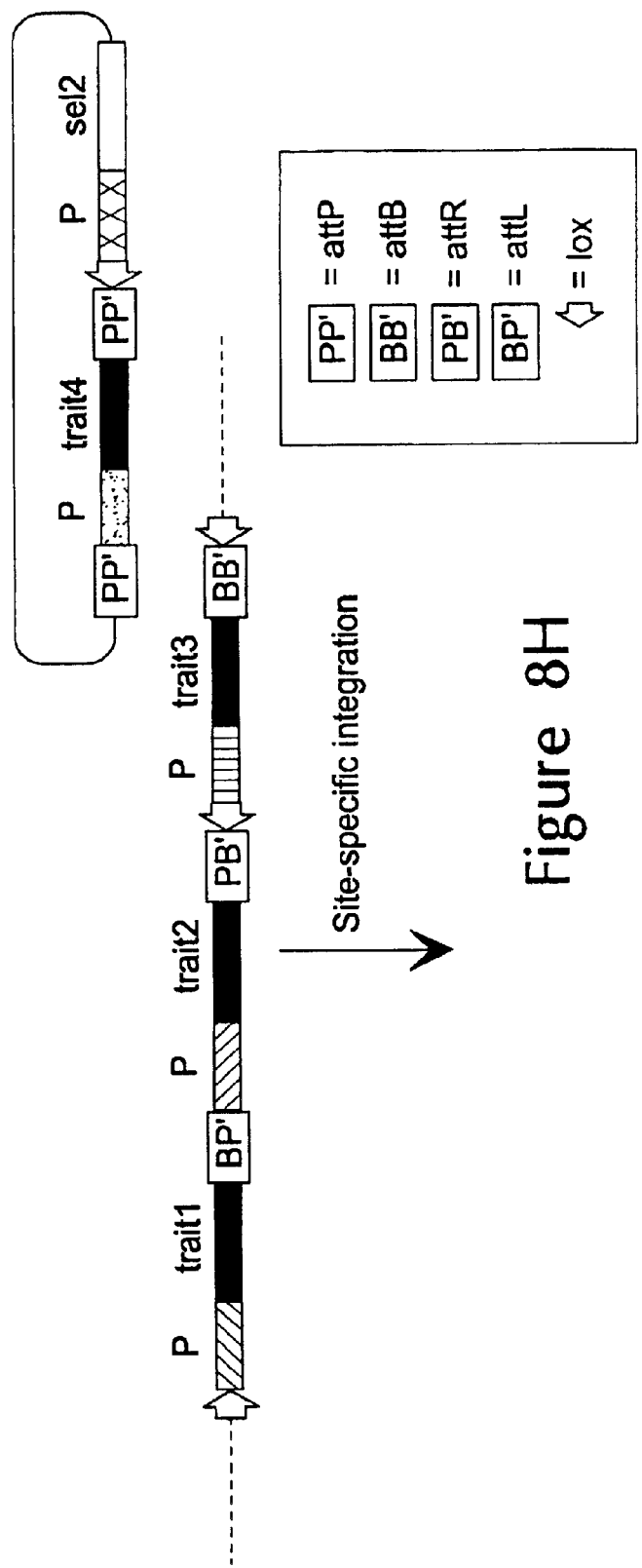
Figure 8I:
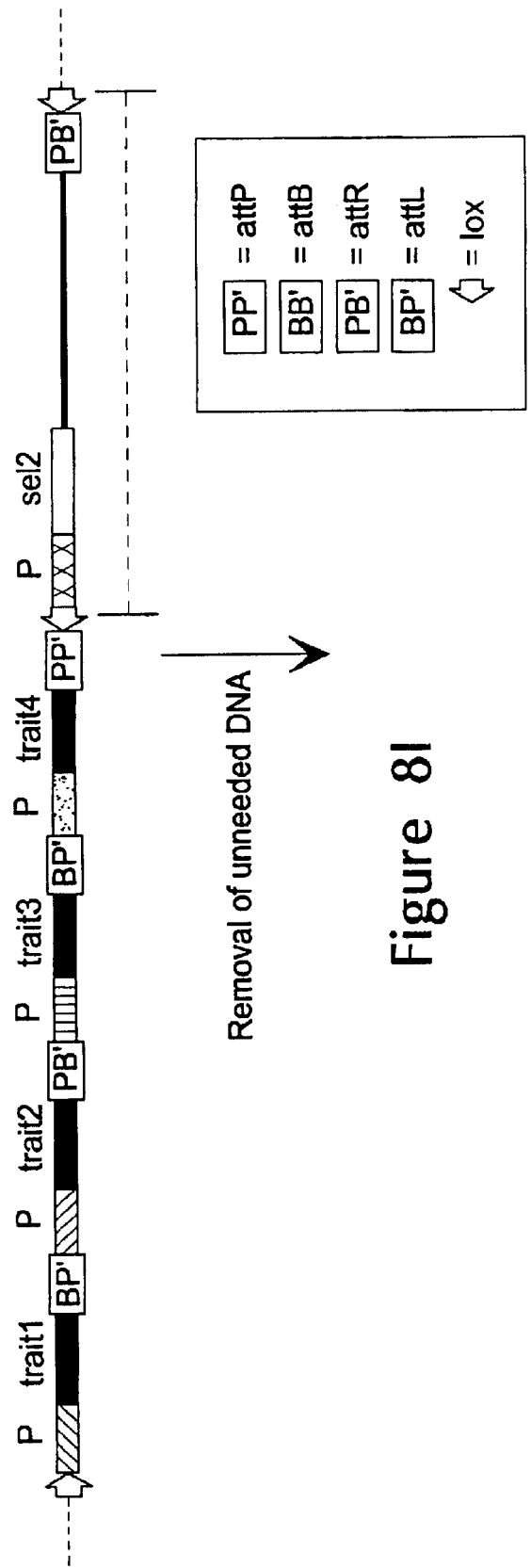

Step 9. Introduction of trait4 (FIG. 8H). The fourth trait gene, trait4, can be introduced by an integration construct containing the following fragment: attP-P-trait4-attP-lox-P-sel2. Note that the sel1 or the sel2 marker can again serve as the selectable marker. Either attP sites can recombine with the genomic attB site to integrate the DNA at the target site and confer a selectable phenotype encoded by sel2. Depending on which attP recombines with attB, the integration structure will differ. The two integration structures can be determined by molecular analysis. The structure that will permit further gene stacking is shown in FIG. 8I, which is derived from the recombination of the attP site upstream of P-trait4.

Step 10. Repeat steps 3 and 4 to remove the unneeded DNA in the structure shown in FIG. 8I. This will result in the integration structure shown in FIG. 8J.

Figure 8J:
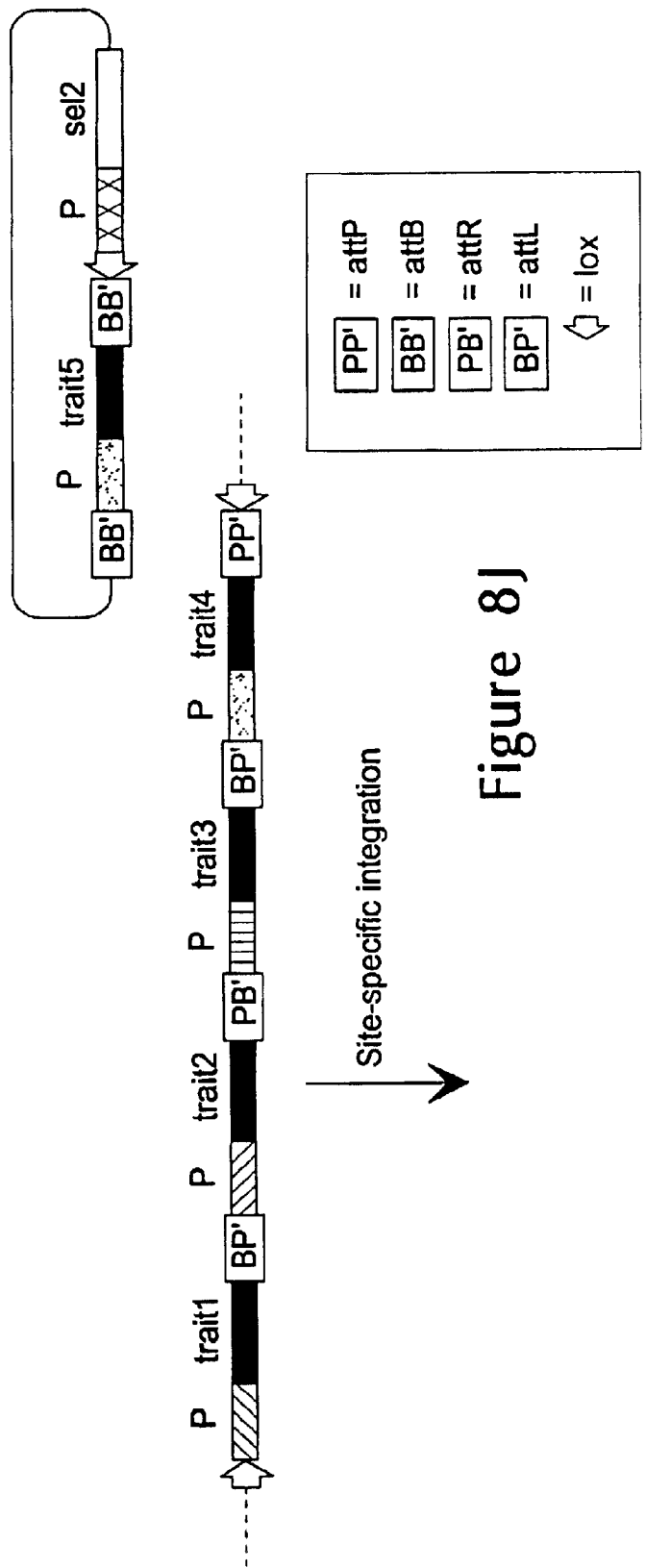
Figure 9A:
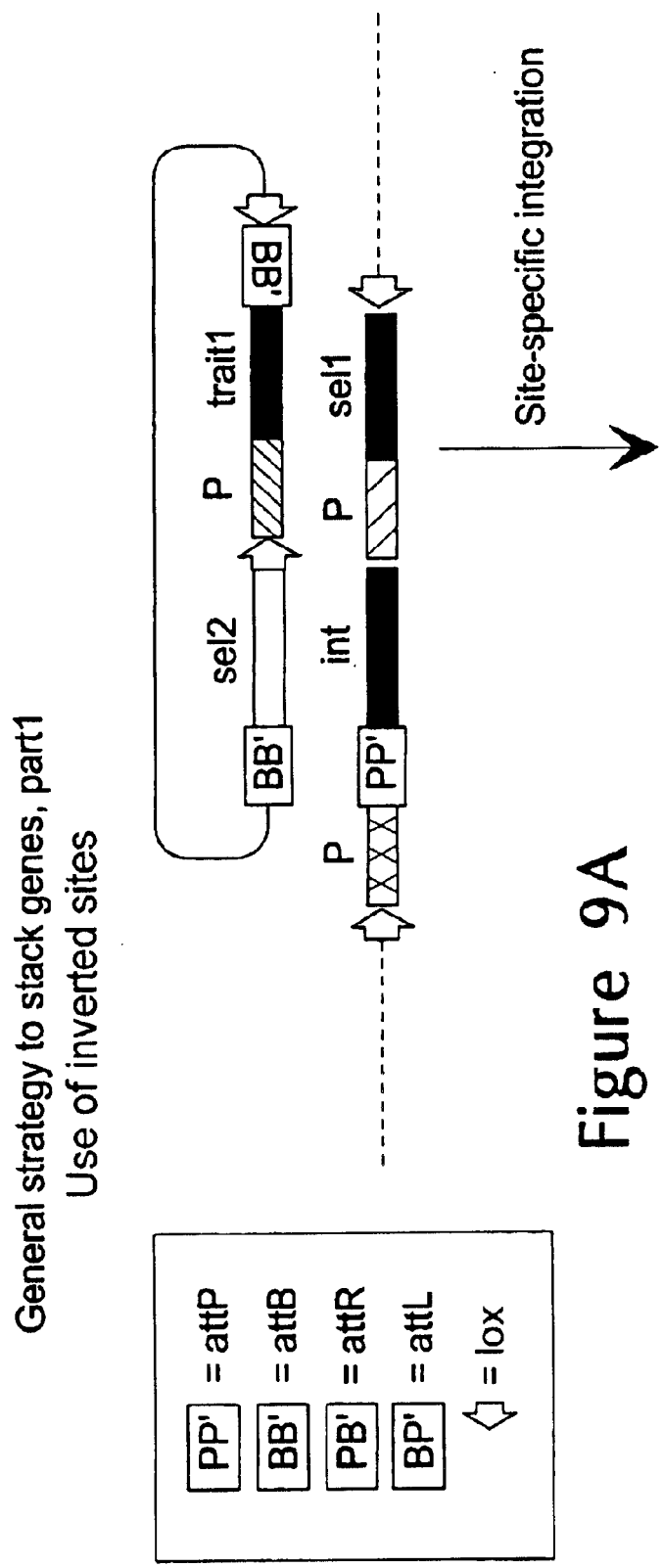
Figure 9B:
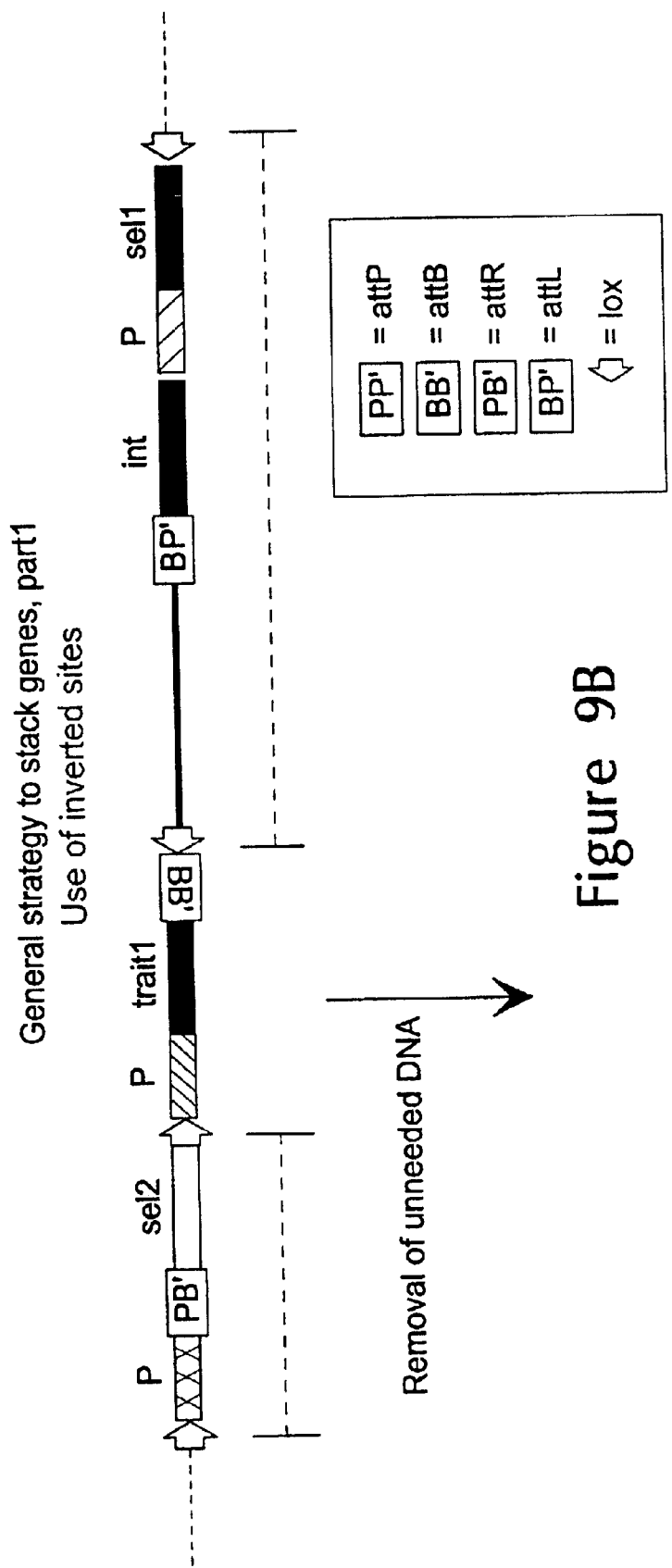
Figure 9C:
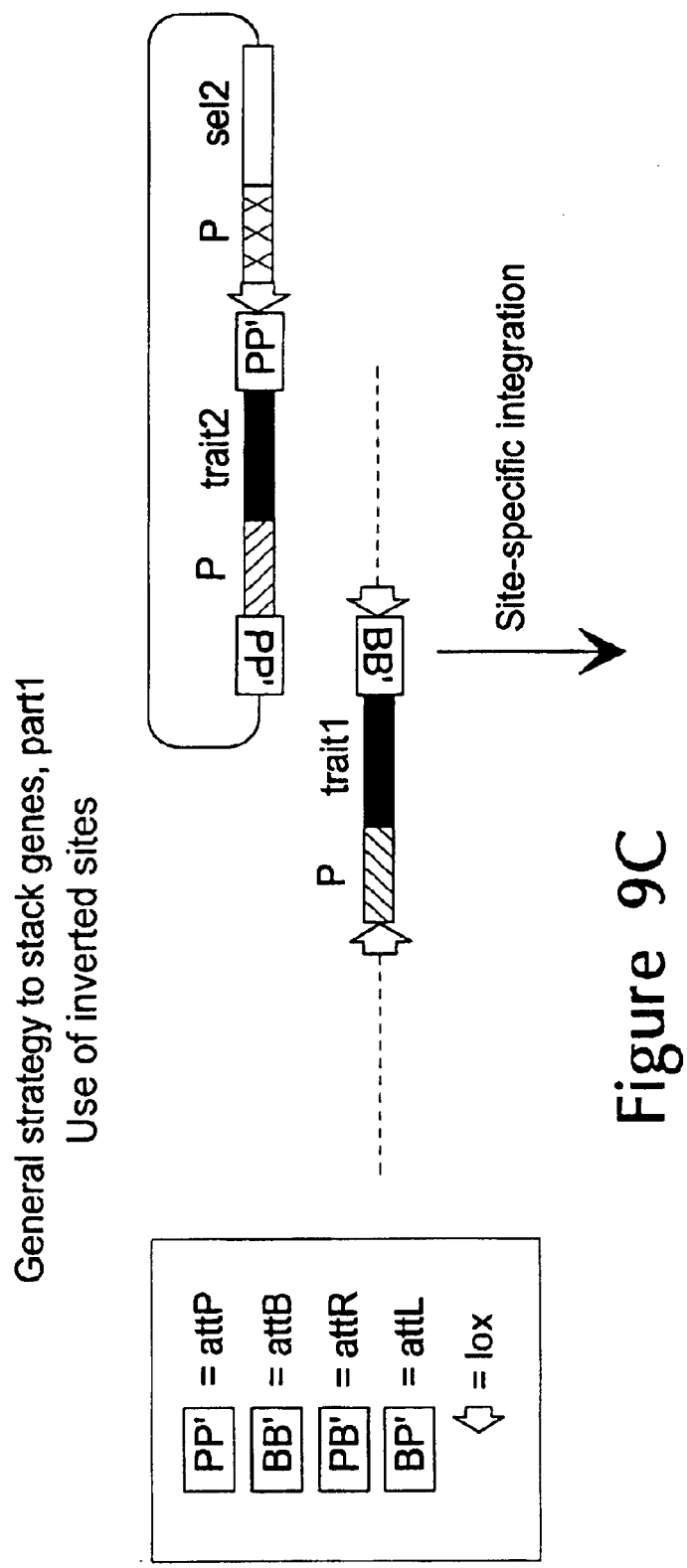
Figure 9D:
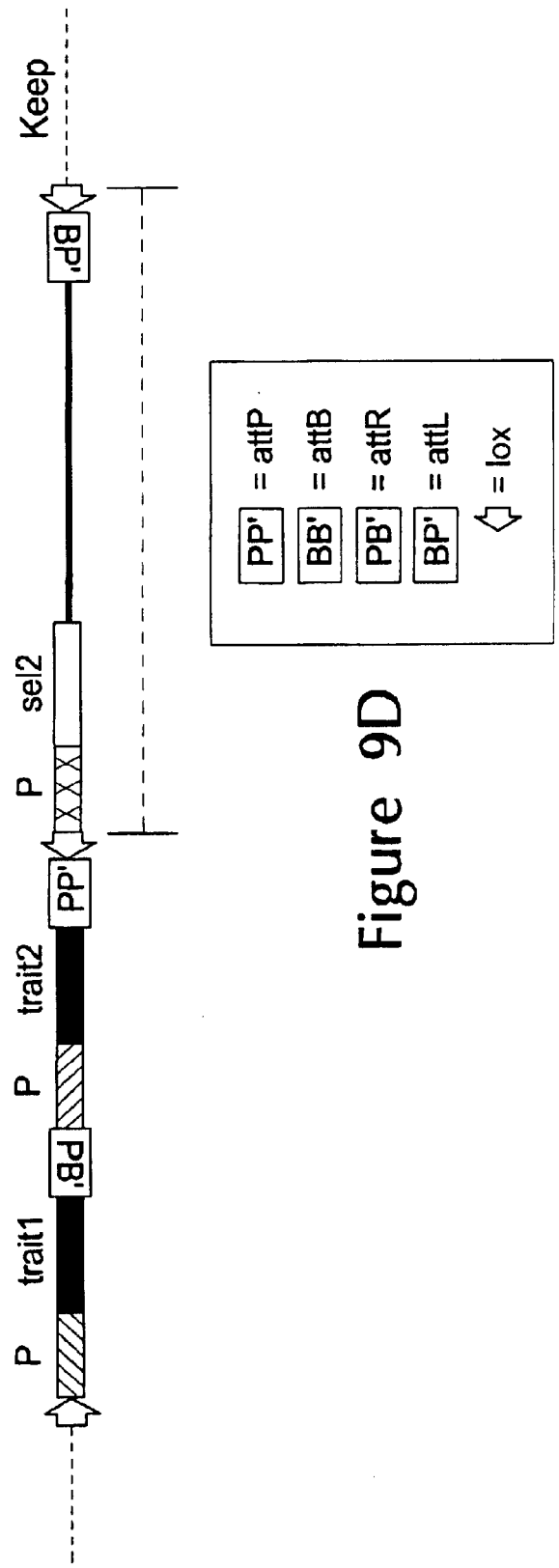
Figure 9E:
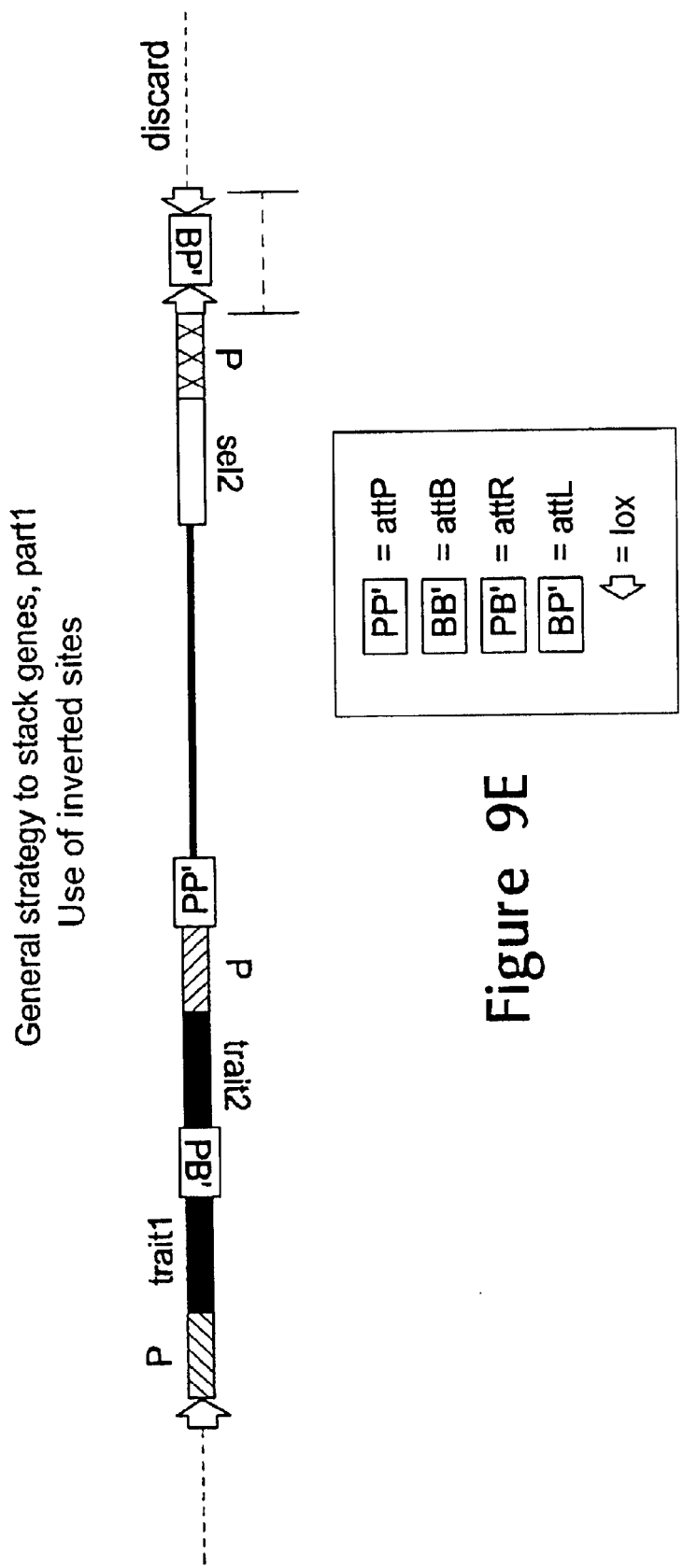
Figure 9F:
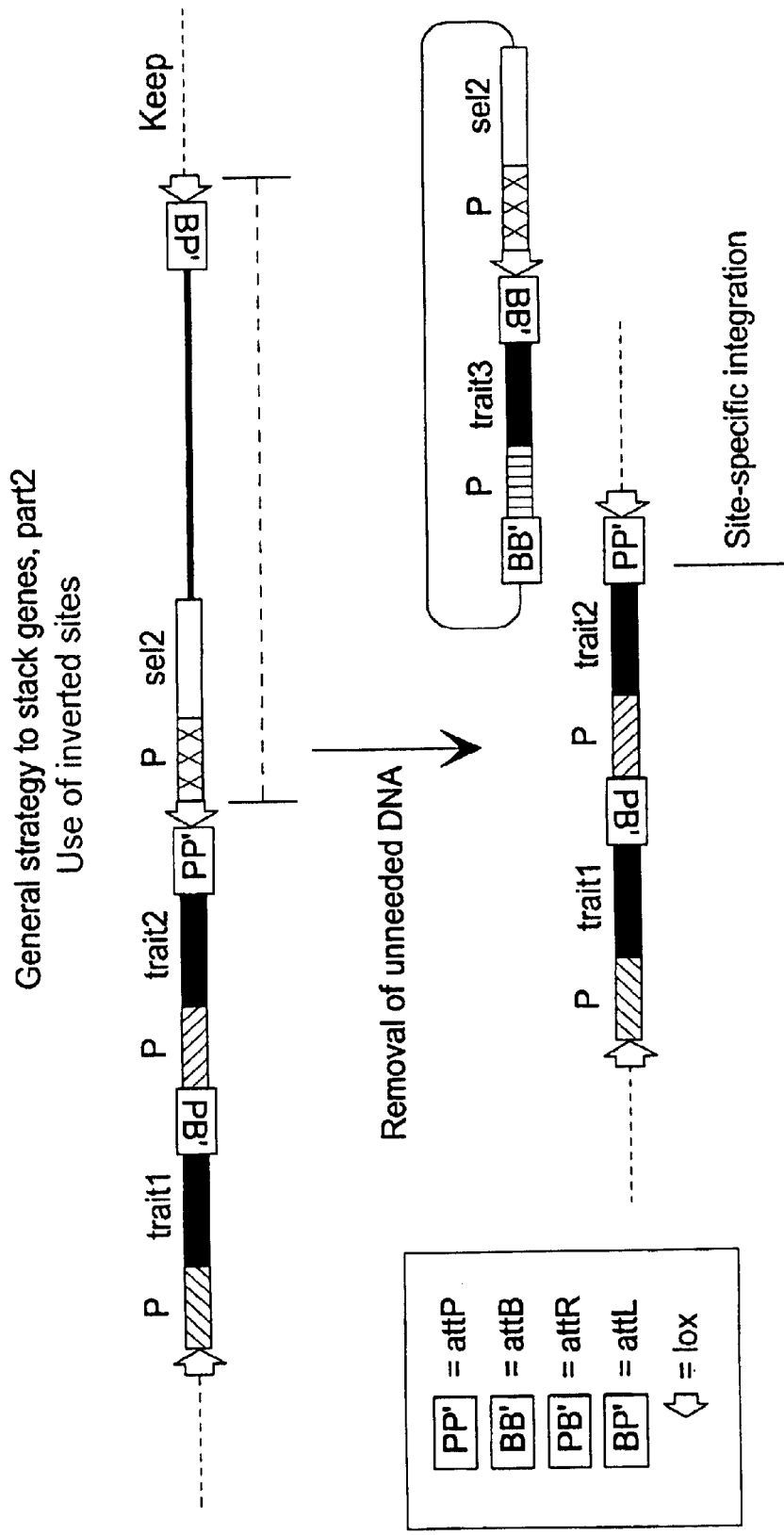
Figure 9G:
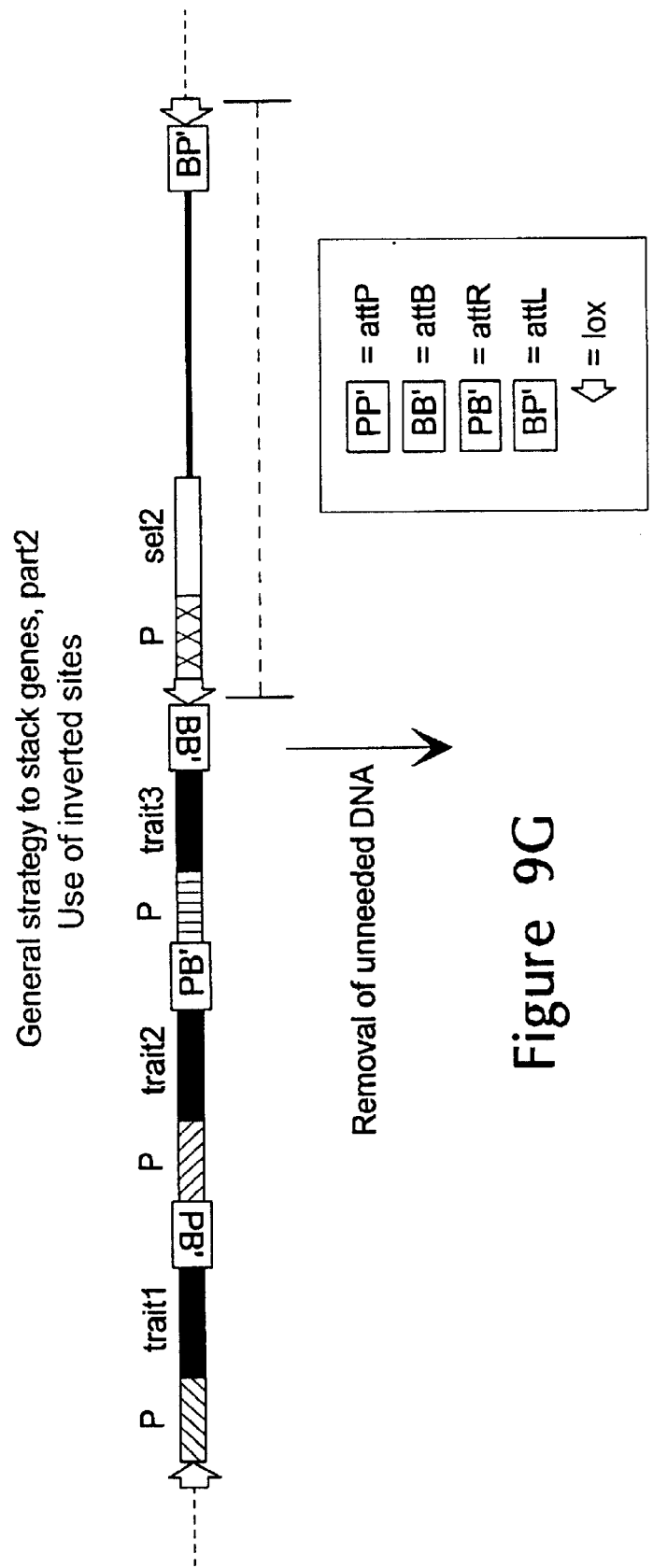
Figure 9H:
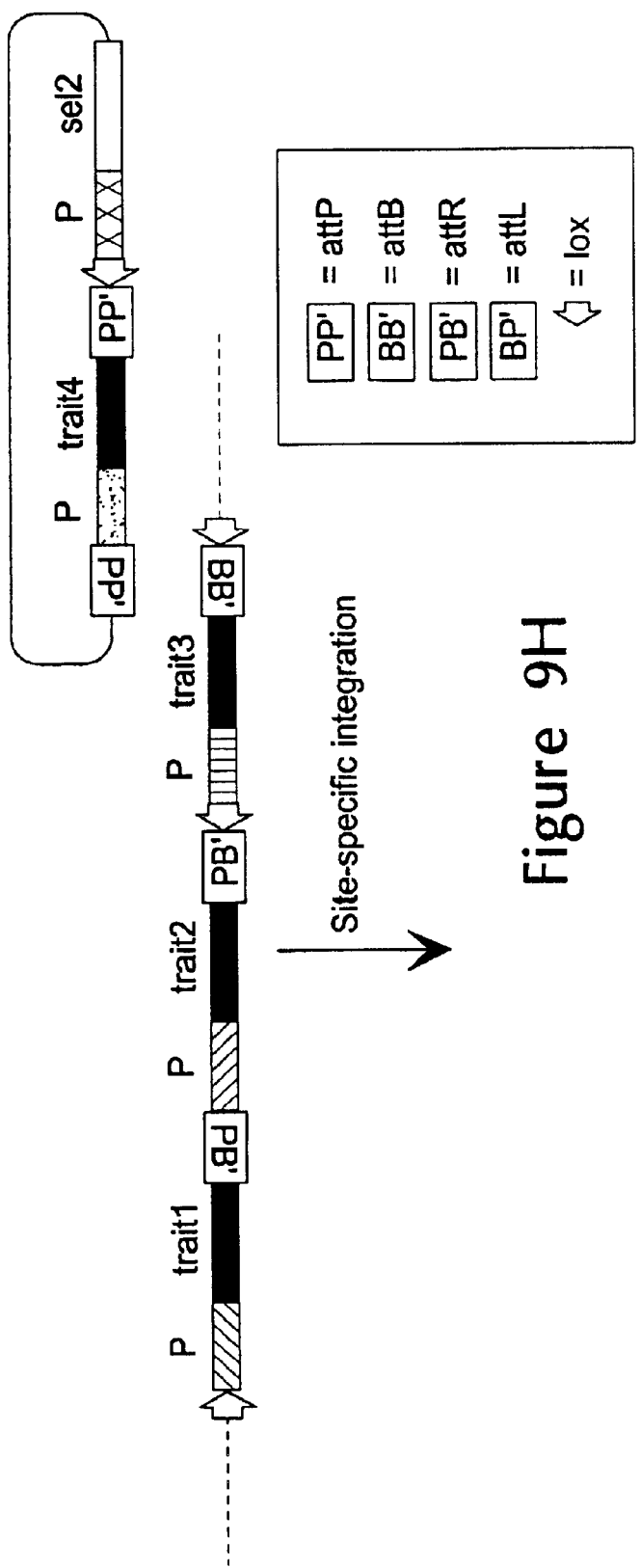
Figure 91:
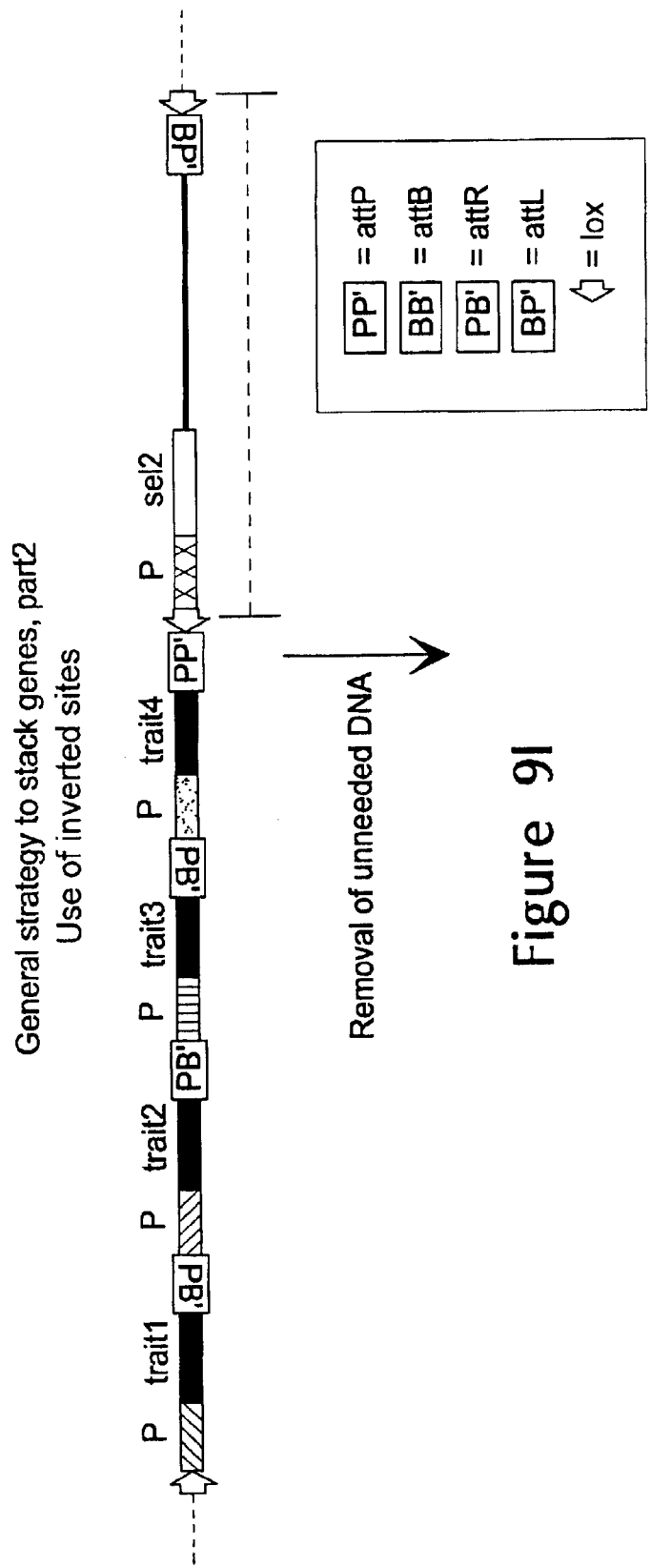
Figure 9J:
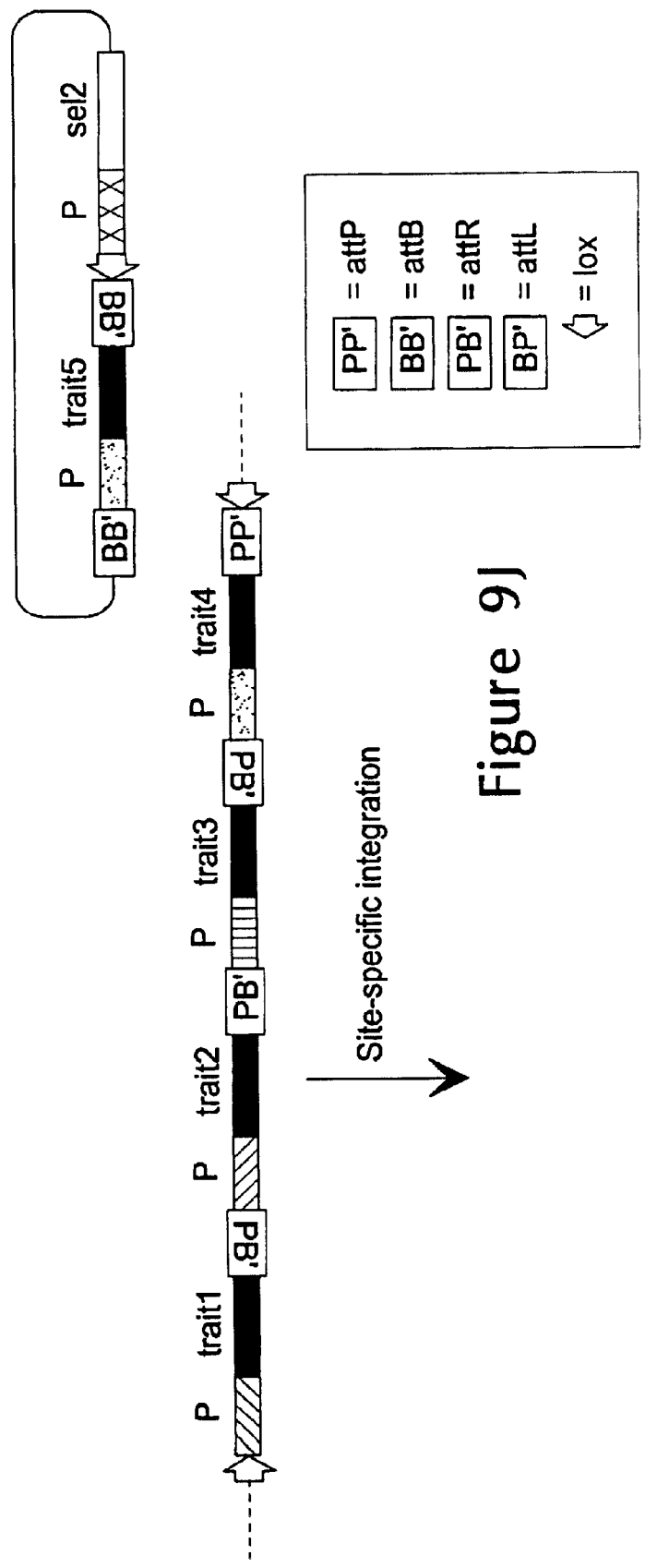

Step 11. Introduction of trait5 (FIG. 8J). The stacking of the fifth trait gene, trait5, is depicted in FIG. 8J. In principal, it is essentially the same as illustrated by the strategy to stack trait gene number 3, trait3. Likewise, the stacking of trait gene number 6 will be the same as the stacking of trait genes number 2 and 4. This recurring pattern can be repeated indefinitely, and the same marker gene can be "recycled" for use in each transformation event.

Variations

One can also use sets of inverted attB and attP sites, rather than sets of directly oriented sites. FIG. 9 illustrates this possibility. The set of events is essentially the same as that described for FIG. 8 except for the pairs of inverted attB and attP sites.

Example 7

Gene Replacement from Concatemeric DNA

This example illustrates a general strategy to deliver a DNA fragment to a designated chromosome target by a gene replacement strategy, and in conjunction with a second recombination system, the unneeded DNA can be subsequently removed from the genome. The integrating DNA is in concatemeric form, which can result from certain gene transfer methods such as biolistics.

Results

FIG. 10 depicts a general strategy for this method that uses two specific constructs. The target construct consists of a P-attP-int-P-sel1-attP fragment flanked by a set of inverted recombination site belonging to the class of reversible recombination systems where the recombination sites are identical or nearly identical in sequence. These recombination systems include, for example, the Cre-lox system, the FLP-FRT system, the R-Rs system, and the β recombinase-six system. In FIG. 10, P stands for a promoter, sel1 for a selectable marker coding-region, int for an integrase or a recombinase coding-region corresponding to the respective attP site. The attP site in this case is a recombination site belonging to the class of irreversible recombination systems such as the φC31 system.

The integrating construct contains attB-sel2-P-trait1-attB, where the P-trait segment is flanked by a set of inverted recombination sites belonging to the class of reversible recombination systems where the recombination sites are identical or nearly identical in sequence. For illustrative purposes, the Cre-lox system is used as an example of this class of recombination systems, although other reversible recombination systems are also suitable. The gene trait1 is the trait gene to be engineered into the genome, P stands for a promoter, and sel2 is a selectable marker coding-region. The attB site in this case is from a recombination site belonging to the class of irreversible recombination systems such as the φC31 system.

Figure 10A:
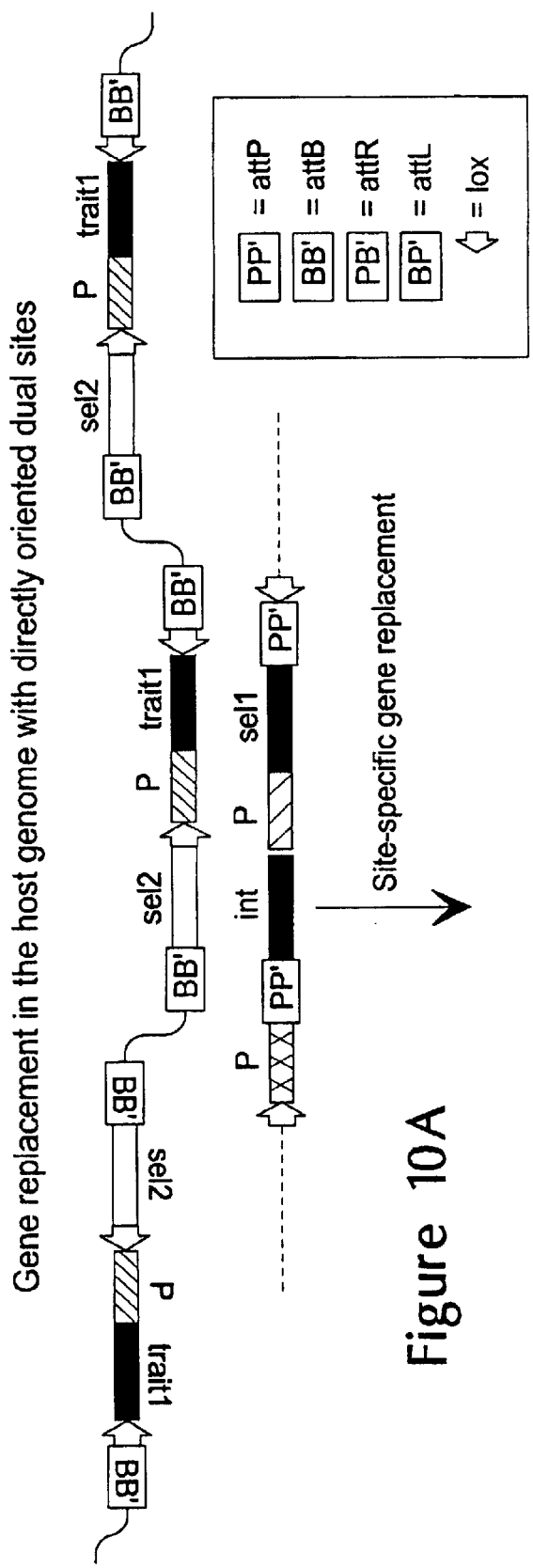
FIGS. 10A–C show a strategy where a single unit of a DNA concatemer can insert into the genome through gene replacement. In this instance, directly oriented dual recombination sites are used.

Step 1: The P-attP-int-P-sel1-attP target construct, flanked by the inverted lox sites, is introduced by conventional transformation into the host genome (FIG. 10A). If desired, the inverted lox sites can be used to facilitate the construction of single copy transgenic lines by the resolution of complex integration patterns as described in, for example, U.S. Pat. No. 6,114,600. Alternatively, single copy transgenic recipients can be obtained through molecular screening methods.

Figure 10B:
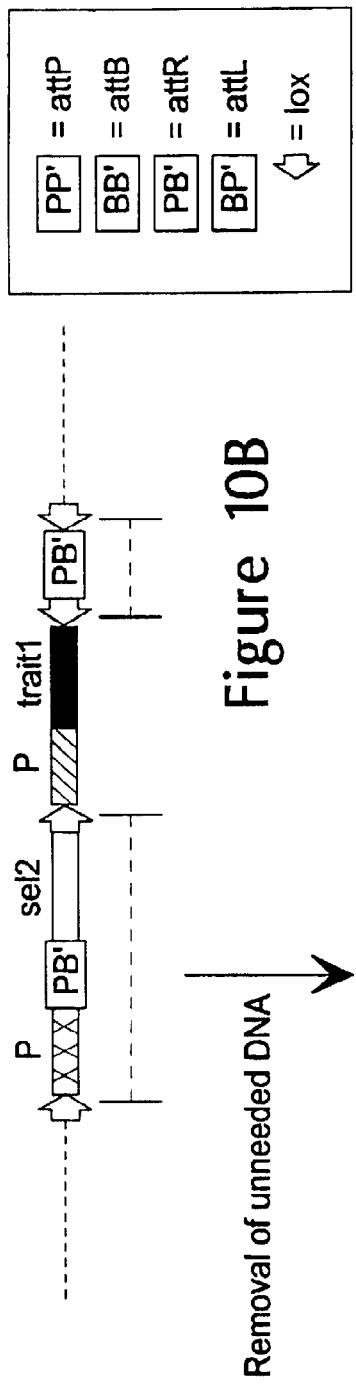

Step 2: The integrating construct is transformed into the target line, i.e., the transgenic line containing the target construct (FIG. 10A). In this example, the target line produces the integrase or recombinase. If the target line does not express the integrase or recombinase, the gene, mRNA or protein corresponding to the integrase or recombinase can be co-introduced along with the integrating construct. The integrating construct will integrate by attP×attB recombination into the genomic target. Since there are two attB sites present in the integration construct, and two attP sites present in the genomic target, either attB site can recombine with either genomic attP site. In this instance, only in the case where the attB site upstream of sel2 recombines with the attP upstream of int will there be a P-attR-sel2 linkage formed. Transcription of sel2 by an upstream promoter will confer a selectable phenotype. This integration event can be selected for, and must be followed by a second downstream attP×attB recombination. As depicted in FIG. 10A, recombination between the genomic attP and the attB site immediately downstream of trait1 would produce the configuration shown in FIG. 10A, B. However, even if another attB site further downstream of trait1 recombines with the genomic attP site, the final outcome would be the same. That is, the resulting structure places the P-trait1 fragment between two sets of fragments that are not needed for function of the trait gene, and that can be removed by site-specific deletion of the DNA bracketed by directly oriented lox sites (FIG. 10B).

Step 3. The recombinase gene, mRNA, or protein, corresponding to the recombination sites that bracket the two sets of unneeded DNA is then introduced into the host cell by either a stable or a transient method. For example, the stable introduction of a recombinase gene can be through a genetic cross, or through another round of stable transformation. The transient introduction of the recombinase can be introduced by transformation methods that deliver the protein or mRNA molecule, or by delivery of the recombinase gene that do not result in stable integration of the DNA molecule.

Figure 10C:
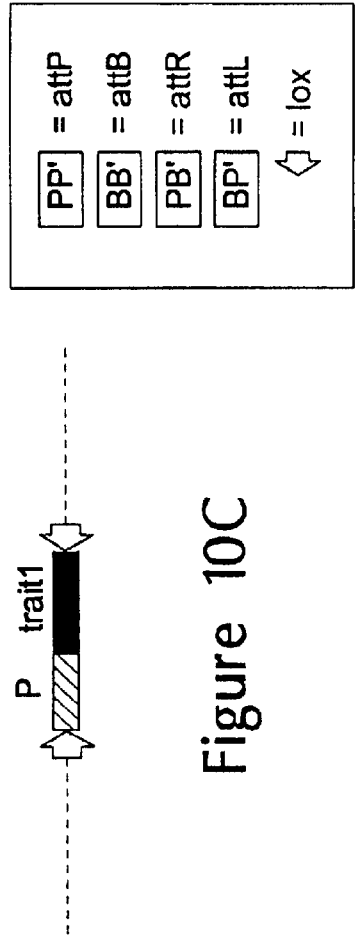

Step 4. Upon successful site-specific recombination of the unneeded DNA, the host cell will contain only the desired trait gene flanked by a set of inverted lox sites (FIG. 10C).

Variations

Figure 11A:
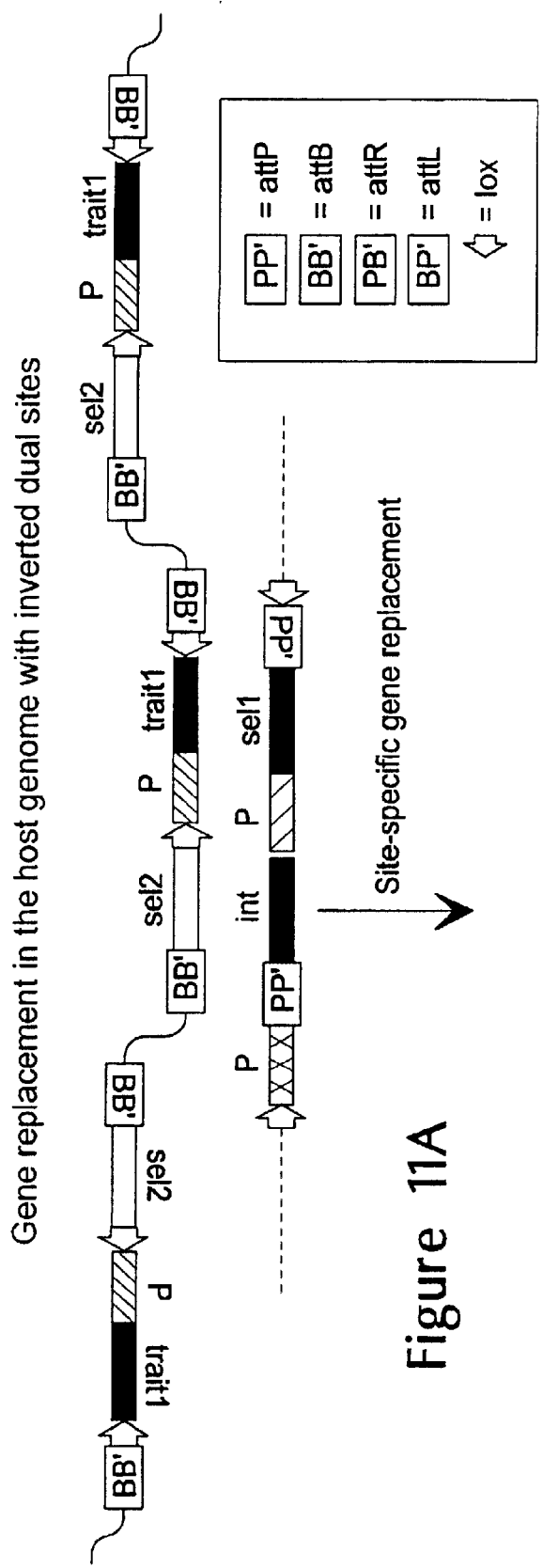

It is also possible to use sets of inverted attB and attP sites, rather than sets of directly oriented sites. FIG. 11 illustrates this possibility. The set of events is analogous to that described for FIG. 10 except for the pairs of inverted attB and attP sites.

Example 8

Transgene Translocation in *Arabidopsis* via Chromosome Recombination

This example demonstrates a strategy that uses the bacteriophage φC31 site-specific recombination system to translocate a transgene from one plant line to another. The strategy also incorporates the option to use a second site-specific recombination to remove the unneeded DNA, thereby leaving behind only the trait gene in the host genome.

The laboratory line (donor line) is transformed with a transgene that is flanked with a set of specific recombination sites. A corresponding set of sites is introduced into the elite line, the desired field variety (receptor line). When the laboratory line is crossed to the elite lines, site-specific recombination takes place between the laboratory line chromosome and the elite line chromosome. In the presence of the recombinase, the transgene would translocate from the laboratory line chromosome to the elite line chromosome without the translocation of adjacent DNA. In principle, the translocation event can be between non-homologous or homologous chromosomes. If between homologous chromosomes, the translocation event can be between different positions, or the same position in the homologous chromosome.

Figure 12A:
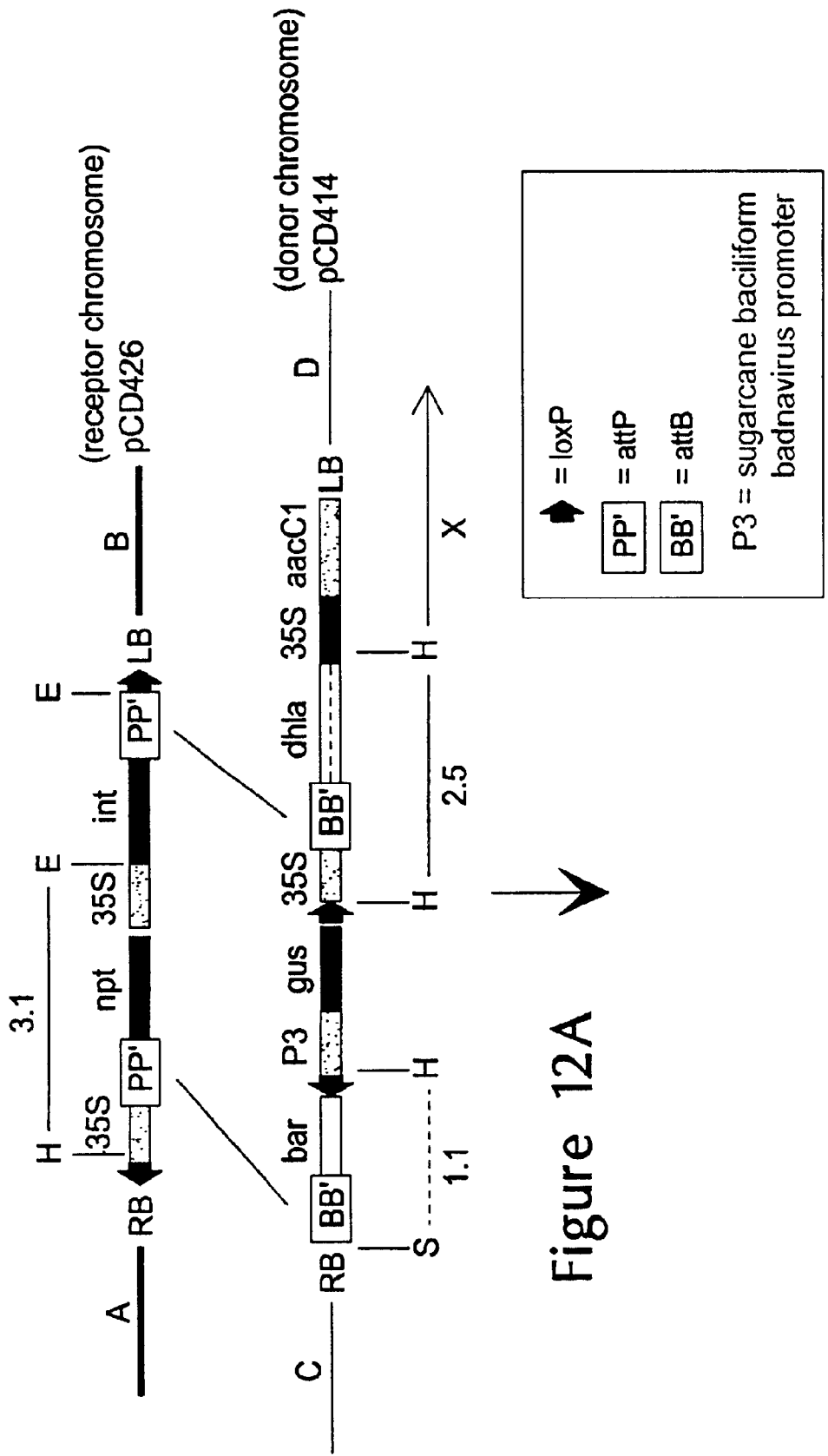
FIGS. 12A–C show a strategy for site-specific replacement of a polynucleotide between plant chromosomes, otherwise referred to as a "DNA fragment translocation" event, followed by the removal of DNA no longer needed for the expression of the trait gene (exemplified by P3-gus).

FIG. 12A depicts the two plant lines used in this demonstration. A target plant line was transformed with pCD426. This "receptor" construct was derived from an *Agrobacterium* gene transfer vector pPZP211. Inserted between RB and LB, the right and left border sequences of *Agrobacterium*-transferred DNA, was the following DNA segment: loxP-35S-PP'-npt-35S-int-PP'-(inverted loxP), where 35S is the cauliflower mosaic virus 35S RNA promoter, loxP is a wild type recombination site of the Cre-lox recombination system, PP' is the attP site of the φC31 recombination system, npt is the coding region of neomycin transferase, and int encodes the integrase of the φC31 recombination system. Whereas promoters are explicitly indicated in the figures, for simplicity, terminators that promote transcription termination and lie downstream of every coding region are not shown as separate elements.

The second plant line was transformed with pCD414, a "donor" construct derived from pPZP211. A DNA segment consisting of BB'-bar-loxP-P3-gus-(inverted loxP)-35S-BB'-dhlA-35S-aacC1 was inserted between RB and LB, where bar encodes resistance to the herbicide basta, P3 is a sugarcane bacilliform badnavirus promoter, gus is the coding region of β-glucuronidase, dhlA is the coding region for haloalkane dehalogenase (Naested et al., 1999 Plant J. 18:571–b 76), and aacC1 encodes resistance to gentamycin. The P3-gus fragment represents a typical trait gene destined for introgression into the receptor elite line.

When the donor line was crossed to the receptor line, integrase-promoted site-specific recombination was expected between the two chromosomes. If the npt-proximal PP' recombined with the bar-proximal BB', 35S would disengage from npt and fuse to bar. This event would confer resistance to basta. Any other PP'×BB' combination would not yield a bar selectable phenotype. If the downstream PP'×BB' event also took place, the 35S-dhlA linkage would be broken. Expression of dhlA confers sensitivity to DCE (1,2-dichloroethane). Hence, plants that are resistant to both basta and DCE should have the bar-loxP-P3-gus-(inverted loxP)-35S segment of DNA transloca to the receptor chromosome.

In this particular scenario, since the donor and receptor lines are independently transformed via random delivery of the T-DNA, the donor and receptor sites will be at different loci. Nonetheless, the same principle still applies if the donor and receptor sites are at the same locus (same position of homologous chromosomes). In all instances, the site-specific recombination on both sides of the transgene will eliminate the linkage drag of the donor DNA that flank the donor transgene.

Results and Discussion

Donor and Receptor Lines

*Arabidopsis* ecotype Columbia was transformed by *Agrobacterium*-mediated transformation with pCD426. Likewise, *Arabidopsis* ecotype Landsberg was transformed with pCD414. The two ecotypes have sufficient polymorphic markers such that if necessary, the amount of donor DNA can be estimated in the receptor line background. This simulates a typical introgression program between a donor laboratory line and an elite field variety, as represented by Landsberg and Columbia ecotypes, respectively.

Kanamycin resistant Columbia lines, conferred by the 35S-PP'-npt fragment, were analyzed by Southern hybridization. Approximately 10% of the kanamycin resistant plants were found to harbor a single intact copy of the pCD426 encoded T-DNA, as depicted in FIG. 12A. Gentamycin resistant Landsberg lines were also screened for single copy insertions, as conferred by the 35S-aacC1 DNA. Although in principle, it does not matter if the donor or the receptor lines contain multiple transgene copies, the counter-selection with the dhlA marker would not be effective unless all copies of the 35S-BB'-dhlA linkage is broken.

F1 Plants

Table 3 lists the pair-wise crosses between 3 single copy pCD426 and 7 single or low copy pCD414 lines. Eighteen of the possible 21 pair-wise combinations were crossed and yielded F1 progeny. F1 progeny were selected for resistance to gentamycin. A PCR assay was used to identify plants that also had the receptor locus. Those that met these criteria were selected for the production of F2 seed. In addition, these F1 plants were subjected to a set of tests for site-specific recombination.

Figure 12B:
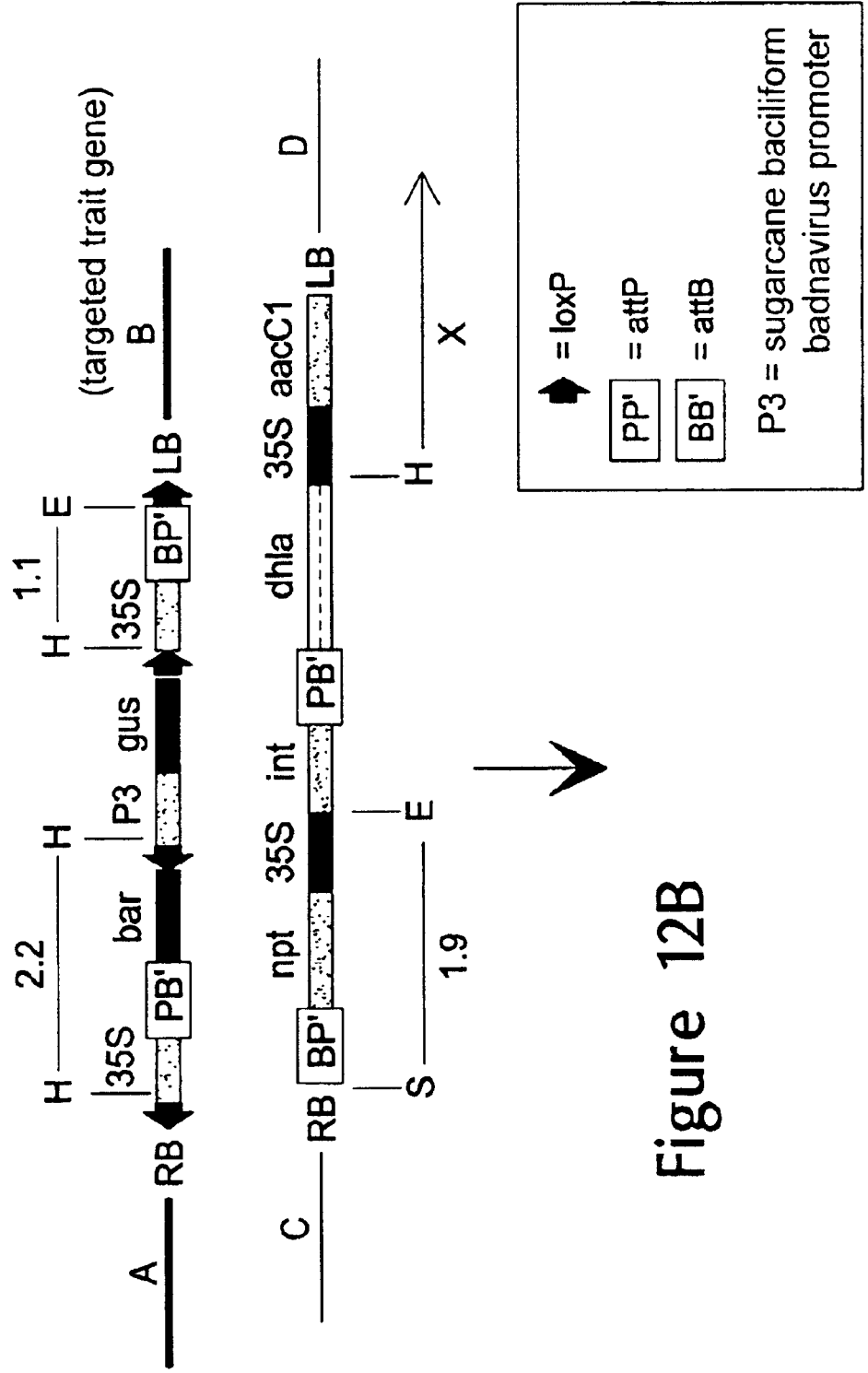

A first test was to examine for basta resistance in individual leaves that were painted with basta. In some combinations of crosses, some of the leaves showed signs of resistance to the herbicide, and remained green while parental leaves turned yellow. A second test utilized was PCR analysis of leaf DNA for the presence of a 35S-PB'-bar junction. Primers corresponding to the 35S and the nos3' terminator, which is present at the 3' end of both bar and npt should amplify a 1.1 kb 35S-PP'-npt non-recombinant junction and/or a 0.8 kb recombinant 35S-PB'-bar junction (FIGS. 12A, 12B). The relative abundance of the two junction bands should indicate the amount of recombination. In some F1 plants, the 0.8 kb 35S-PB'-bar junction was found. However, the relative low abundance of this 0.8 kb product, compared to the 1.1 kb product, suggested that only a minority of the cells have recombined.

A third test was Southern analysis of F1 floral and leaf tissues. DNA was cleaved with a combination of EcoRI, HindIII and SacI (FIGS. 12A, 12B, depicted as E, H, S, respectively) and hybridized to a 35S probe. FIGS. 12A and 12B show the cleavage patterns expected from the parental and recombinant chromosomes. In CD426, the hybridization probe is expected to detect a single 3.1 kb band. In CD414, the probe should hybridize to two bands, one of a predict size of 2.5 kb, and the other a transgene-host border band of a size that depends on the position of the nearest host cleavage site. In a double recombination event that translocated the designated DNA fragment, the receptor chromosome should show two new bands of 2.2 and 1.1 while in the donor chromosome a single new 1.9 kb band and the same size transgene-host border fragment.

In instances where recombination was detected, the F1 plants were chimeric for the recombination event. The majority of the hybridization signal was to the parental fragments of 3.1 and 2.5 kb. However, when the blots were subjected to longer exposure times, a recombinant band was detected. Since intense hybridization is seen in the ~2 to 3.1 kb region, the expected 2.2 and 1.9 kb recombinant bands could not be observed over the background. However, the 1.1 kb band was clearly detected in some of the plants, in both floral and leaf tissues. This hybridization pattern was similar for F1 progenies from some other crosses. Both Southern and PCR data indicated that recombination took place in only a minor fraction of the cells.

This low rate of recombination may be due to poor expression of the 35S-int transgene, a position effect of the two participating sites for recombination, and/or a generally low rate of recombination expected for sites that are not located in the same position of homologous chromosomes. Similar, and even lower frequencies of "ectopic" chromosome recombination have been observed previously for Cre-lox mediated chromosome translocations in tobacco (Qin et al., 1994 Proc. Natl. Acad. Sci. USA, 91:1706–10), *Arabidopsis* (this laboratory, unpublished), and in tobacco-*Arabidopsis* hybrid cells (Koshinsky et al., 2000 Plant J. 23:715–22). Nonetheless, the basta resistant phenotype, the PCR detection of the 35S-PB'-bar junction, and the Southern data of the 1.1 kb 35S-BP'-(inverted loxP) junction, are all consistent with a transgene translocation from the donor to the receptor chromosome.

F2 Progeny

Two representative F1 plants from each cross, including those crosses where recombination was not detected, were self-fertilized for F2 seeds. F2 seedlings were sprayed with basta. Table 3 shows that 5 of the 18 crosses had at least one F1 line that yielded basta resistant ($Bar^R$) F2 progeny, 3 other crosses yielded F2 plants that showed partial resistance to basta while the remaining 10 crosses failed to produce $Bar^R$ progeny. This is the same resistance pattern seen in F1 plants using the leaf-painting assay.

Of particular significance is that all three receptor lines yielded $Bar^R$ progeny. This indicates that successful transgene translocation is not confined to rare locations in the genome. Only 4 of the 7 donor lines led to $Bar^R$ progeny, with some of those crosses yielding partial $Bar^R$ plants. The partial resistance may be due to poor expression of the bar gene, such as that caused by gene silencing. A more likely explanation, however, is that the partial basta resistance is due to late somatic recombination rather than germinal transmission of a 35S-PB'-bar junction. Developmentally late recombination events would be expected to have fewer cells with a 35S-PB'-bar linkage.

Interestingly, 8 of the 10 crosses that failed to produce $Bar^R$ progeny have been traced to donor lines CD414-10, CD414-61, and CD414-82. All three lines were estimated to harbor a single copy of the donor DNA. However, it is possible that the lines may not have an intact copy of the pCD414 T-DNA. Undetected DNA rearrangements or point mutations within critical elements of this DNA segment, such as the bar or BB' sequences, could account for the lack of observed recombination.

Within any combination of crosses that yielded resistant plants, not all the sibling plants are alike. Some of the plants appeared more resistant to basta than others, as they grew larger than their siblings. A high level of $Bar^R$ could be due to germinal transmission of the translocation event, or in the case of the cosegregation of both parental donor and receptor chromosome, from a developmentally early recombination event.

F2 seedlings were analyzed by Southern blotting. The DNA was cleaved with the combination of EcoRI, HindIII and SacI and probed with bar DNA. Unlike the 35S probe that hybridizes to a cluster of bands, the bar probe is expected to detect a single 1.1 kb band representing the SacI-HindIII fragment of the donor construct (FIG. 12A). Depending on the amount of recombination, the 2.2 kb 35S-PB'-bar band should be visible. If this band hybridizes with less intensity compared to the 1.1 kb parental band, it represents recombination in somatic cells. If both the male and female gametes transmitted the recombination event, then only the 2.2 kb band, and not the 1.1 kb band, should be present. The 2.2 kb band was visible in all 8 of the F2 seedlings examined, albeit with varying degrees of intensity. In one seedling examined, the 2.2 kb band hybridized with an intensity similar to that of the 1.1 kb band. This banding pattern is consistent with germinal transmission by either the male or the female germline (but not both), leading to a zygote heterozygous for the transgene translocation event. If so, the homologous chromosomes that lack the transgene translocation event (parental configuration) can be segregated away in a backcross to a non-transgenic Columbia ecotype plant. The Bar$^R$ progeny from such a backcross would be hemizygous for the transgene translocation receptor chromosome; and among these, up to half of them should also have segregated away the donor chromosome with the reciprocal translocated locus.

coding region. Expression of aha confers imazethapyr resistance. As before, since the P1-loxP-aha segment is flanked by directly oriented FRT sites, it can be removed subsequently by the introduction of the FLP recombinase (not shown in FIG. 13).

Summary

Current methods of transformation lead to unpredictable integration locations, patterns and copies of the introduced DNA. It is envisioned that generating target receptor lines will consist of using current transformation methods to randomly place the target sites into the genome. Single copy

TABLE 3

[00181] F2 progeny phenotype from derived donor and receptor lines

| Donor line | CD414-8 | CD414-10 | CD414-27 | CD414-24 | CD414-61 | CD414-72 | CD414-82 |
|---|---|---|---|---|---|---|---|
| Donor line transgene copy number | >2 | 1 | 1 | >2 | 1 | 1 | 1 |
| CD426-2 | Bar$^R$ | 0 | 0 | Partial Bar$^R$ | 0 | ND | ND |
| CD426-9 | Bar$^R$ | 0 | Partial Bar$^R$ | Bar$^R$ | 0 | Bar$^R$ | 0 |
| CD426-13 | Bar$^R$ | 0 | 0 | ND | 0 | Partial Bar$^R$ | 0 |

Bar$^R$ indicates basta resistance observed in F1 plants.
Partial Bar$^R$ indicates partial basta resistance observed in F1 plants.
0 indicates basta resistance is not found in F1 plants.
ND indicates that crosses have not been done.

Removal of Unneeded DNA

Figure 12C:
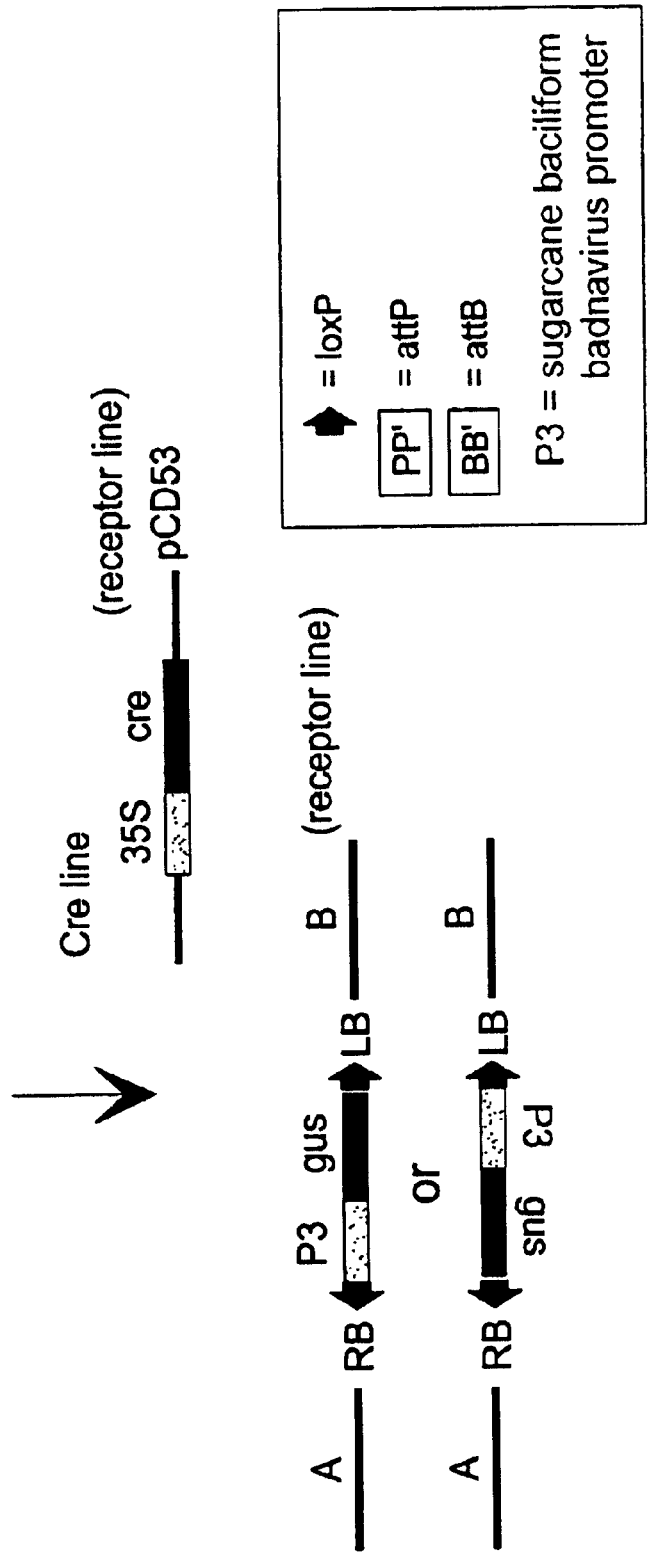

The transgene translocation technology has been designed with the provision that DNA no longer needed after the translocation can be subsequently removed from the host genome. The donor and receptor locus included a set of inverted recombination sites from a second recombination system, in this case, from the Cre-lox system (FIG. 12A). After transgene translocation, the new configuration on the receptor chromosome has sets of directly repeated loxP sites flanking segments of DNA other than the trait gene, which is exemplified by the P3-gus fragment (FIG. 12B). FIG. 12C shows that when crossed to a plant that expresses the cre gene, Cre recombinase-mediated loxP-specific recombination deletes the unneeded DNA, leaving only the trait gene flanked by a set of inverted loxP sites. Since inverted loxP sites can recombine with each other to invert the intervening DNA, the trait gene will be present in either orientation with respect to the plant centromere. This could result in two distinct patterns of expression from a given target site.

Possible Variations

Figure 13:
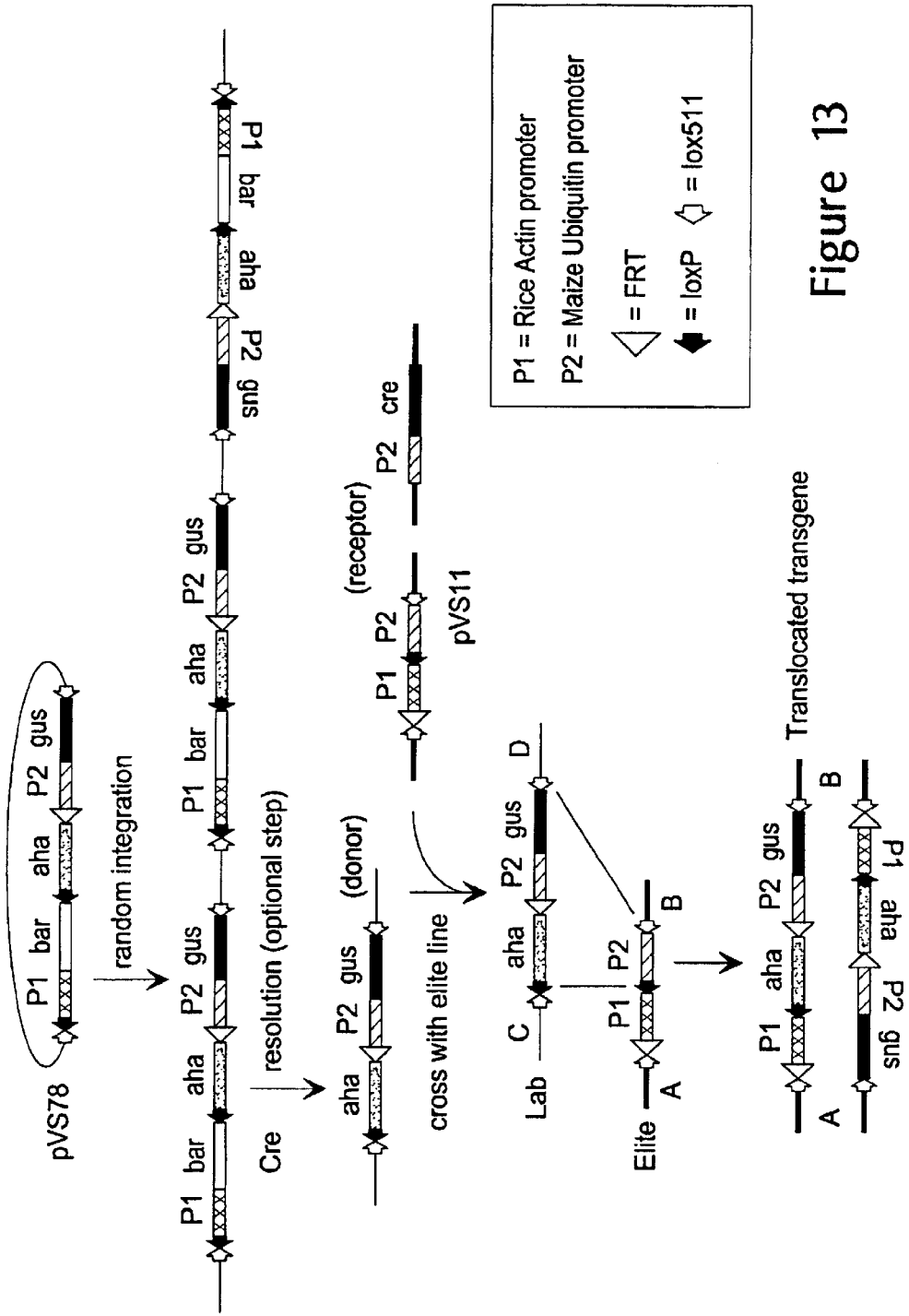
FIG. 13 shows a strategy for site-specific replacement of a polynucleotide between plant chromosomes using reversible recombinases, where Cre-lox is used to translocate the trait gene (P2-gus) from donor to receptor chromosomes, and a second reversible recombination system, such as FLP-FRT, is used to subsequently remove the unneeded DNA.

The specific design shown in these experiments can be modified for use with other recombination systems that, unlike φC31, give freely reversible reactions. One example is shown in FIG. 13, where Cre-lox is used to translocate the trait gene (P2-gus) from donor to receptor chromosomes. A second recombination system, such as FLP-FRT, is used to subsequently remove the unneeded DNA.

The donor construct pVS78 is transformed into the genome at random locations. The P1-bar selectable marker is flanked by directly oriented loxP sites, while the donor construct fragment is flanked by a set of inverted lox511 sites. The lox511 allele does not recombine with loxP. Therefore, if the cre gene is introduced into the genome, loxP×loxP and lox511×lox511 events will resolve the complex locus into a single copy as well as delete the P1-bar marker. This resolution step can be conducted prior to or at the same time that the donor line is crossed into a receptor line. An example of such a receptor line is VS11. As depicted in FIG. 13, double site-specific recombination between donor and receptor chromosomes, loxP×loxP and lox511 and lox511, will form a P1-aha linkage, where P1 is the rice actin promoter and aha is the acetohydroxyacid synthase target lines would be preferable to those with complex multiple copies. The transgene translocation strategy incorporates flanking inverted recombination sites and is therefore compatible with the resolution-based strategy to obtain single copy transformants (Srivastava et al., 1999 Proc. Natl. Acad. Sci USA, 96:11117–11121; Srivastava and Ow, 2001 Plant Mol. Biol. 46:561–566; U.S. Pat. No. 6,114,600).

Once target lines are obtained, they can be characterized for site integrity and expression pattern. Those deemed desirable can serve as target sites for subsequent DNA insertions. The target sites can then be bred out to elite lines. Subsequent delivery of a trait gene (or multiple trait genes within a DNA segment) may proceed by site-specific integration into the target site of the laboratory line, or by random integration of the DNA into the laboratory line genome. The trait gene segment can then translocate from the donor line chromosome to the elite line receptor chromosome, as demonstrated in this example.

On the introduction of target sites into elite backgrounds, it is recognized that elite varieties are constantly evolving. For example, target site may be placed randomly, and it lands next to gene X. The X-target is then backcrossed extensively to, for example, elite line A for Texas, elite line B for Nebraska, and elite line C for Argentina. Over time, the elite lines A, B and C could evolve into new elite lines A2, B2, and C2. But since these new elite lines do not appear de novo and they evolve from progenitors A, B and C, respectively, they would most likely harbor the X-target locus. Therefore, a new transgene, perhaps an improved version of the previous transgene, or a segment of DNA consisting of multiple transgenes, could again be translocated by site-specific recombination into this locus from a laboratory line to elite lines A2, B2 and C2. Once the target lines are established in elite backgrounds, the transgene translocation technology will facilitate transgene shuttling from laboratory to elite lines, and this will save considerable labor and time in the commercialization of transgenic traits.

I claim:

1. A method of obtaining site-specific replacement of a DNA of interest in a plant cell, comprising:
   a) providing a plant cell that comprises a receptor construct, wherein the receptor construct comprises a receptor polynucleotide to be replaced, the receptor polynucleotide being flanked by two or more copies of a irreversible recombination site (IRS);
   b) introducing into the cell a donor construct that comprises a donor polynucleotide to replace the receptor polynucleotide, the donor polynucleotide being flanked by two or more copies of a complementary irreversible recombinase site (CIRS), and
   c) contacting the receptor construct and donor construct with an irreversible recombinase polypeptide;

wherein the irreversible recombinase catalyzes recombination between IRS and CIRS and replacement of the receptor polynucleotide with the donor polynucleotide, thereby forming a replacement construct.

2. The method of claim 1, wherein the donor construct is linear.

3. The method of claim 1, wherein the donor construct is a circular vector.

4. The method of claim 1, wherein the donor construct is a chromosome.

5. The method of claim 1, wherein the receptor construct is a chromosome.

6. The method of claim 1, wherein the receptor construct comprises two copies of the IRS and the donor construct comprises two copies of the CIRS.

7. The method of claim 6, wherein the IRS are inverted with respect to each other and wherein the CIRS are inverted with respect to each other.

8. The method of claim 6, wherein the donor polynucleotide further comprises a promoter operably linked to a DNA of interest.

9. The method of claim 6, wherein the receptor construct further comprises a promoter that is adjacent to one copy of the IRS.

10. The method of claim 9, wherein the promoter is located in the 5 prime direction from the IRS.

11. The method of claim 9, wherein the receptor construct further comprises a second promoter operably linked to a selectable marker.

12. The method of claim 9, wherein the receptor polynucleotide or the donor polynucleotide further comprises a negative selectable marker.

13. The method of claim 9, wherein the receptor polynucleotide or the donor polynucleotide further comprises a nucleic acid encoding the irreversible recombinase polypeptide.

14. The method of claim 13, wherein the receptor polynucleotide comprises the nucleic acid encoding the irreversible recombinase polypeptide.

15. The method of claim 14, wherein the irreversible recombinase is a bacteriophage φC31 integrase.

16. The method of claim 1, wherein the plant cell is an *Arabidopsis thaliana* cell.

* * * * *